(12) United States Patent
Thatcher et al.

(10) Patent No.: US 7,115,661 B1
(45) Date of Patent: Oct. 3, 2006

(54) METHODS AND COMPOSITIONS FOR MITIGATING PAIN

(75) Inventors: Gregory R. J. Thatcher, Kingston (CA); Brian M. Bennett, Kingston (CA); James N. Reynolds, Kingston (CA); Khem Jhamandas, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/473,713

(22) Filed: Dec. 29, 1999

(51) Int. Cl.
*A61K 31/21* (2006.01)
*A61P 25/20* (2006.01)
*A61P 25/22* (2006.01)

(52) U.S. Cl. .................................................. 514/509
(58) Field of Classification Search ................. 514/509
See application file for complete search history.

(56) References Cited

U.S. PATENT DOCUMENTS

| | | | |
|---|---|---|---|
| 3,869,451 A | 3/1975 | Phillipps et al. | |
| 4,780,560 A | 10/1988 | Kumonaka et al. | |
| 4,801,596 A | 1/1989 | Simon et al. | |
| 5,049,694 A | 9/1991 | Bron et al. | |
| 5,284,872 A | 2/1994 | Sandrock et al. | |
| 5,428,061 A | 6/1995 | Sandrock et al. | |
| 5,621,000 A | 4/1997 | Arena et al. | |
| 5,661,129 A | 8/1997 | Feelisch et al. | |
| 5,693,676 A | 12/1997 | Gorfine | |
| 5,700,947 A | 12/1997 | Del Soldato | |
| 5,780,495 A | 7/1998 | Del Soldato | |
| 5,807,847 A * | 9/1998 | Thatcher et al. ............ | 514/129 |
| 5,861,426 A | 1/1999 | Del Soldato et al. | |
| 5,883,122 A * | 3/1999 | Thatcher et al. ............ | 514/509 |
| 5,905,086 A * | 5/1999 | Miura ........................ | 514/310 |
| 6,040,341 A | 3/2000 | Del Soldato et al. | |
| 6,310,052 B1 | 10/2001 | Thatcher et al. ............ | 514/129 |

FOREIGN PATENT DOCUMENTS

| | | |
|---|---|---|
| EP | 0664127 | 7/1995 |
| WO | WO 95/30641 | 11/1995 |
| WO | WO 97/46521 | 12/1997 |
| WO | WO 98/25918 | 6/1998 |
| WO | WO 98/42661 | 10/1998 |
| WO | WO 00/54756 | 9/2000 |

OTHER PUBLICATIONS

Ferreira, S.H., et al., "Blockade of hyperalgesia and neurogenic oedema by topical application of nitroglycerin." *Euro. J. Pharmacol.* 217:207-209 (1992).

Lin, Q., et al., "Involvement of cGMP in nociceptive processing by and sensitization of spinothalamic neurons in primates." *J. Neurosci.* 17(9):3293-3302 (1997).

Mashimo, T., et al., "Effects of vasodilators guanethidine, nicardipine, nitroglycerin, and prostaglandin $E_1$ on primary afferent nociceptors in humans." *J. Clin. Pharmacol.* 37:330-335 (1997).

Aley, K.O., G. McCarter, and J.D. Levin, "Nitric Oxide Signaling in Pain and Nociceptor Sensitization in the Rat." *J. Neurosci.* 18 (1998) 7008-7014.

Artz, J.D. and G.R.J. Thatcher, "NO Release from NO Donors and Nitrovasodilators: Comparisons between Oxyhemoglobin and Potentiometric Assays." *Chem. Res. Toxicol.* 11 (1998) 1393-1397.

Bak, A.W., W. McKnight, P. Li, P. Del Soldato, A. Calignano, G. Cirino and J.L. Wallace, "Cyclooxygenase-Independent Chemoprevention with an Aspirin Derivative in a Rat Model of Colonic Adenocarcinoma." *Life Sci.* 62 (1998) 367-373.

Barger, S.W., R.R. Fiscus, P. Ruth, F. Hofmann, M.P. Mattson, "Role of Cyclic GMP in the Regulation of Neuronal Calcium and Survival By Secreted Forms of β-Amyloid Precursor." *J. Neurochem.* 64 (1995) 2087-2096.

Bennett, B.M., B.J. McDonald, R. Nigam, P.G. Long, and W.C. Simon, "Inhibition of Nitrovasodilator- and Acetylcholine-Induced Relaxation and Cyclic GMP Accumulation by the Cytochrome P-450 Substrate, 7-Ethoxyresorufin." *Can. J. Physiol. Pharmacol.* 70 (1992) 1297-1303.

Berge, S.M., L.D. Bighley, and D.C. Monkhouse, "Pharmaceutical Salts." *J. Pharm. Sci.* 66 (1977) 1-19.

Bloeman, P.G.M., P.A.J. Henricks, L. van Bloois, M.C. van den Tweel, A.C. Bloem, F.P. Nijkamp, D.J.A. Crommelin, and G. Storm, "Adhesion Molecules: a New Target for Immunoliposome-Mediated Drug Delivery." *FEBS Lett.* 357 (1995) 140-144.

Cunha, F.Q., M.M. Teixeira and S.H. Ferreira, "Pharmaceological Modulation of Secondary Mediator Systems-Cyclic AMP and Cyclic GMP—on Inflammatory Hyperalgesia." *Br. J. Pharmacol.* 127 (1999) 671-678.

del Soldato, P.R. Sorrentino and A. Pinto, "NO-aspirins: a Class of New Anti-inflammatory and Antithrombotic Agents." *TiPS* 20 (1999) 319-323.

Ferreira, S.H., "The Role of Interleukins and Nitric Oxide in the Mediation of Inflammatory Pain and its Control by Peripheral Analgesics." *Drugs* 46 (1993) 1-9.

Ferreira, S.H., I.D.G. Duarte and B.B Lorenzetti, "Molecular Base of Acetylcholine and Morphine Analgesia." *AAS* 32 (1991) 101-106.

Fidecka, S. and Lalewicz, "Studies on the Antinociceptive Effects of Sodium Nitroprusside and Molsidomine in Mice." *Polish J. Pharmacol.* 49 (1997) 395-400.

(Continued)

*Primary Examiner*—Christopher S. F. Low
*Assistant Examiner*—C. Delacroix-Muirheid
(74) *Attorney, Agent, or Firm*—Clark & Elbing LLP; Kristina Bieker-Brady

(57) ABSTRACT

Methods and therapeutic compounds for treating pain, mitigating inflammation, effecting analgesia and/or effecting sedation in a subject are described. A subject is administered an effective amount of a therapeutic compound which is a nitrate ester. Novel pharmaceutical compositions are also described.

26 Claims, 15 Drawing Sheets

OTHER PUBLICATIONS

Granados-Soto, V., M. de O. Rufino, L.D.G. Lopes, S.H. Ferreira, "Evidence for the Involvement of the Nitric Oxide-cGMP Pathway in the Antinociception of Morphine in the Formalin Test." Euro. J. Pharmacol. 340 (1997) 177-180.

Inoue, T., M. Takashi, S. Shibuta, I. Yoshiya, "Intrathecal Administration of a New Nitric Oxide Donor, NOC-18, Produces Acute Thermal Hyperalgesia in the Rat." J. Neurol. Sci. 153 (1997) 1-7.

Lauretti, G.R., I.C.P.R. Lima, M.P. Reis, W.A. Prado, N.L. Pereira, "Oral Ketamine and Transdermal Nitroglycerin as Analgesic Adjuvants to Oral Morphine Therapy for Cancer Pain Management." Anesthesiology 90 (1999) 1528-1533.

Louw, R., H.P.W. Vermeeren, J.J.A. Van Asten, and W.J. Ultée, "Reaction of Sulphides with Acyl Nitrates; a Simple and Rapid Method for Preparing Sulphoxides." J. C.S. Chem. Comm. (1976) 496-497.

Macdonald, R.L. and M. Stoodley, "Pathophysiology of Cerebral Ischemia." Neurol. Med. Chir. (Tokyo) 38 (1998) 1-11.

Malmberg, A.B. and T.L. Yaksh, "Pharmacology of the Spinal Action of Ketorolac, Morphine, ST-91, U50488H, and L-PIA on the Formalin Test and an Isobolographic Analysis of the NSAID Interaction." Anesthesiology 79 (1993) 270-281.

McDonald, B.J. and B.M. Bennett, "Cytochrome P-450 Mediated Biotransformation of Organic Nitrates." Can. J. Physiol. Pharmacol. 68 (1990) 1552-1557.

McGuire J.J., D.J. Anderson and B.M. Bennett, "Inhibition of the Biotransformation and Pharmacological Actions of Glyceryl Trinitrate by the Flavoprotein Inhibitor, Diphenyleneiodonium Sulfate." J. Pharmacol. Exp. Ther. 271 (1994) 708-714.

Ouellette, R.J., and R.J. Bertsch, "Formation of Nitrate Esters by the Oxidation of Alkenes and Cyclopropanes with Thallium (III) Nitrate in Pentane." J. Org. Chem. 41 (1976) 2782-2783.

Owais, M., G.C. Varshney, A. Choudhury, S. Chandra, and C.M. Gupta, "Chloroquine Encapsulated in Malaria-Infected Erythrocyte-Specific Antibody-Bearing Liposomes Effectively Controls Chloroquine-Resistant *Plasmodium berghei* Infections in Mice." Antimicrob. Agents Chemother. 39 (1995) 180-184.

Ranade, V.V., "Drug Delivery Systems. 1. Site-Specific Drug Delivery Using Liposomes as Carriers." J. Clin. Pharmacol. 29 (1989) 685-694.

Reynolds, J.N. and R. Maitra, "Propofol and Flurazepam Act Synergistically to Potentiate $GABA_A$ Receptor Activation in Human Recombinant Receptors." Euro. J. Pharmacol. 314 (1996) 151-156.

Salter, M., P.J.L.M. Strijbos, S. Neale, C. Duffy, R.L. Follenfant and J. Garthwaites, "The Nitric Oxide-Cyclic GMP Pathway is Required for Nociceptive Signalling at Specific Loci within the Somatosensory Pathway." Neuroscience 73 (1996) 649-655.

Shibuta, S., T. Mashimo, P. Zhang, A. Ohara, I. Yoshiya, "A New Nitric Oxide Donor, NOC-18, Exhibits a Nociceptive Effect in the Rat Formalin Model." J. Neurol. Sci. 141 (1996) 1-5.

Stewart, D.H., L.D. Hayward, and B.M. Bennett, "Differential Biotransformation of the Enantiomers of Isoidide Dinitrate in Isolated Rat Aorta." Can. J. Physiol. Pharmacol. 67 (1989) 1403-1408.

Stone, J.R. and M.A. Marletta, "Spectral and Kinetic Studies on the Activation of Soluble Guanylate Cyclase by Nitric Oxide." Biochem: 35 (1996) 1093-1099.

Strejan, G.H., J.J. Gilbert, and J. St. Louis, "Suppression of Chronic-Relapsing Experimental Allergic Encephalomyelitis in Strain-13 Guinea Pigs by Administration of Liposome-Associated Myelin Basic Protein." J. Neuroimmunol. 7 (1984) 27-41.

Sydserff, S.G., A.J. Cross, K.J. West, and A.R. Green, "The Effect of Chlormethiazole on Neuronal Damage in a Model of Transient Focal Ischaemia." Br. J. Pharmacol. 114 (1995) 1631-1635.

Thatcher, Gregory R.J. and Hazel Weldon, "NO problem for nitroglycerin: organic nitrate chemistry and therapy." Chem. Soc. Rev. 27 (1998): 331-337.

Tjølsen, A., O.-G. Berge, S. Hunskaar, J.H. Rosland and K. Hole, "The Formalin Test: an Evaluation of the Method." Pain 51 (1992) 5-17.

Umezawa, F. and Y. Eto, "Liposome Targeting to Mouse Brain: Mannose as a Recognition Marker." Biochem. Biophys. Res. Commun. 153 (1988) 1038-1050.

Wu, J., Y. Wang, M.J. Rowan, and R. Anwyl, "Evidence for Involvement of the cGMP-protein Kinase G Signaling System in the Induction of Long-Term Depression, but not Long-term Potentiation, in the Dentate Gyrus *in vitro.*" J. Neurosci. 18 (1998) 3589-3596.

Xu, J.Y., G.M. Pieper and L.F. Tseng, "Activation of a NO-Cyclic GMP System by NO Donors Potentiates β-Endorphin-Induced Antinociception in the Mouse." Pain 63 (1995) 377-383.

Yaksh, T.L., "Spinal Systems and Pain Processing: Development of Novel Analgesic Drugs with Mechanistically Defined Models." TiPS 20 (1999) 329-337.

Yang, K., J.D. Artz, J. Lock, C. Sanchez, B.M. Bennett, A.B. Fraser, and G.R.J. Thatcher, "Synthesis of Novel Organic Nitrate Esters: Guanylate Cyclase Activation and Tissue Relaxation." J. Chem. Soc., Perkin Trans. 1 (1996) 1073-1075.

Burke, D.H., et al., "Sodium nitroprusside-induced hypothermia in mice." J. Pharm. Sci. 66:1658-1660 (1977).

Ferreira, S.H., "Inflammatory pain: the role of cytokines an its control by drugs which release nitric oxide." Ann. 1st. Super. Sanità 29:367-373 (1993).

Golding, P., et al., "Preparation of di- and polynitrates by ring-opening nitration of epoxides by dinitrogen pentoxide $(N_2 O_5)^1$." Tetrahedron 49:7037-7050 (1993).

Reynolds, J.N., et al., "Cognition enhancement and sedative-hypnotic properties with a novel nitrate ester." Abstract, Society for Neuroscience Abstracts vol. 26, Abstract No. 653.9 (2000).

\* cited by examiner

METHODS AND COMPOSITIONS FOR MITIGATING PAIN

FIELD OF THE INVENTION

This invention relates to nitrate esters and use thereof in mitigating pain and effecting analgesia. More particularly this invention relates to organic nitrates which have therapeutic utility as analgesics, anti-inflammatory agents and sedatives.

BACKGROUND OF THE INVENTION

The nitrate ester, glyceryl trinitrate (GTN), or nitroglycerin, has been used as a vasodilator in the treatment of angina pectoris for over a hundred years, and the dominant, contemporary belief is that GTN exerts its therapeutic effect through in vivo release of nitric oxide (NO). Other organic nitrates (nitrate esters), such as isosorbide dinitrate, have also been identified as effective and clinically important vasodilators. NO itself has been identified as Endothelium Derived Relaxing Factor (EDRF) and several classes of compounds, for example nitrosothiols, in addition to organic nitrates, have been proposed as NO donors or NO prodrugs.

Several organic nitrates, in which an alkyl mononitrate is appended to a moiety with analgesic properties, such as aspirin (ASA) or a Non-Steroidal Anti-Inflammatory Drug (NSAID) have been reported as analgesics which possess reduced gastro-intestinal irritation and ulceration properties, purportedly through release of NO. The combination of the vasodilator nitroglycerin with opioid analgesics such as morphine, has been suggested to be effective in the management of both surgical and cancer pain. However, no attempt has been made to develop organic nitrates themselves as analgesic agents, that is, organic nitrates that do not rely on an ASA or NSAID moiety, nor an opiate, for analgesic properties. Thus, there is a need for synthetic organic nitrates as new and useful therapeutic agents for treatment and mitigation of pain associated with disease states and chemotherapy of those disease states.

OBJECT OF THE INVENTION

It is an object of the present invention to provide methods and compositions for use in treating pain and/or conditions associated with pain. Another object of the present invention is to provide methods and compositions for providing analgesia and/or sedation.

BRIEF DESCRIPTION OF THE INVENTION

The present invention is based, at least in part, on the recognition that, although the potent vasodilatatory effects of organic nitrates may be either (a) deleterious to or, alternatively, (b) synergistic with their analgesic effects, regulation of these two effects is required for the development of therapeutic agents useful in treatment and mitigation of pain. Pain may be treated or mitigated by, for example, an analgesic, anti-inflammatory and/or sedative agent.

Possible deleterious effects of organic nitrates may arise, for example, through an NO-donor potentiating hyperalgesia via a cyclic guanosine-3,5-monophosphate (cGMP)-independent mechanism. Alternatively, synergistic effects of organic nitrates may arise, for example, through the ability of an NO-donor to induce analgesia by activation of soluble guanylyl cyclase (GCase) and elevation of cGMP levels. The present invention relates to methods for treating or mitigating pain through use of an organic nitrate, wherein regulation of these two effects is achieved. According to the invention, selection of an appropriate organic nitrate provides modulation and balance between the ability of the organic nitrate to release NO and its potency for GCase activation. Inasmuch as gastrointestinal toxicity is known to be a deleterious side effect of some analgesic drugs and that NO donor molecules are gastro-protective, it is set forth herein that therapeutic analgesia can be achieved through utilization of an appropriate organic nitrate. This statement is based, at least in part, on bioassay data on such compounds.

This invention provides methods and compositions which are useful in treating pain, inhibiting inflammation, and/or providing analgesia. Methods of the invention involve administering to a subject a therapeutic compound (nitrate ester) which provides analgesia. The methods and compositions of the invention are useful for the treatment and mitigation of pain associated with disorders and disease states and chemotherapy of those disease states. The methods and compositions of the invention can be used therapeutically to treat acute, chronic and/or inflammatory pain in conditions such as, but not limited to, nerve injury, postherpetic neuralgia, arthritis, diabetic neuropathy, dysmenorrhea, endometriosis, phantom limb pain, pain associated with cancer and post-operative pain, or can be used prophylactically in a subject susceptible or predisposed to these conditions. In certain preferred embodiments, a therapeutic compound used in the method of the invention interacts with guanylyl cyclase, effecting analgesia. In other preferred embodiments, a therapeutic compound used in the method of the invention modulates levels of the cyclic nucleotides cyclic guanosine-3',5'-monophosphate (cGMP) and cyclic adenosine-3',5'-monophosphate (cAMP).

In one aspect, the invention provides a method for treating pain, treating or inhibiting inflammation, providing analgesia, providing sedation, mitigating anxiety and/or providing anaesthesia in a subject, comprising administering to a subject in need thereof an effective amount of a therapeutic compound, wherein the therapeutic compound is of the formula (Ia):

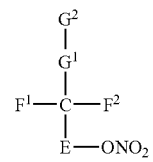

in which E, $F^1$, $F^2$, $G^1$, and $G^2$ are the same or different organic radicals which may be joined in cyclic ring systems, and which may contain inorganic counterions;

with the proviso that when E and $G^1$ are methylene groups and $F^1$ is H, $G^2$ is not a nitrate group, nor $R^N$—$Z^N$;

wherein $R^N$ is any aryl or heteroaryl group and $Z^N$ is $(CO)_{mm}$—$X^N_{nn}$—$Y^N_{oo}$;

wherein mm, nn, oo are 0 or 1 and $X^N$, $Y^N$ are NH, $NR^{NN}$, O or $CH_2$;

wherein $R^{NN}$ is a short chain alkyl group ($C_1$–$C_{12}$).

In a preferred embodiment, $F^2$ is a nitrate group and E, $F^1$, $G^1$, $G^2$ are the same or different organic radicals which may be joined in cyclic ring systems, and which may contain inorganic counterions;

with the proviso that when E and $G^1$ are methylene groups and $F^1$ is H, $G^2$ is not a nitrate group, nor $R^N$—$Z^N$;

wherein $R^N$ is any aryl or heteroaryl group and $Z^N$ is $(CO)_{mm}$—$X^N_{nn}$—$Y^N_{oo}$;

wherein mm, nn, oo are 0 or 1 and $X^N$, $Y^N$ are NH, $NR^{NN}$, O or $CH_2$;

wherein $R^{NN}$ is a short chain alkyl group ($C_1$–$C_{12}$).

In another aspect, the invention provides a method for treating pain, treating or inhibiting inflammation, providing analgesia, providing sedation, mitigating anxiety and/or providing anaesthesia in a subject, comprising administering to a subject in need thereof an effective amount of a therapeutic compound, wherein the therapeutic compound is of the formula (Ib):

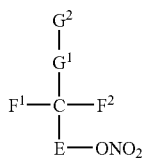

in which $F^2$ is an organic radical which may be joined in a cyclic ring system with $G^2$, and which may contain inorganic counterions; E and $G^1$ are both methylene groups; $F^1$ is H; and $G^2$ is $R^N$—$Z^N$;

wherein $R^N$ is an organic radical possessing a heteroaryl group containing P or S atoms where said P or S are positioned β, γ, or δ to a nitrate group as identified in formula I; and $Z^N$ is $W^N_{mm}$—$X^N_{nn}$—$Y^N_{oo}$;

wherein mm, nn and oo are 0 or 1; and $W^N$, $X^N$, $Y^N$ are NH, $NR_{NN}$, CO, O or $CH_2$;

wherein $R^{NN}$ is a short chain alkyl group ($C_1$–$C_{12}$).

In a preferred embodiment, $F^2$ is a nitrate group; E and $G^1$ are methylene groups; $F^1$ is H; and $G^2$ is $R^N$—$Z^N$;

wherein $R^N$ is an organic radical possessing an heteroaryl group containing P or S atoms where said P or S are positioned β, γ, or δ to a nitrate group as identified in formula I; and $Z^N$ is $W^N_{mm}$—$X^N_{nn}$—$Y^N_{oo}$;

wherein mm, nn, oo are 0 or 1 and $W^N$, $X^N$, $Y^N$ are NH, $NR^{NN}$, CO, O or $CH_2$;

wherein $R^{NN}$ is a short chain alkyl group ($C_1$–$C_{12}$).

In another aspect, the invention provides a method for treating pain, treating or inhibiting inflammation, providing analgesia, providing sedation, mitigating anxiety and/or providing anaesthesia in a subject, comprising administering to a subject in need thereof an effective amount of a therapeutic compound, wherein the therapeutic compound is of the formula (Ic):

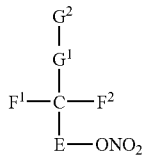

in which E is $(R^1R^2 C)_m$ and $G^2$—$G^1$—$CF^1F^2$— is $R^{19}$—$(R^3R^4C)_p$—$(R^{17}R^{18}C)$—;

wherein:

m, n, p are integers from 0 to 10;

$R^{3,17}$ are each independently hydrogen, a nitrate group, or A; and $R^{1,4}$ are each independently hydrogen, or A;

where A is selected from a substituted or unsubstituted aliphatic group (preferably a branched or straight-chain aliphatic moiety having from 1 to 24 carbon atoms in the chain, which optionally may contain O, S, $NR^6$ and unsaturations in the chain, optionally bearing from 1 to 4 hydroxy, nitrate, amino, aryl, or heterocyclic groups; an unsubstituted or substituted cyclic aliphatic moiety having from 3 to 7 carbon atoms in the aliphatic ring, which optionally may contain O, S, $NR^6$ and unsaturations in the ring, optionally bearing from 1 to 4 hydroxy, nitrate, amino, aryl, or heterocyclic groups; an unsubstituted or substituted aliphatic moiety constituting a linkage of from 0 to 5 carbons, between $R^1$ and $R^3$ and/or between $R^{17}$ and $R^4$, which optionally may contain O, S, $NR^6$ and unsaturations in the linkage, and optionally bearing from 1 to 4 hydroxy, nitrate, amino, aryl, or heterocyclic groups); a substituted or unsubstituted aliphatic group (preferably a branched, cyclic or straight-chain aliphatic moiety having from 1 to 24 carbon atoms in the chain) containing carbonyl linkages (e.g., C=O, C=S, C=NOH), which optionally may contain O, S, $NR^6$ and unsaturations in the chain, optionally bearing from 1 to 4 hydroxy, nitrate, amino, aryl, or heterocyclic groups; a substituted or unsubstituted aryl group; a heterocyclic group; amino (including alkylamino, dialkylamino (including cyclic amino, diamino and triamino moieties), arylamino, diarylamino, and alkylarylamino); hydroxy; alkoxy; a substituted or unsubstituted aryloxy;

wherein X is F, Br, Cl, $NO_2$, $CH_2$, $CF_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2H$, $PO_2M$, $P(O)(OR^{14})$, $P(O)(R^{13})$, SO, $SO_2$, $C(O)(SR^{13})$, $SR^5$, $SSR^7$ or $SSR^5$;

Y is F, Br, Cl, $CH_3$, $CF_2H$, $CF_3$, OH, $NH_2$, $NHR^6$, $NR^6R^7$, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(OR^{13})$, $C(O)(SR^{13})$, $SR^5$, $SSR^7$ or $SSR^5$, or does not exist;

$R^2$, $R^5$, $R^{18}$, $R^{19}$ are optionally hydrogen, A or X—Y;

$R^6$, $R^7$, $R^8$, $R^9$, $R^{11}$, $R^{12}$, $R^{13}$, $R^{14}$, $R^{15}$, $R^{16}$ are the same or different alkyl or acyl groups containing 1–24 carbon atoms which may contain 1–4 $ONO_2$ substituents; or $C_1$–$C_6$ connections to $R^1$–$R^4$ in cyclic derivatives which may contain 1–4 $ONO_2$ substituents; or are each independently hydrogen a nitrate group or A;

M is H, $Na^+$, $K^+$, $NH_4^+$, $N^+H_kR^{11}_{(4-k)}$ where k is 0–3; or other pharmaceutically acceptable counterion;

and with the proviso that when m=n=p=1 and $R^{19}$, $R^2$, $R^{18}$, $R^1$=H and $R^{17}$, $R^3$ are nitrate groups, $R^4$ is not H.

In a preferred embodiment, $R^{19}$ is X—Y.

In other embodiments, $R^1$ and $R^3$ are the same or different and selected from H and $C_1$–$C_4$, alkyl chains, which chains may include one O linking $R^1$ and $R^3$ to form pentosyl, hexosyl, cyclopentyl, or cyclohexyl rings, which rings may optionally bear hydroxyl substituents;

$R^2$ and $R^4$ are the same or different and selected from H, a nitrate group, $C_1$–$C_4$ alkyl chains optionally bearing 1–3 nitrate groups, and acyl groups (—$C(O)R^5$);

$R^7$, $R^{11}$ are the same or different $C_1$–$C_8$ alkyl or acyl;

$R^5$, $R^6$, $R^8$, $R^9$, $R^{12}$, $R^{13}$, $R^{14}$, $R^{15}$, $R^{16}$ are the same or different and are alkyl groups containing 1–12 carbon atoms which may contain 1–4 $ONO_2$ substituents; or $C_1$ or $C_2$ connections to $R^1$–$R^3$ in cyclic derivatives; and M is H, $Na^+$, $K^+$, $NH_4^+$ or $N^+H_kR^{11}{}_{(4-k)}$, where k is 0–3.

In other embodiments, m=1, n=0, p=1.

In further embodiments, X is $CH_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2M$, $P(O)(OR^{14})$, $P(O)(R^{13})$, SO, $SO_2$, $C(O)(SR^{13})$, or $SSR^4$; and Y is CN, $N_2H_2R^{13}$, $N_2HR^{13}R^{14}$, $N_3$, SCN, $SCN_2H_2(R^{15})_2$, $SC(O)N(R^{15})_2$, $SC(O)NHR^{15}$, $SO_3M$, $SR^4$, $SO_2M$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(SR^{13})$, $SR^5$, or $SSR^5$, or does not exist.

In yet further embodiments, $R^5$, $R^6$, $R^8$, $R^9$, $R^{12}$, $R^{13}$, $R^{14}$, $R^{15}$, $R^{16}$ are the same or different and are alkyls containing 1–12 carbon atoms; or $C_1$ or $C_2$ connections to $R^1$ or $R^3$ in cyclic derivatives;

X is $CH_2$, O, NH, NMe, S, $SO_3M$, SH, $SR^7$, $SO_2M$, $S(O)R^8$, $S(O)_2R^9$, $S(O)OR^8$, $S(O)_2OR^9$, $PO_3M_2$, $P(O)(OR^{15})(OR^{16})$, $P(O)(OR^{16})(OM)$, $P(O)(R^{15})(OR^8)$, $PO_3HM$ or $P(O)(OM)R^{15}$; and Y is $SO_2M$, $SO_3M$, $PO_3HM$, $PO_3M_2$, $P(O)(OR^{15})(OR^{16})$, $P(O)(OR^{16})(OM)$, $SR^5$, $SR^4$ or $SSR^5$, or does not exist.

In preferred embodiments, therapeutic compounds of the invention act as analgesic, sedative and/or anti-inflammatory agents. Preferred therapeutic compounds for use in the invention include compounds having the formula Formula II):

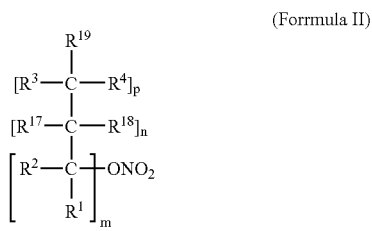

(Formula II)

in which: m and n and p are integers from 0 to 10;

$R^{3,17}$ are each independently hydrogen; a nitrate group; or A;

$R^{1,4}$ are each independently hydrogen; or A;

where A is selected from: a substituted or unsubstituted aliphatic group (preferably a branched, or straight-chain aliphatic moiety having from 1 to 24 carbon atoms in the chain, which optionally may contain O, S, $NR^6$ and unsaturations in the chain, optionally bearing from 1 to 4 hydroxy, or nitrate, or amino or aryl, or heterocyclic groups; an unsubstituted or substituted cyclic aliphatic moiety having from 3 to 7 carbon atoms in the aliphatic ring, which optionally may contain O, S, $NR^6$ and unsaturations in the ring, optionally bearing from 1 to 4 hydroxy, or nitrate, or amino or aryl, or heterocyclic groups; an unsubstituted or substituted aliphatic moiety constituting a linkage of from 0 to 5 carbons, between $R^1$ and $R^3$ and/or between $R^{17}$ and $R^4$, which optionally may contain O, S, $NR^6$ and unsaturations in the linkage, and optionally bearing from 1 to 4 hydroxy, or nitrate, or amino or aryl, or heterocyclic groups); a substituted or unsubstituted aliphatic group (preferably a branched, cyclic or straight-chain aliphatic moiety having from 1 to 24 carbon atoms in the chain), containing carbons linkages (e.g., C=O, C=S, C=NOH), which optionally may contain O, S, $NR^6$ and unsaturations in the chain, optionally bearing from 1 to 4 hydroxy, or nitrate, or amino or aryl, or heterocyclic groups; a substituted or unsubstituted aryl group; a heterocyclic group; amino (inclu moieties), arylamino, diarylamino, and alkylarylamino); hydroxy; alkoxy, a substituted or unsubstituted aryloxy;

$R^2$, $R^5$, $R^{18}$, $R^{19}$ are optionally hydrogen; or A; or X—Y.

where X is F, Br, Cl, $NO_2$, $CH_2$, $CF_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2H$, $PO_2M$, $P(O)(OR^{14})$, $P(O)(R^{13})$, SO, $SO_2$, $C(O)(SR^{13})$, $SR^5$, $SSR^7$ or $SSR^5$, Y is F, Br, Cl, $CH_3$, $CF_2H$, $CF_3$, OH, $NH_2$, $NHR^6$, $NR^6R^7$, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(OR^{13})$, $C(O)(SR^{13})$, $SR^5$, $SSR^2$ or $SSR^5$, or does not exist;

$R^6$, $R^7$, $R^8$, $R^9$, $R^{10}$, $R^{11}$, $R^{12}$, $R^{13}$, $R^{14}$, $R^{15}$, $R^{16}$ are the same or different alkyl or acyl groups containing 1–24 carbon atoms which may contain 1–4 $ONO_2$ substituents; or $C_1$–$C_6$ connections to $R^1$–$R^4$ in cyclic derivatives; or are each independently hydrogen; a nitrate group; or W;

M is H, $Na^+$, $K^+$, $NH_4^+$, $N^+H_kR^{11}{}_{(4-k)}$ where k is 0–3, or other pharmaceutically acceptable counterion;

and with the proviso that, when m=n=p=1; $R^{19}$, $R^2$, $R^{18}$, $R^1$=H; $R^{17}$, $R^3$ are nitrate groups; that $R^4$ is not H or $C_1$–$C_3$ alkyl.

In certain preferred embodiments, therapeutic compounds of the invention are analgesic, sedative and/or anti-inflammatory agents. Preferred therapeutic compounds for use in the invention include compounds in which $R^{19}$ is X—Y. In a particularly preferred embodiment: $R^{19}$ is X—Y and $R^5$, $R^6$, $R^8$, $R^9$, $R^{10}$, $R^{12}$, $R^{13}$, $R^{14}$, $R^{15}$, $R^{16}$ are the same or different alkyl groups containing 1–24 carbon atoms which may contain 1–4 $ONO_2$ substituents, or $C_1$ or $C_2$ connections to $R^1$–$R^3$ in cyclic derivatives; $R^1$ and $R^3$ are the same or different and selected from H, $C_1$–$C_4$, alkyl chains, which may inlude one O, linking $R^1$ and $R^3$ to form pentosyl, hexosyl, cyclopentyl, or cyclohexyl rings, which rings may optionally bear hydroxyl substituents; $R^2$ and $R^4$, are the same or different and selected from H, a nitrate group, $C_1$–$C_4$ alkyl optionally bearing 1–3 nitrate groups, and acyl groups (—$C(O)R^5$); $R^7$, $R^{11}$ are the same or different $C_1$–$C_8$, alkyl or acyl.

In certain embodiments in which $R_{19}$ is X—Y, m, p=1, and n=0. In other embodiments in which $R_{19}$ is X—Y, X is selected from $CH_2$, O, NH, NMe, CN, NHOH, $N_2H_3N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2M$, $P(O)(OR^{14})$, $P(O)(R^{13})$, SO, $SO_2$, $C(O)(SR^{13})$, $SSR^4$. In another embodiment in which $R_{19}$ is X—Y, Y is selected from CN, $N_2H_2R^{13}$, $N_2HR^{13}R^{14}$, $N_3$, SCN, $SCN_2H_2(R^{15})_2$, $SC(O)N(R^{15})_2$, $SC(O)NHR^{15}$, $SO_3M$, $SR^4$, $SO_2M$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(SR^{13})$, $SR^5$, $SSR^5$, or does not exist. In a further embodiment, X and/or Y contain a sulfur-containing functional group. In certain preferred embodiments, the compound of the invention comprises a heterocyclic functionality, more preferably, a nucleoside or nucleobase. In further preferred embodiments, the compound of the invention comprises a carbocyclic functionality, more preferably, a steroidal or carbohydrate moiety.

In another aspect, a therapeutic compound of the invention is represented by the formula (Formula III):

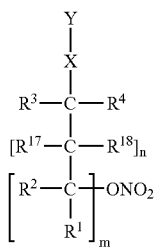

in which: m is 1–10; $R^{1-18}$, X, and Y have the meaning as defined above. In certain preferred embodiments, $R^6$–$R^{16}$ are the same or different alkyl or acyl groups containing 1–24 carbon atoms which may contain 1–4 $ONO_2$ substituents, or $C_1$–$C_6$ connections to $R^1$–$R^4$ in cyclic derivatives. In certain preferred embodiments, $R^{18}$ is A and n=1.

In preferred embodiments, a therapeutic compound of the invention is represented by the formula (Formula IV):

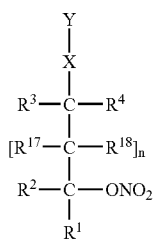

in which: $R^3$, $R^1$=H; n, $R^2R^{4-18}$, X, and Y have the meaning as defined above. In preferred embodiments, X is $CH_2$ or does not exist, and Y is selected from, F, Br, Cl, $CH_3$, $CF_2H$, $CF_3$, OH, $NH_2$, $NHR_6$, $NR_6R_7$, CN, NHOH, $N_2H_3$, $N_2H_2R_{13}$, $N_2HR_{13}R_{14}$, $N_3$, S, SCN, $SCN_2H_2(R_{15})_2$, $SCN_2H_3(R_{15})$, $SC(O)N(R_{15})_2$, $SC(O)NHR_{15}$, $SO_3M$, SH, $SR_7$, $SO_2M$, $S(O)R_8$, $S(O)_2R_9$, $S(O)OR_8$, $S(O)_2OR_9$, $PO_2HM$, $PO_3M_2$, $P(O)(OR_{15})(OR_{16})$, $P(O)(OR_{16})(OM)$, $P(O)(R_{15})(OR_8)$, $P(O)(OM)R_{15}$, $CO_2M$, $CO_2H$, $CO_2R_{11}$, $C(O)R_{12}$, $C(O)(OR_{13})$, $C(O)(SR_{13})$, $SR_5$, $SSR_7$ or $SSR_5$. In certain preferred embodiments, $R_2$ and $R_4$ are optionally H, a nitrate group or a connection to $R_5$–$R_{16}$ in cyclic derivatives.

In certain preferred embodiments, a compound of the invention is represented by the formula (Formula V):

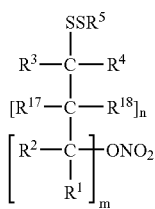

in which m, n, $R^{1-18}$, X, and Y have the meaning as defined above.

In another aspect, the invention includes novel compounds useful for treating pain, mitigating inflammation, effecting analgesia and/or providing sedation. The compounds of the invention can be represented by the structures shown hereinbelow, for example, the structures of Formula III, IV and V. Novel compounds of the invention include nitrates IIIr–IIIaj, IVn–IVt, and Vd–Vag, whose syntheses are described in the following examples.

The invention also provides methods for treating a disease state associated with inflammation, comprising administering to a subject an effective amount of a therapeutic compound having a formula set forth above, such that a disease state associated with inflammation is treated.

The invention further provides methods for treating a disease state or disorder in which a level of sedation is desired, comprising administering to a subject an effective amount of a sedative therapeutic compound having a formula set forth above, such that a disease state or disorder is treated.

The invention provides methods for effecting analgesia comprising administering to a subject an effective amount of a therapeutic compound having a formula set forth above, such that analgesia is effected.

The invention further provides novel pharmaceutical compositions for treating pain, mitigating inflammation, effecting analgesia and/or effecting sedation. A said pharmaceutical composition comprises a therapeutic compound of the invention in an effective amount for the particular indication and a pharmaceutically acceptable vehicle.

The invention also provides packaged pharmaceutical compositions for treating pain, mitigating inflammation, effecting analgesia and/or effecting sedation. The packaged pharmaceutical compositions include a therapeutic compound of the invention and instructions for using the pharmaceutical composition for treatment of inflammation and/or pain.

DETAILED DESCRIPTION OF THE INVENTION

Figure 1:
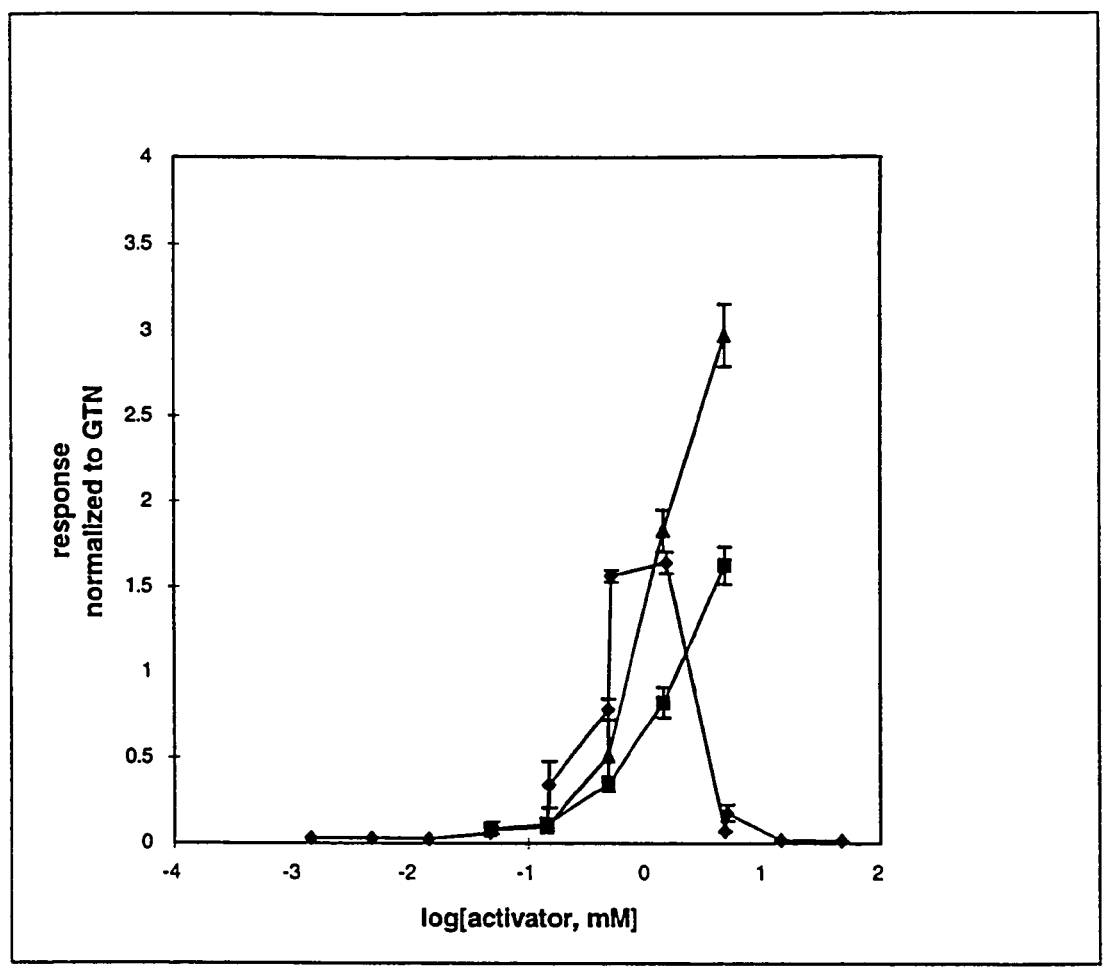
FIG. 1 is a graph showing the effect of IVd neat (diamonds); with added L-cysteine (2 mM, triangles); with added dithiothreitol (2 mM, DTT, squares); on soluble GCase activity in rat aorta homogenate normalized to the maximal GTN response. Bars represent the mean±standard errors calculated separately for each point.

In accordance with the invention there are provided methods and compositions useful in the treatment of pain. Methods of the invention involve administering to a subject an effective amount of a therapeutic compound which provides analgesia, mitigates inflammation and/or provides sedation. In some embodiments, the invention provides prophylactic methods for avoiding or preempting pain, inflammation and the like in a subject. For example, the subject may be susceptible or predisposed to these conditions, e.g., arthritic. Alternatively, the subject may be undergoing a course of treatment, e.g. cancer chemotherapy, which produces pain, inflammation or the like as a side effect. Methods of the invention may be practiced prior to, concurrently with, or after such a course of treatment.

In accordance with the invention, analgesic, anti-inflammatory and/or sedative activity can be effected by modulating an interaction with guanylyl cyclase (GCase; the enzyme responsible for cGMP production in various areas of the body), and/or by modulating levels of cGMP and cAMP messenger molecules.

As used herein, the term "treating" pain encompasses preventing, ameliorating, mitigating and/or managing pain and/or conditions that may cause pain, such as inflammation. As used herein, "inhibiting" pain or inflammation encompasses preventing, reducing and halting progression of same. The terms "organic nitrate" and "nitrate ester" are used interchangeably herein, with no distinction drawn between them.

According to one aspect of the invention, there is provided a method for treating pain in a subject, comprising administering to the subject an effective amount of a compound (nitrate ester) which effects analgesia in the subject. Preferably, analgesia is effected by stimulating GCase. In vivo, GCase activation is effected by nitric oxide (NO), the proximal activator of GCase, which is generated endogenously by enzyme action on arginine in response to many biological triggers (J. R. Stone and M. A. Marletta, *Biochemistry* (1996) 35, 1093). One of the major targets for organic nitrates is GCase activation, resulting in the production of cGMP. In this respect, organic nitrates act as NO-surrogates. In some cases, there is evidence that organic nitrates may act also as NO-donors, but these two properties should be differentiated and can be modulated by choice of the appropriate organic nitrate.

Experimental evidence obtained in a number of in vivo model systems supports the notion that elevated levels of cGMP help effect analgesia. Sodium nitroprusside (SNP), which releases NO non-enzymatically, blocked the hyperalgesic effect of prostaglandin ($PGE_2$) in a rat paw pressure test (Ferreira et al., 1991). Moreover, this effect was potentiated by an inhibitor of cGMP phosphodiesterase, and blocked by an inhibitor of GCase (Ferreira et al., 1991). The peripheral analgesic effects of morphine were attributed to elevations of cGMP levels in sensory nerve fibres (Ferreira et al., 1991; Granados-Soto et al., 1997) in both the rat paw pressure and formalin tests, since inhibition of GCase activity attenuated the analgesic effects of locally applied morphine. Activation of the NO-cGMP system by NO donors such as SNP has also been reported to potentiate beta-endorphin-induced analgesia in thermal tail-flick test in mice (Xu et al., 1995), an effect that was potentiated by a selective inhibitor (zaprinast) of a cGMP-specific phosphodiesterase.

Sensitization of sensory nerve fibres leading to hyperalgesia is assumed to involve increased concentrations of cAMP and calcium ions in sensory neurons, a process that may be attenuated or counteracted by activation of the NO-cGMP pathway (Ferreira, 1993; Cunha et al., 1999).

In accordance with another embodiment of the invention, administration of an effective amount of a therapeutic compound to a subject effects analgesia in the subject by modulating levels of cAMP and/or cGMP. For example, it has been shown that NO-donors modulate hyperalgesia via modulation of levels of cAMP, separately from and in addition to modulation of cGMP levels, in rat models of pain and nociceptor sensitization (Aley et al. 1998). Thus, modulation of cAMP/cGMP levels is expected to be effective in inducing analgesia and in pain management in individuals suffering injury, disease or aging.

In a further embodiment of the invention, there is provided a method for treating or inhibiting inflammation in a subject, comprising administering to the subject an effective amount of a compound which mitigates inflammation in the subject. Preferably, inflammation is mitigated by modulation of levels of cGMP/cAMP. Inflammatory hyperalgesia has been shown to be linked directly to the NO-cGMP pathway (Ferreira, 1993).

We have shown in our co-pending application U.S. Ser. No. 09/267,379, filed Mar. 15, 1999, now U.S. Pat. No. 6,310,052, which is hereby incorporated by reference, that novel nitrate esters have differential effects to activate soluble GCase and to cause cGMP accumulation in vascular and brain tissue. Further, we have shown that the structure of the organic nitrate can be varied to alter potency and efficacy towards both activation of GCase and accumulation of cGMP and effects resulting from these processes in intact tissue, such as aortic strip relaxation. Activation of GCase and accumulation of cGMP have been shown to be important in the induction of analgesia. We show herein that novel organic nitrates are effective analgesics in animal models of pain management. The mouse writhing model, with a relatively short time course of minutes, is a preclinical model of acute pain; whereas formalin injection in the rat paw is a preclinical model of acute and sensitization pain with a time course of minutes to hours, which effectively mimics the hyperalgesia/allodynia underlying pain due to tissue damage (Yaksh, 1999).

In a further embodiment, the invention relates to a method for providing sedation and/or anaesthesia in a subject, comprising administering to the subject an effective amount of a compound (organic nitrate) which effects sedation or anaesthesia in the subject. In certain aspects, the invention provides methods and compositions useful for reducing anxiety, and/or aiding or inducing sleep.

γ-Aminobutyric acid (GABA) is the major inhibitory neurotransmitter in the mammalian (including human) central nervous system. GABA acts on three major classes of neurotransmitter receptor, designated type A ($GABA_A$), type B ($GABA_B$) and type C ($GABA_C$). $GABA_A$ receptors play an important role in regulating many behavioural and physiological functions. Thus, drugs that modulate $GABA_A$ receptor function are among the most widely used in clinical medicine. For example, drugs that selectively potentiate $GABA_A$ receptor function (such as the benzodiazepines) are extensively used to relieve anxiety, produce sedation and induce sleep. Given the importance of this receptor mechanism in clinical medicine, there is a constant search for new chemical entities that modulate $GABA_A$ function, as the currently available drugs have several side effects, including ataxia, amnesia, tolerance and physical dependence. We show herein that organic nitrates that act as positive allosteric modulators of $GABA_A$ receptor function have sedative properties in the whole animal that are comparable to known drugs. This effect of organic nitrates has not previously been recognized or reported. Our findings provide direct evidence that nitrate esters are useful as sedative agents. Such agents are useful as therapeutics for treating conditions such as, for example, anxiety and pain associated with disease states; and as hypnotic agents. According to the invention, nitrate esters may also be employed prophylactically, to prevent or reduce anxiety, or to aid sleep.

Therapeutic compounds of the invention comprise at least one nitrate group. The nitrate groups(s) can optionally be covalently bound to a carrier (e.g., an aromatic group, an aliphatic group, peptide, steroid, nucleobase, nucleoside, peptidomimetic, steroidomimetic, or nucleoside analogue, or the like). In addition to functioning as a carrier for the nitrate functionality, the carrier molecule can enable the compound to traverse biological membranes and to be biodistributed preferentially, without excessive or premature metabolism. Further, in addition to functioning as a carrier for the nitrate functionality, the carrier molecule can enable the compound to exert amplified analgesic, sedative, or anti-inflammatory effects through synergism with the nitrate functionality.

In one embodiment, the invention provides a method comprising administering to a subject an effective amount of a therapeutic compound which has at least one nitrate group and is capable of effecting analgesia. In another embodiment, the therapeutic compound is capable of mitigating inflammation. In a further embodiment, the therapeutic compound is capable of effecting sedation. In the respective embodiments, the therapeutic compound has the formula (Formula I):

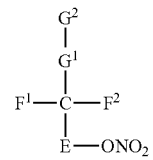

wherein: E, $F^1$, $F^2$, $G^1$, $G^2$ are the same or different organic radicals which maybe joined in cyclic ring systems, and which may contain inorganic counterions.

In further aspects of the invention, therapeutic compounds of the invention effect analgesia, effect sedation and/or mitigate inflammation in a subject to which the therapeutic compound is administered, and have the formula (Formula II).

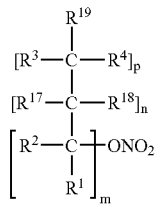

in which: m, n, p are integers from 0 to 10; $R^{3,17}$ are each independently hydrogen; a nitrate group; or A; $R^{1,4}$ are each independently hydrogen; or A; where A is selected from: a substituted or unsubstituted aliphatic group (preferably a branched, or straight-chain aliphatic moiety having from 1 to 24 carbon atoms in the chain, which optionally may contain O, S, $NR^6$ and unsaturations in the chain, optionally bearing from 1 to 4 hydroxy, or nitrate, or amino or aryl, or heterocyclic groups; an unsubstituted or substituted cyclic aliphatic moiety having from 3 to 7 carbon atoms in the aliphatic ring, which optionally may contain O, S, $NR^6$ and unsaturations in the ring, optionally bearing from 1 to 4 hydroxy, or nitrate, or amino or aryl, or heterocyclic groups; an unsubstituted or substituted aliphatic moiety constituting a linkage of from 0 to 5 carbons, between $R^1$ and $R^3$ and/or between $R^{17}$ and $R^4$, which optionally may contain O, S, $NR^6$ and unsaturations in the linkage, and optionally bearing from 1 to 4 hydroxy, or nitrate, or amino or aryl, or heterocyclic groups); a substituted or unsubstituted aliphatic group (preferably a branched, cyclic or straight-chain aliphatic moiety having from 1 to 24 carbon atoms in the chain), containing carbonyl linkages (e.g., C=O, C=S, C=NOH), which optionally may contain O, S, $NR^6$ and unsaturations in the chain, optionally bearing from 1 to 4 hydroxy, or nitrate, or amino or aryl, or heterocyclic groups; a substituted or unsubstituted aryl group; a heterocyclic group; amino (including alkylamino, dialkylamino (including cyclic amino, diamino and triamino moieties), arylamino, diarylamino, and alkylarylamino); hydroxy; alkoxy; a substituted or unsubstituted aryloxy; $R^2$, $R^5$, $R^{18}$, $R^{19}$ are optionally hydrogen; or A; or X—Y; where X is F, Br, Cl, $NO_2$, $CH_2$, $CF_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, S(O) $R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), C(O)$R^{12}$, $C(O)(OR^{13})$, $PO_2H$, $PO_2M$, $P(O)(OR^{14})$, $P(O)(R^{13})$, SO, $SO_2$, $C(O)(SR^{13})$, $SR^5$, $SSR^7$ or $SSR^5$; Y is F, Br, Cl, $CH_3$, $CF_2H$, $CF_3$, OH, $NH_2$, $NHR^6$, $NR^6R^7$, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(OR^{13})$, $C(O)(SR^{13})$, $SR^5$, $SSR^7$ or $SSR^5$, or does not exist; $R^6$, $R^7$, $R^8$, $R^9$, $R^{10}$, $R^{11}$, $R^{12}$, $R^{13}$, $R^{14}$, $R^{15}$, $R^{16}$ are the same or different alkyl or acyl groups containing 1–24 carbon atoms which may contain 1–4 $ONO_2$ substituents; or $C_1$–$C_6$ connections to $R^1$–$R^4$ in cyclic derivatives; or are each independently hydrogen; a nitrate group; or A; M is H, $Na^+$, $K^+$, $NH_4^+$, $N^+H_kR^{11}_{(4-k)}$ where k is 0–3, or other pharmaceutically acceptable counterion.

Preferred therapeutic compounds for use in the invention include compounds in which $R^{19}$ is X—Y. In a particularly preferred embodiment: $R^{19}$ is X—Y and $R^5$, $R^6$, $R^8$, $R^9$, $R^{10}$, $R^{12}$, $R^{13}$, $R^{14}$, $R^{15}$, $R^{16}$ are the same or different alkyl groups containing 1–24 carbon atoms which may contain 1–4 $ONO_2$ substituents, or $C_1$ or $C_2$ connections to $R^1$–$R^3$ in cyclic derivatives; $R^1$ and $R^3$ are the same or different and selected from H, $C_1$–$C_4$, alkyl chains, which may inlude one O, linking $R^1$ and $R^3$ to form pentosyl, hexosyl, cyclopentyl, or cycohexyl rings, which rings may optionally bear hydroxyl substituents; $R^2$ and $R^4$, are the same or different and selected from H, a nitrate group, $C_1$–$C_4$ alkyl optionally bearing 1–3 nitrate group, and acyl groups (—C(O)$R^5$); $R^7$, $R^{11}$ are the same or different $C_1$–$C_8$, alkyl or acyl.

In certain embodiments in which $R_{19}$ is X—Y, m, p=1, and n=0. In other embodiments in which $R_{19}$ is X—Y, X is selected from $CH_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), C(O)$R^{12}$, $C(O)(OR^{13})$, $PO_2M$, $P(O)(OR^{14})$, $P(O)(R^{13})$, SO, $SO_2$, $C(O)(SR^{13})$, $SSR^4$. In another embodiment in which $R_{19}$ is X—Y, Y is selected from CN, $N_2H_2R^{13}$, $N_2HR^{13}R^{14}$, $N_3$, SCN, $SCN_2H_2(R^{15})_2$, $SC(O)N(R^{15})_2$, $SC(O)NHR^{15}$, $SO_3M$, $SR^4$, $SO_2M$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(SR^{13})$, $SR^5$, $SSR^5$, or does not exist. In a further embodiment, X and/or Y contain a sulfur-containing functional group. In certain preferred embodiments, the compound of the invention comprises a heterocyclic functionality, more preferably, a nucleoside or nucleobase. In further preferred embodiments, the compound of the invention comprises a carbocyclic functionality, more preferably, a steroidal or carbohydrate moiety.

In another aspect of the invention, a therapeutic compound of the invention is represented by the formula (Formula III):

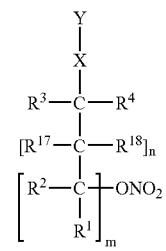

in which: m, n are 1–10; $R^{1-18}$, X, and Y have the meaning as defined above. In certain preferred embodiments, $R^6$–$R^{16}$ are the same or different alkyl or acyl groups containing 1–24 carbon atoms which may contain 1–4 $ONO_2$ substituents, or $C_1$–$C_6$ connections to $R^1$–$R^4$ in cyclic derivatives. In certain preferred embodiments, $R^{18}$ is A and m=n=1. In further preferred embodiments, therapeutic compounds of the invention have a formula selected from (Formulae IIIa–IIIam):

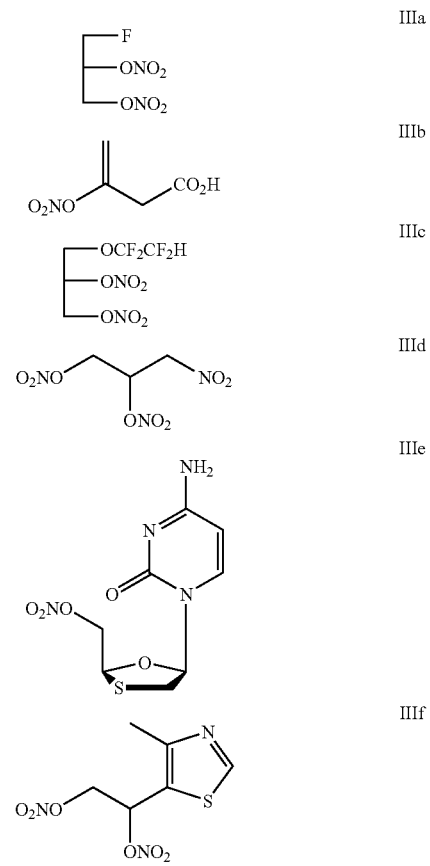

-continued
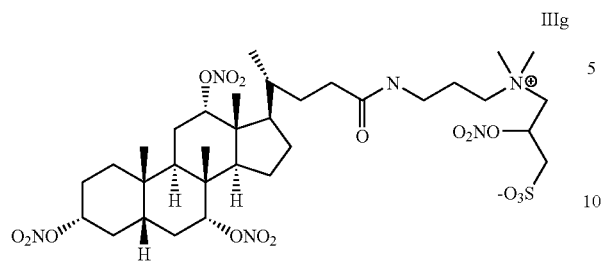 IIIg
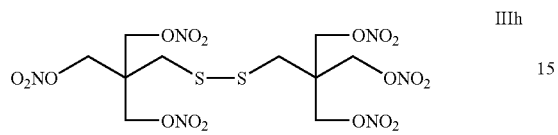 IIIh
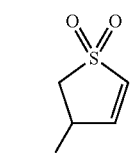 IIIi
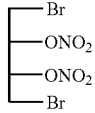 IIIj
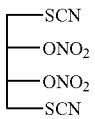 IIIk
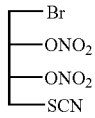 IIIl
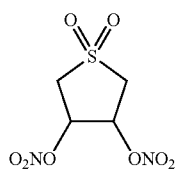 IIIm
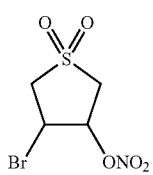 IIIn
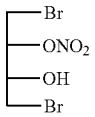 IIIo
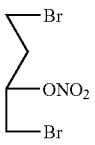 IIIp
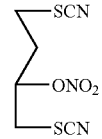 IIIq
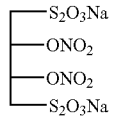 IIIr
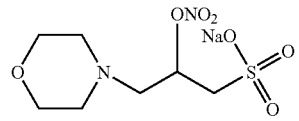 IIIs
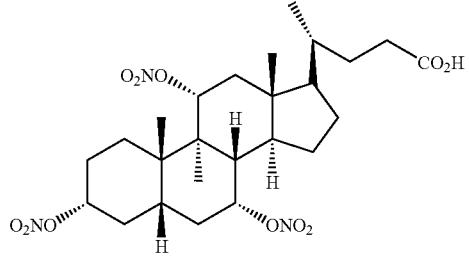 IIIt
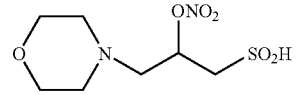 IIIu
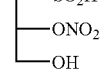 IIIv
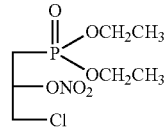 IIIw
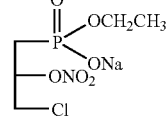 IIIx
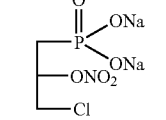 IIIy
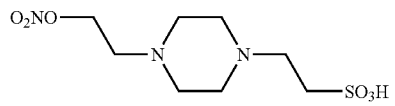 IIIz
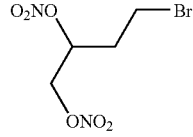 IIIaa

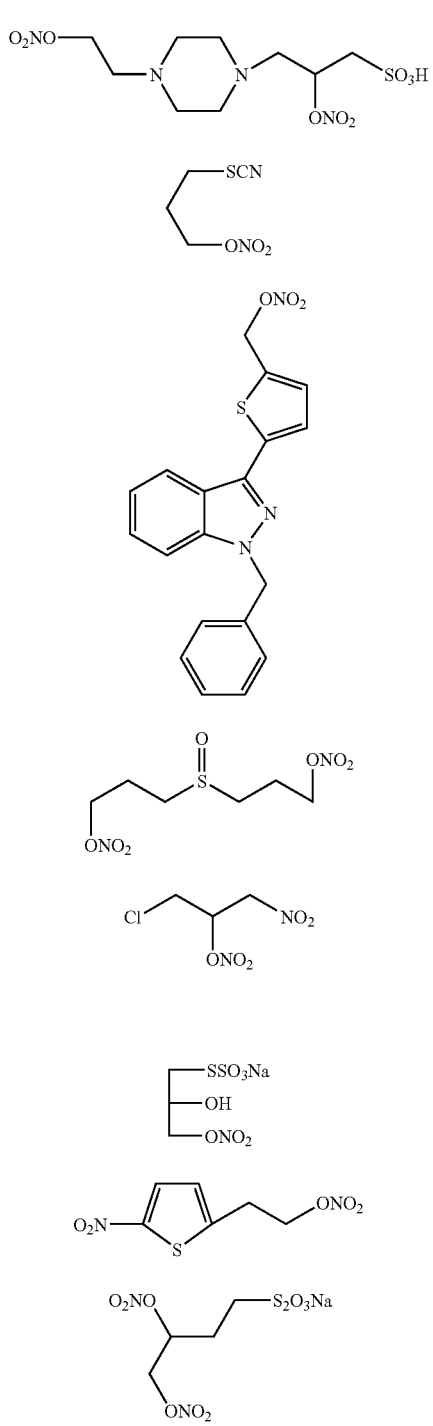

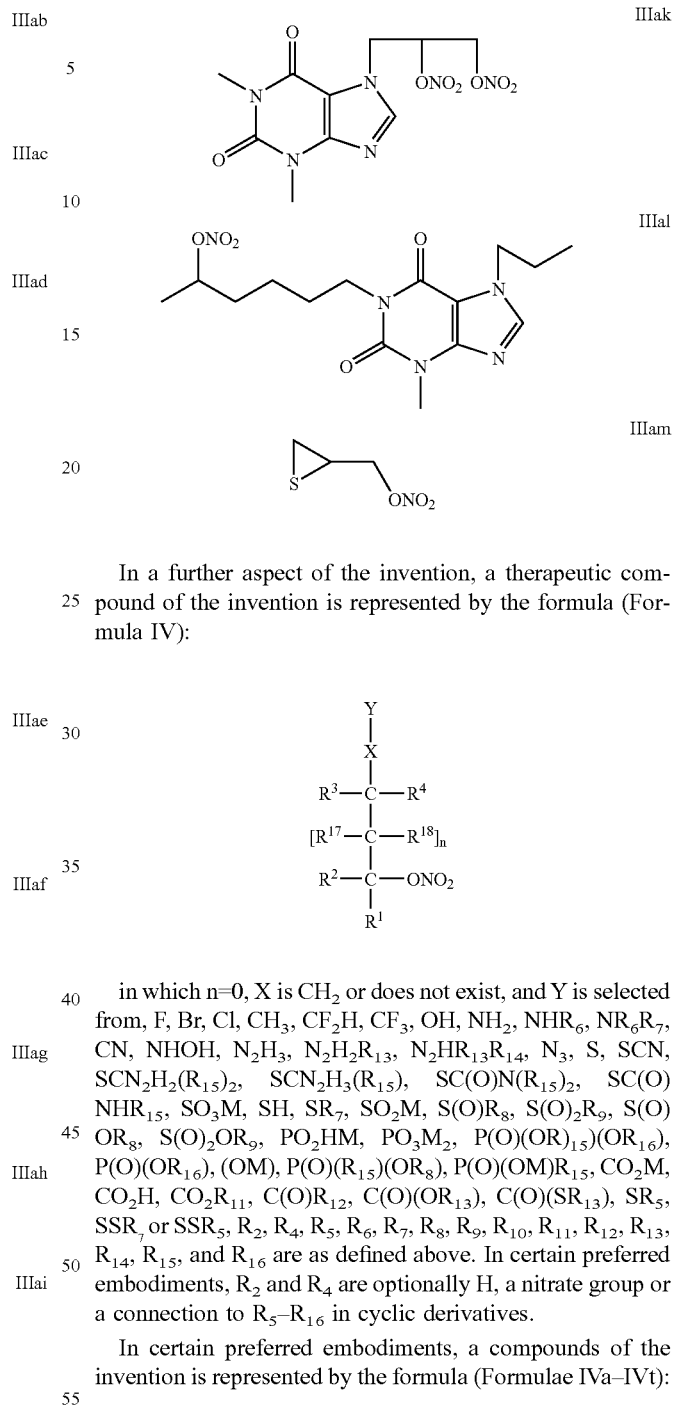

In a further aspect of the invention, a therapeutic compound of the invention is represented by the formula (Formula IV):

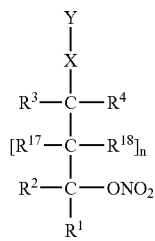

in which n=0, X is $CH_2$ or does not exist, and Y is selected from, F, Br, Cl, $CH_3$, $CF_2H$, $CF_3$, OH, $NH_2$, $NHR_6$, $NR_6R_7$, CN, NHOH, $N_2H_3$, $N_2H_2R_{13}$, $N_2HR_{13}R_{14}$, $N_3$, S, SCN, $SCN_2H_2(R_{15})_2$, $SCN_2H_3(R_{15})$, $SC(O)N(R_{15})_2$, $SC(O)NHR_{15}$, $SO_3M$, SH, $SR_7$, $SO_2M$, $S(O)R_8$, $S(O)_2R_9$, $S(O)OR_8$, $S(O)_2OR_9$, $PO_2HM$, $PO_3M_2$, $P(O)(OR)_{15})(OR_{16})$, $P(O)(OR_{16})$, (OM), $P(O)(R_{15})(OR_8)$, $P(O)(OM)R_{15}$, $CO_2M$, $CO_2H$, $CO_2R_{11}$, $C(O)R_{12}$, $C(O)(OR_{13})$, $C(O)(SR_{13})$, $SR_5$, $SSR_7$ or $SSR_5$, $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are as defined above. In certain preferred embodiments, $R_2$ and $R_4$ are optionally H, a nitrate group or a connection to $R_5$–$R_{16}$ in cyclic derivatives.

In certain preferred embodiments, a compounds of the invention is represented by the formula (Formulae IVa–IVt):

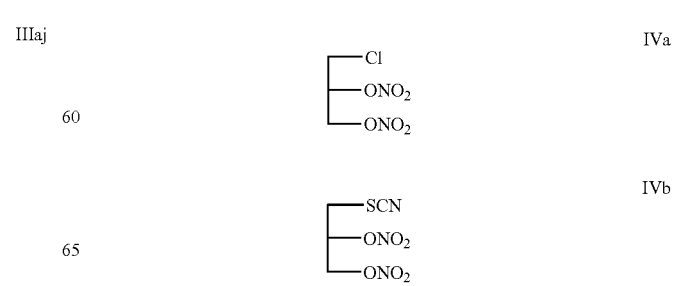

-continued

IVc 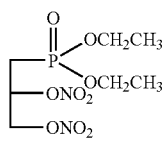

IVd 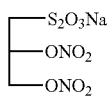

IVe 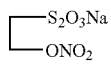

IVf 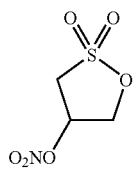

IVg 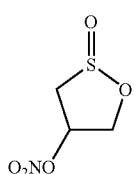

IVh 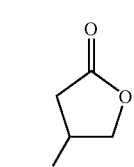

IVi 

IVj 

IVk 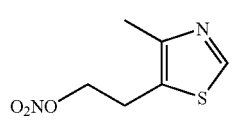

IVl 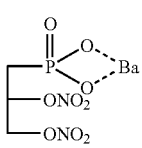

IVm 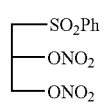

IVn 

-continued

IVo 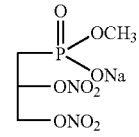

IVp 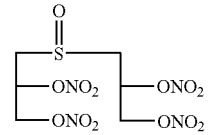

IVq 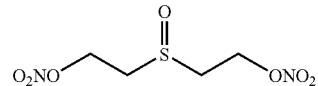

IVr 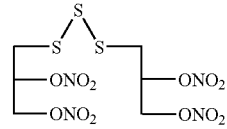

IVs 

IVt 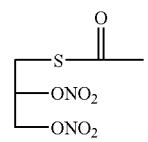

In a further aspect of the invention, compounds according to the invention are represented by the formula (Formula V):

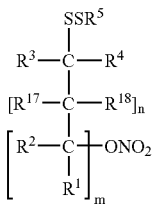

in which $R_2$ is optionally H or a connection to $R_5$ in cyclic derivatives, $R_4$ is H or a nitrate group, and $R_5$ is as described above.

In certain preferred embodiments, compounds of the invention are represented by the formula (Formulae Va–Vag):

Va 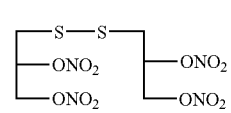

Vb 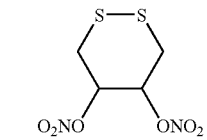

-continued
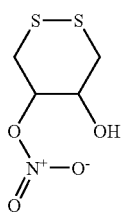
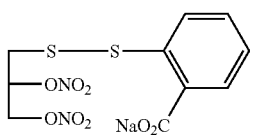 Vd
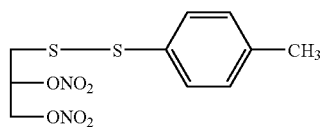 Ve
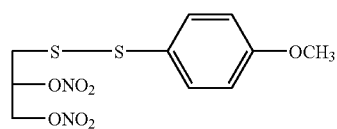 Vf
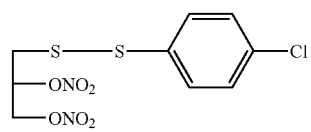 Vg
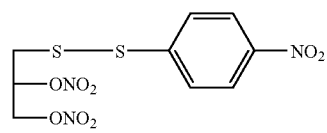 Vh
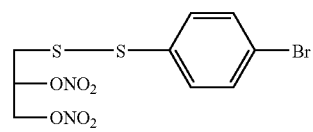 Vi
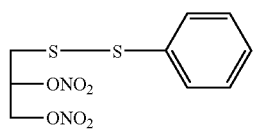 Vj
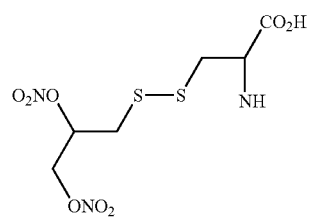 Vk
-continued
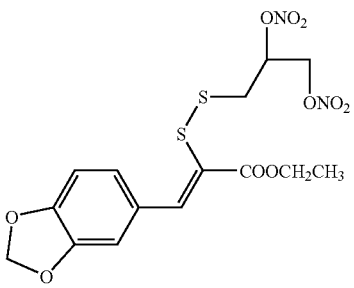 Vc
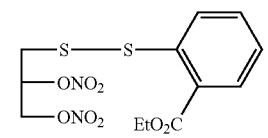 Vm
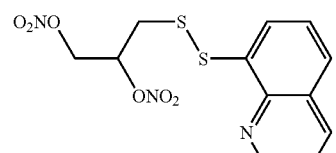 Vn
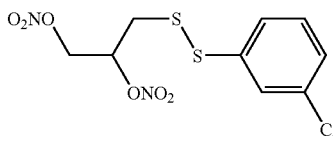 Vo
Vp
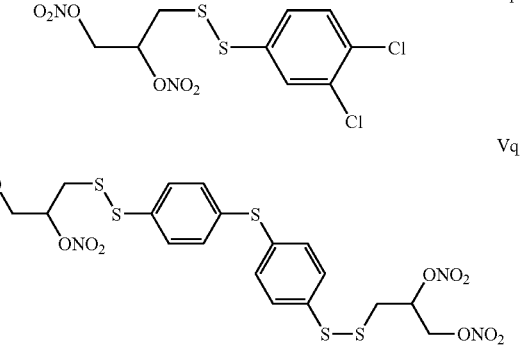 Vq
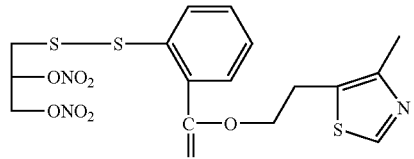 Vr
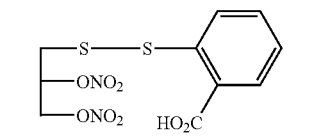 Vs
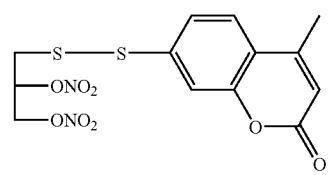 Vt

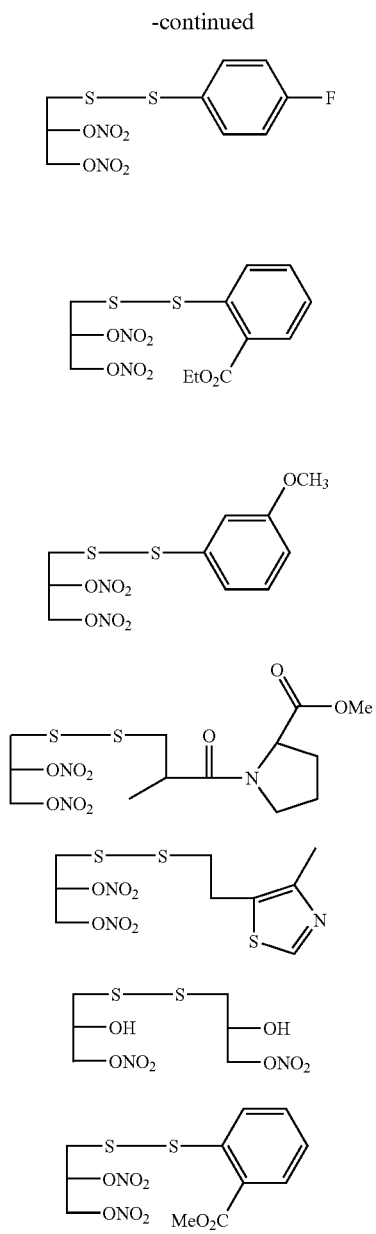

In another aspect, the invention provides novel compounds which can be represented by structures of Formula III, Formula IV, and Formula V. Table 1 lists data associated with these compounds using art-recognized characterization techniques. Further, the invention provides novel pharmaceutical compositions comprising a therapeutic compound (nitrate ester) of the invention and a pharmaceutically acceptable vehicle.

TABLE 1

|   | $^1$H NMR | $^{13}$C NMR |
|---|---|---|
| IIIa | (CDCl$_3$): 5.34–5.57(1H, dm, $^3$J$_{HF}$ 20.6), 4.53–4.87(4H, superposition several multiplets, O$_2$NO—CH$_2$ + CH$_2$F, $^2$J$_{HF}$ 46.7, $^2$J$_{HF}$ 0.66) | (CDCl$_3$): 79.47(d, $^1$J$_{CF}$ 177), 76.73(d, $^2$J$_{CF}$ 20.6), 67.84(d, $^3$J$_{CF}$ 6.87) |
| IIIc | (CDCl$_3$): δ5.7(1H, t, $^2$J$_{HF}$ 54), 5.45(1H, m), 4.5–4.9(2H, m), 4.15–4.35 (1H, m) | (CDCl$_3$): δ75.55, 68.05, 60.76 |
| IIId | (CDCl$_3$): δ5.46(1H, m), 4.80–4.87(1H, dd, J 3.5, 12.9), 4.65–4.72(1H, dd, J 6.2, 12.9), 3.7–3.8(2H, m) | (CDCl$_3$): δ77.24, 68.57, 39.86 |
| IIIf | (CDCl$_3$) δ8.72(s, 1H), 5.38(t, 1H), 4.6(d, 2H), 2.45(s, 3H) | — |
| IIIg | (DMSOd$_6$) CHONO$_2$ only: δ4.8–5.8 | (DMSOd$_6$) CONO$_2$ only: δ85.68, 84.17, 82.47, 76.50 |
| IIIh | (CD$_3$OD) δ4.85(3H, m), 3.5(1H, m) | (CD$_3$OD) δ70.61, 36.74 |
| IIIi | (CDCl$_3$): δ6.95(dd, 1H), 6.71(dd, 1H), 6.09(m, 1H), 3.80(dd, 1H), 3.32(dd, 1H) | (CDCl$_3$): δ137.9, 132.5, 76.6, 52.9 |
| IIIj | (CDCl$_3$): δ5.62(2H, m), 3.60(4H, m) | (CDCl$_3$): δ77.87, 25.22 |
| IIIk | (CD$_3$CN): δ3.45(m, 2H), 5.72(m, 2H) | (CD$_3$CN): δ79.98, 28.87 |

TABLE 1-continued

| | ¹H NMR | ¹³C NMR |
|---|---|---|
| IIIl | — | (CD₃CN): δ79.48, 33.45, 28.47 |
| IIIm | (DMSOd₆): δ5.97(m, 2H), 3.80(m, 4H) | (DMSOd₆): δ78.84, 52.60 |
| IIIn | (CDCl₃): δ5.73(m, 1H), 4.62(m, 1H), 3.96–3.77(m, (m, 1H), 3.58–3.32(m, 1H) | (CDCl₃): δ81.47, 57.85, 53.50, 38.75 |
| IIIo | — | (CDCl₃): δ81.24, 69.79, 33.26, 27.24 |
| IIIp | (CDCl₃): δ5.36(m, 1H), 3.11–3.60(m, 4H), 2.33(m, 2H) | (CDCl₃): δ78.92, 33.66, 30.64, 27.36 |
| IIIq | (CDCl₃): δ5.47(m, 1H), 3.53–3.05(m, 4H), 2.29(m, 2H) | (CDCl₃): δ81.32, 37.12, 32.97, 30.98 |
| IIIw ³¹P(CDCl₃, 162MHz) 24.60 | (CDCl₃, 300MHz): 5.31–5.45(m, 1H), 3.92–4.08(m, 4H), 3.63–3.81(m, 2H), 2.03–2.30(m, 2H), 1.16–1.24(superposition of 2t, 6H, J 7) | (CDCl₃, 75MHz): 76.83, 62.15(d, J 6.37), 43.77(d, J 8.95), 27.08(d, J 142.00), 15.99(d, J 5.88) |
| IIIx ³¹P (CD₃OD, 122MHz) 17.62 | (CD₃OD, 300MHz): 5.38–5.63(m, 1H), 3.75–4.25(superposition of 2m, 4H), 1.88–2.20(m, 2H), 1.12–1.28(t, 3H) | (CD₃, OD 75MHz): 81.14, 61.17(d, J 5.41), 45.56(d, J 5.94), 29.35(d, J 131.74), 17.00(d, J 6.75) |
| IIIak | ¹H(CD₃CN, 300MHz): 7.8(s, 1H), 5.75–5.85(m, 1H), 4.90–4.97(dd, 1H, J 12.87, 3.39), 4.54–4.76(m, 3H), 3.46(s, 3H), 3.27(s, 3H) | ¹³C(CD₃CN, 75MHz)(for polynitrated chain): 78.51, 70.58, 46.01, 30.10, 28.18 |
| Ivi | (CDCl₃): δ5.45(1H, m), 4.83(1H, dd), 4.65(1H, dd), 2.9(2H, m) | (CD₃OD): δ116.44, 75.37, 71.20, 19.19 |
| Ivk | (CDCl₃) δ8.55(s, 1H), 4.55(t, 2H), 3.15(t, 2H), 2.37(s, 3H) | (CDCl₃) δ150.9, 150.7, 125.3, 72.53, 24.47, 15.18 |
| Ivm | (CDCl₃): δ7.5–8.0(arom, 5H), 5.7(1H, m), 4.94(1H, dd), 4.62(1H, dd), 3.5(2H, m) | (CDCl₃): δ135.45, 134.79, 129.81, 27.95, 73.08, 70.04, 54.73 |
| Ivs | 1H-NMR(CDCl₃, 300MHz): 5.23–5.32(1H, m), 4.87(1H, dd, J 12.82, 3.22), 4.68(1H, dd, J 12.83, 6.09), 2.77–2.94(2H, m), 1.66(1H, t, J 9.07) | ¹³C-NMR: (CDCl₃, 75.48MHz): 79.39, 69.30, 23.68 |
| Ivt | 1H-NMR(CDCl3, 300MHz): 5.29–5.38(1H, m), 4.76(1H, dd, J 12.94, 3.11), 4.55(1H, dd, J 12.94, 6.37), 3.30(1H, dd, J 14.06, 5.98), 3.13(1H, dd, J 14.61, 6.35) | 13C-NMR:(CDCl3, 75.48MHz): 194.10, 77.00, 69.79, 30.42, 27.78 |
| Vb | (CDCl₃) δ5.56(m, 2H), 3.38–2.95(m, 4H) | (CD₃OD) δ85.93, 32.77 |
| Vc | (CDCl₃): δ5.85–5.91(1H, m), 4.50–4.58(1H, m), 3.22–3.29(1H, dd, J 5.47, 12.78), 2.97–3.05(1H, dd, J 4.6, 11.88), 2.82–2.90(1H, dd, J 2.87, 12.78), 2.74–2.83(1H, dd, J 3.15, 11.9) | (CDCl₃): δ87.6, 74.96, 36.20, 31.54 |
| Ve | (CDCl₃): δ7.44–7.51(m, arom 2H), 7.17–7.24(d, arom 2H, J 7.91), 5.47–5.59(m, 1H), 4.83–4.93(dd, 1H, J 12.81, 2.78), 4.57–4.67(dd, 1H, J 12.82, 5.71), 3.02–3.12(dd, 1H, J 14.48, 6.01), 2.9–2.99(dd, 1H, J 14.47, 7.72), 2.38(s, 3H) | (CDCl₃): δ21.53, 36.78, 69.82, 77.68, 130.52, 130.62, 132.55, 139.23 |
| Vf | (CDCl₃): δ7.48–7.57(m, arom 2H), 7.48–7.57(m, arom 2H), 5.49–5.59(m, 1H), 4.84–4.93(dd, 1H, J 12.79, 2.79), 4.58–4.68(dd, 1H, J 12.79, 5.75), 3.84(s, 3H), 3.02–3.12(dd, 1H, J 14.47, 5.8), 2.89–2.99(dd, 1H, J 14.46, 7.99). | (CDCl₃): δ36.57, 55.87, 69.75, 77.76, 115.47, 126.71, 133.76, 160.94. |
| Vg | (CDCl₃): δ7.47–7.54(m, arom 2H), 7.32–7.38(m, arom 2H), 5.45–5.55(m, 1H), 4.84–4.97(dd, 1H, J 12.86, 2.92), 4.58–4.68(dd, 1H, J 12.86, 5.68), 2.91–3.11(m, 2H). | (CDCl₃): δ36.87, 69.80, 77.5, 129.98, 130.85, 134.51, 134.79. |
| Vh | (CDCl₃): δ8.21–8.27(m, arom 2H), 7.67–7.74(m, arom 2H), 5.44–5.54(m, 1H), 4.86–4.94(dd, 1H, J 12.92, 3.11), 4.61–4.70(dd, 1H, J 12.92, 5.56), 3.01–3.16(m, 2H). | (CDCl₃): δ37.24, 69.75, 77.41, 124.82, 127.26, 144.83 |
| Vi | (CDCl₃): δ7.40–7.55(m, arom 4H), 5.44–5.55(m, 1H), 4.85–4.92(dd, 1H, J 12.87, 2.91), 4.60–4.70(dd, 1H, J 12.86, 5.66), 2.92–3.11(m, 2H). | (CDCl₃): δ36.87, 69.79, 77.48, 122.72, 130.93, 132.90, 135.15. |
| Vj | (CDCl₃): δ7.55–7.62(d, arom 2H, J 7.16), 7.29–7.44(m, arom 3H), 5.46–5.58(m, 1H), 4.82–4.92(dd, 1H, J 12.85, 2.79), 4.57–4.67(dd, 1H, J 12.86, 5.67), 3.01–3.13(dd, 1H, J 14.51, 6.24), 2.92–3.02(dd, 1H, J 14.52, 7.4) | (CDCl₃): δ36.97, 69.88, 77.61, 128.60, 129.50, 129.85, 136.02 |
| Vk | (CDCl3, 300MHz): 8.09(1H, dd, J 8.12, 0.36), 8.02(1H, dd, J 7.8, 1.15), 7.51–7.59(1H, m, J 7.24, 1.44), 7.21–7.29(1H, m, J 7.35, 0.54), 5.40–5.49(1H, m), 4.70–4.78(1H, dd, J 13.04, 2.95), 4.33–4.45(3H, m, superposition of 1H from CH2—ONO2 and quartet from O—CH2—CH3), 2.66–2.87(2H, quartet, J 6.92), 1.39(3H, t, J 7.14) | (CDCl3, 75.48MHz): 166.21, 140.41, 132.78, 131.46, 127.63, 125.48, 77.25, 71.03, 61.42, 32.51, 28.29, 14.17 |
| Vl | (CDCl₃, 300MHz): δ7.97(s, 1H), 7.48–7.51(d, 1H), 7.17–7.22(m, 1H), 6.84–6.89(d, 1H), 6.05(s, 2H), 5.48–5.58(m, 1H), 4.81–4.89(dd, 1H), 4.53–4.61(dd, 1H), 4.25–4.4(m, 2H), 3.05–3.10(m, 2H), 1.35–1.45(t, 3H). | (CDCl₃, 75.48MHz): δ14.17, 36.27, 62.15, 69.71, 76.57, 101.77, 108.27, 110.31, 125.20, 127.55, 127.87, 146.87, 147.811, 149.76, 165.89 |
| Vm | (CDCl₃, 300MHz): δ8.04–8.11(m, arom 2H), | (CDCl₃, 75.48MHz): δ14.17, 26.23, 35.95, |

TABLE 1-continued

|    | ¹H NMR | ¹³C NMR |
|----|--------|---------|
|    | 7.55–7.62(m, arom 1H), 7.30–7.34(m, arom 1H), 5.43–5.54(m, 1H), 4.88–4.97(dd, 1H, J 12.95, 2.79), 4.62–4.71(dd, 1H, J 12.94, 5.35), 4.45–4.39(q, 2H, J 7.12), 2.92–3.08(m, 2H), 1.39–1.47(t, 3H J 7.13) | 61.55, 69.54, 77.24, 125.56, 125.92, 127.91, 131.52, 132.93, 139.56, 166.189 |
| Vn | (CDCl₃, 300MHz): δ8.92–8.97(m, arom 1H), 8.07–8.23(m, arom 2H), 7.46–7.77(m, arom 3H), 5.53–5.62(m, 1H), 4.91–4.99(dd, 1H, J 12.98, 2.77), 4.61–4.7(dd, 1H, J 12.98, 5.35), 3–3.18(m, 2H) | (CDCl₃, 75.48MHz): δ36.06, 69.62, 70.24, 77.42, 121.97, 125.65, 126.43, 126.70, 128.52, 135.31, 136.37, 145.62, 149.65 |
| Vo | (CDCl₃, 300MHz): δ7.55–7.59(m, arom 1H), 7.40–7.45(m, arom 1H), 7.25–7.36(m, arom 2H), 5.45–5.55(m, 1H), 4.85–4.95(dd, 1H, J 12.98, 3), 4.59–4.69(dd, 1H, J 12.89, 6.67), 2.95–3.12(m, 2H) | (CDCl₃, 75.48MHz): δ37.10, 69.87, 77.44, 126.80, 128.38, 128.52, 130.83, 135.76, 138.01 |
| Vp | (CDCl₃, 300MHz): δ7.65–7.67(d, arom 1H J 2.15), 7.44–7.47(d, arom 1H J 7.42), 7.28–7.49(m, arom 1H), 5.46–5.54(m, 1H), 4.87–4.94(dd, 1H, J 12.89, 2.99), 4.61–4.68(dd, 1H, J 12.88, 5.65), 2.95–3.12(m, 2H) | (CDCl3 75.48MHz): δ36.59, 69.32, 76.90, 127.49, 129.86, 131.04, 132.31, 133.59, 135.65 |
| Vq | (CDCl₃, 300MHz): δ7.2–7.6(m, arom 8H), 5.42–5.56(m, 2H), 4.82–4.95(dd, 2H), 4.55–4.67(dd, 2H), 2.93–3.15(m, 4H) | |
| Vr | (CDCl3, 300MHz): δ8.63(s, arom 1H), 8.01–8.13(m, arom 2H), 7.57–7.65(m arom 1H), 7.26–7.37(m, arom 1H), 5.42–5.51(m, 1H), 4.88–4.97(dd, 1H, J 12.9, 2.7), 4.62–4.71(dd, 2H, J 12.9, 5.1), 4.49–4.57(t, 2H, J 6.6), 3.23–3.32(t, 2H, J 6.6), 2.91–3.08(m, 2H), 2.45(s, 3H) | |
| Vs | (d₆-acetone), 300MHz): 8.16–8.23(1H, d, J 7.72), 8.07–8.13(1H, dd, J 7.72, 1.11), 7.63–7.72(1H, m, J 8.38, 1.26), 7.33–7.42(1H, m, J 7.33), 5.67–5.76(1H, m), 5.09–5.17(1H, dd, J 12.91, 2.68), 4.83–4.93(1H, dd, J 12.91, 5.91), 3.18–3.32(2H, m) | (d₆-acetone, 100.62MHz): 167.74, 134.01, 132.64, 126.62, 126.21, 78.90, 71.69, 36.79 |
| Vt | (CDCl₃, 300MHz): δ7.53–7.59(d, arom 1H, J 8.35), 7.46–7.49(d, arom 1H, J 1.82), 7.37–7.43(m, arom 1H), 6.24(s, 1H), 5.46–5.55(m, 1H), 4.86–4.94(dd, 1H, 12.92, 2.92), 4.61–4.69(dd, 1H, J 12.93, 5.75), 3.0–3.15(m, 2H), 2.42(s, 3H) | (CDCl₃, 75.48MHz): δ19.01, 37.10, 70.01, 77.46, 115.27, 115.34, 119.52, 123.07, 125.83, 141.13, 152.38, 154.25, 160.51 |
| Vu | (CDCl₃, 300MHz): δ7.55–7.58(m, arom 1H), 7.40–7.45(m, arom 1H), 7.27–7.32(m, arom 2H), 5.46–5.54(m, 1H), 4.86–4.94(dd, 1H, J 12.88, 2.92), 4.59–4.68(dd, 1H, J 12.88, 5.65), 2.95–3.13(m, 2H) | (CDCl3, 75.48MHz): δ37.08, 69.83, 77.40, 126.80, 128.40, 128.54, 130.83, 135.78, 137.98 |
| Vv | (CDCl₃, 300MHz): 8.09–8.14(1H, d, J 8.15), 7.98–8.04(1H, dd, J 7.75, 0.91), 7.52–7.59(1H, m, J 8.22, 1.19), 7.22–7.28(1H, m, J 7.65), 4.53–4.61(1H, dd, J 11.33, 3.63), 4.42–4.50(1H, m, J 11.33, 6.27), 4.32–4.41(2H, qu., J 7.13), 4.16–4.25(1H, m), 2.74–2.84(2H, m), 2.55–2.73(1H, br.s.), 1.34–1.42(3H, t, J 7.13) | (CDCl₃, 75.48MHz): 166.34, 140.25, 132.90, 131.49, 127.67, 125.60, 74.34, 66.83, 61.53, 40.89, 14.20 |
| Vx | (CDCl₃, 300MHz): δ5.49–5.61(m, 1H), 4.88–4.90(m, 1H), 4.62–4.74(m, 1H), 4.40–4.55(m, 1H), 3.59–3.78(m, superpos. 5H), 2.69–3.21(m, superpos. 5H), 2.14–2.29(m, 1H), 1.90–2.12(m, 3H), 1.22–1.28(d, 3H) | (CDCl₃, 75.48MHz): δ17.39, 25.20, 29.40, 36.41/36.51, 38.55, 41.94/42.19, 47.32, 52.56, 59.12, 69.90/70.29, 77.89/78.00, 173.01, 173.48 |
| Vy | (CDCl₃, 300MHz): δ8.5(s, 1H), 2.94–3.02(t, 2H), 2.62–2.72(q, 2H), 2.33(s, 3H), 1.38–1.45(t, 1H). | (CDCl₃, 75.48MHz): δ15.41, 26.41, 31.51, 39.72, 129.36, 149.90 |
| Vz | (CD₃CN, 300MHz): 4.60–4.68(1H, dd, J 11.44, 3.36), 4.43–4.52(1H, dd, J 11.35, 6.97), 4.11–4.21(1H, m), 2.80–3.00(2H, m) | (CD₃CN, 75.48MHz): 76.33, 67.34, 42.74 |
| Vaa | (CDCl₃, 300MHz): δ8.05–8.15(m, arom 2H), 7.55–7.65(m, arom 1H), 7.25–7.35(m, arom 1H), 5.40–5.55(m, 1H), 4.85–4.95(dd, 1H), 4.60–4.70(dd, 1H), 3.95(s, 3H), 2.90–3.10(m, 2H) | (CDCl₃, 5.48MHz): δ36.42, 52.87, 69.98, 77.69, 126.07, 126.45, 128.01, 132.06, 133.53, 140.161, 167.10 |
| Vab | (CDCl₃, 300MHz): δ7.30–7.39(m, arom 5H), 5.28–5.37(m, 1H), 4.72–4.78(dd, 1H, J 12.86, 2.79), 4.45–4.53(dd, 1H, J 12.86, 5.9), 3.95(s, 2H), 2.44–2.52(dd, 1H, J 14.38, 6.1), 2.33–2.42(dd, 1H, J 14.38, 7.34) | (CDCl₃, 75.48MHz): δ32.01, 35.997, 43.66, 69.89, 77.72, 128.33, 129.22, 129.81, 137.22 |
| Vac | 1H-NMR(CDCl3, 300MHz): 5.48–5.58(1H, m), 4.89(1H, ddd, J 12.91, 2.91, 1.21), 4.56–4.70(2H, m), 4.48(1H, dd, J 11.41, 6.4), 4.16–4.26(1H, m), 2.94–3.12(2H, m), 2.81–2.91(2H, m) | 13C-NMR:(CDCl3, 75.48MHz): 77.30, 74.22, 69.46, 69.38, 66.90, 66.78, 42.12, 41.99, 36.82, 36.59 |
| Vad | (CDCl₃, 400MHz): 5.55–5.65(m, 1H), 4.87–4.94(dd, 1H, J 12.94, 2.94), 4.62–4.70(m, 1H, J 12.88), 3.13–3.30(m, 2H) | (CDCl₃, 400MHz): 76.74, 69.46/69.42, 36.65/36.63 |

It will be noted that the structure of some of the compounds of this invention include asymmetric carbon atoms. It is to be understood accordingly that the isomers (e.g., enantiomers, diastereomers) arising from such asymmetry are included within the scope of this invention. Such isomers can be obtained in substantially pure form by classical separation techniques and by asymmetric synthesis (for example, see below in Example 21). Unless expressly noted to the contrary, compounds referred to herein shall be construed to include both the R and S stereoisomers at each stereogenic centre.

In certain embodiments, a therapeutic compound of the invention comprises a cation (i.e., in certain embodiments, one of X or Y includes a cation, e.g., in the compound of formula IVd). If the cationic group is a proton, then the compound is considered an acid. If the proton is replaced by a metal ion or its equivalent, the compound is a salt. Pharmaceutically acceptable salts of the therapeutic compound are within the scope of the invention. For example, M can be a pharmaceutically acceptable alkali metal (e.g., Li, Na, K), ammonium, alkaline earth metal (e.g., Ca, Ba, Mg), higher valency cation, or polycationic counter ion (e.g., polyammonium cation) (see e.g., Berge et al. (1977)). It will be appreciated that the stoichiometry of an anionic portion of the compound to a salt-forming cation will vary depending on the charge of the anionic portion of the compound and the charge of the counterion. Preferred pharmaceutically acceptable salts include a sodium, potassium, or calcium salt, but other salts are also contemplated within their pharmaceutically acceptable range.

Therapeutic compounds of the invention can be administered in a pharmaceutically acceptable vehicle. As used herein "pharmaceutically acceptable vehicle" includes any and all solvents, excipients, dispersion media, coatings, antibacterial and antifungal agents, isotonic and absorption delaying agents, and the like which are compatible with the activity of the compound and are physiologically acceptable to the subject. An example of a pharmaceutically acceptable vehicle is buffered normal saline (0.15 M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

Carrier or substituent moieties useful in the present invention may also include moieties which allow a therapeutic compound to be selectively delivered to a target organ. For example, delivery of a therapeutic compound to the brain may be enhanced by a carrier moiety using either active or passive transport (a "targeting moiety"). Illustratively, the carrier molecule may be a redox moiety, as described in, for example, U.S. Pat. Nos. 4,540,654 and 5,389,623, both to Bodor. These patents disclose drugs linked to dihydropyridine moieties which can enter the brain, where they are oxidized to a charged pyridinium species which is trapped in the brain. Thus drugs accumulate in the brain. Other carrier moieties include compounds, such as amino acids or thyroxine, which can be passively or actively transported in vivo. Such a carrier moiety can be metabolically removed in vivo, or can remain intact as part of an active compound. Structural mimics of amino acids (and other actively transported moieties) including peptidomimetics, are also useful in the invention. As used herein, the term "peptidomimetic" is intended to include peptide analogs which serve as appropriate substitutes for peptides in interactions with e.g., receptors and enzymes. The peptidomimetic must possess not only affinity, but also efficacy and substrate function. That is, a peptidomimetic exhibits functions of a peptide, without restriction of structure to amino acid constituents. Peptidomimetics, methods for their preparation and use are described in Morgan et al., (1989) "Approaches to the discovery of non-peptide ligands for peptide receptors and peptidases". *In Annual Reports in Medicinal Chemistry* (Vinick, F. J., ed.) pp. 243–252, Academic Press, San Diego, Calif. Many targeting moieties are known, and include, for example, asialoglycoproteins (see e.g., Wu, U.S. Pat. No. 5,166,320) and other ligands which are transported into cells via receptor-mediated endocytosis (see below for further examples of targeting moieties which may be covalently or non-covalently bound to a target molecule).

In the methods of the invention, pain and/or inflammation in a subject is mitigated by administering an analgesic, sedative or anti-inflammatory therapeutic compound of the invention to the subject. The term "subject" is intended to include living organisms in which pain can occur. Examples of subjects include humans, apes, monkeys, cows, sheep, goats, dogs, cats, mice, rats, and transgenic species thereof. Administration of the compositions of the present invention to a subject to be treated can be carried out using known procedures, at dosages and for periods of time effective to alleviate pain in the subject. An effective amount of the therapeutic compound necessary to achieve a therapeutic effect may vary according to factors such as the subject, the age, sex, and weight of the subject, and the ability of the therapeutic compound to mitigate pain and inflammation in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention (e.g., Va) is between 0.5 and 5000 mg/kg of body weight/per day, preferably between 50 and 1000 mg/kg/day, and still more preferably between 250 and 750 mg/kg/day. In an aqueous composition, preferred concentrations for the active compound (i.e., the therapeutic compound that can mitigate pain) are between 5 and 500 mM, more preferably between 10 and 100 mM, and still more preferably between 20 and 50 mM.

According to the invention, therapeutic compounds are administered to a subject by a route which is effective for mitigating inflammation, effecting analgesia and/or effecting sedation. Suitable routes of administration include but are not limited to sublingual, oral, buccal, transdermal, nasal, subcutaneous, intraocular, intravenous, intramuscular and intraperitoneal (e.g., by injection). Preferred routes of administration are oral and transdermal. The therapeutic compounds can be administered with a pharmaceutically acceptable vehicle. Depending on the route of administration, the active compound may be coated in a material to protect the compound from the action of acids, enzymes and other natural conditions which may inactivate the compound.

Therapeutic compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., Ranade et al., 1989). Exemplary targeting moieties include folate or biotin (see, e.g., U.S. Pat. No. 5,416,016 to Low et al.); mannosides (Umezawa et al., 1988); antibodies (Bloeman et al., 1995; Owais et al., 1995); surfactant protein A receptor (Briscoe et al., 1995). In a preferred embodiment, therapeutic compounds of the invention are formulated in liposomes; in a more preferred embodiment, the liposomes include a targeting moiety.

Delivery and in vivo distribution can also be affected by alteration of an anionic group of compounds of the invention. For example, anionic groups such as phosphonate or carboxylate can be esterified to provide compounds with desirable pharmocokinetic, pharmacodynamic, biodistributive, or other properties. Exemplary compounds include IVl and pharmaceutically acceptable salts or esters thereof.

To administer a therapeutic compound by other than parenteral administration, it may be necessary to coat the compound with, or co-administer the compound with, a material to prevent its inactivation. For example, a therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. (1984) 7, 27).

A therapeutic compound may also be administered parenterally (e.g., intramuscularly, intravenously, intraperitoneally, intraspinally, or intracerebrally). Dispersions can be prepared in glycerol, liquid polyethylene glycols, lactose, dextrose and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, dextrose, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating a therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

A therapeutic compound can be orally administered, for example, with an inert diluent or an assimilable edible carrier. A therapeutic compound and other ingredients may also be enclosed in a hard or soft shell gelatin capsule, compressed into tablets, or incorporated directly into the subject's diet. For oral therapeutic administration, a therapeutic compound may be incorporated with excipients and used in the form of ingestible tablets, buccal tablets, troches, capsules, elixirs, suspensions, syrups, wafers, and the like. The percentage of therapeutic compound in the compositions and preparations may, of course, be varied. The amount of therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of pain and inflammation in subjects, or effecting sedation.

A therapeutic composition can be administered in time-release or depot form, to obtain sustained release of a therapeutic compound over time. A therapeutic compound of the invention can also be administered transdermally (e.g., by providing a therapeutic compound, with a suitable carrier, in patch form, or in an unguent or cream).

Active compounds are administered at a therapeutically effective dosage sufficient to mitigate pain and/or inflammation in a subject. The ability of a compound to mitigate pain or inflammation can be evaluated in model systems that may be predictive of analgesia and anti-inflammation in human diseases, such as animal model systems known in the art (including, e.g., the preclinical acute pain writhing model in the mouse; and the formalin-sensitization model of tissue injury pain in the rat) or by in vitro methods, (including, e.g., the assays described above and below, vide infra). The ability of a compound to effect sedation can be evaluated in model systems that may be predictive of sedation of use in treatment of human diseases, such as animal model systems known in the art (including, e.g., the loss of the righting reflex in the mouse as described, vide infra) or by in vitro methods, (including, e.g., modulation of the activity of $GABA_A$ receptors as described above and below, vide infra).

It will be appreciated that the ability of a compound of the invention to mitigate pain and/or inflammation, in certain embodiments, be evaluated by observation of one or more symptoms or signs associated with pain and inflammation in vivo. Thus, for example, the ability of a compound to alleviate pain may be associated with an observable improvement in a clinical manifestation of the underlying pain or inflammation related disease state or condition, or a slowing or delay in progression of symptoms of the condition. Thus, monitoring of clinical manifestations of disease can be useful in evaluating the analgesic, sedative and anti-inflammatory efficacy of a compound of the invention.

Treating or mitigating pain may involve effecting analgesia, effecting sedation, inhibiting or preventing inflammation, and/or ameliorating the manifestations or impact of pain inducing stimuli. Modulating a biological process such as the biological levels of cGMP or cAMP, or activity of soluble GCase, includes regulating increases and decreases in such activity, and inhibition, potentiation, agonism, or antagonism of the biological process.

Methods of the invention are useful for treating pain and/or inflammation associated with any disease in which pain or inflammation occurs. Clinically, pain and inflammation can be associated with, but not limited to, tissue injury, post-operative tissue injury, nerve injury, post-herpetic neuralgia, phantom limb pain, diabetic neuropathy, arthritis, dysmenorrhea, endometriosis, cancer, chemotherapy, myocardial infarction, cerebral vascular occlusion, or result from surgical procedures.

Certain compounds for use in the methods of the invention are commercially available, whereas others are novel (see hereinbelow and applicants' co-pending application U.S. Ser. No. 09/267,379, filed Mar. 15, 1999 now U.S. Pat. No. 6,310,052). Both types can be synthesized by standard techniques known in the art. In general, nitrate esters can be prepared from the corresponding alcohol, oxirane or alkene by standard methods that include: nitration of alcohols and oxiranes, mixed aqueous/organic solvents using mixtures of nitric and sulfuric acid and/or their salts, with temperature control (see Yang et al., 1996); nitration of alcohols and oxiranes in acetic anhydride using nitric acid or its salts with or without added acid catalyst, with temperature control (see, e.g., Louw, et al., 1976); nitration of an alcohol with a nitronium salt, e.g., a tetrafluoroborate; nitration of an alkene with thallium nitrate in an appropriate solvent (Ouellette et al., 1976). Compounds of the present invention also can be prepared as described below.

The contents of all scientific publications and patent documents cited herein are hereby incorporated herein by reference in their entirety.

The following Examples further illustrate the present invention and are not intended to be limiting in any respect.

EXAMPLES

Example 1

Characterization of Guanylyl Cyclase Activation

Activation of soluble guanylyl cyclase (GCase) by nitrates IIIm, IVa, IVb, IVd, IVe, Ivf, IVg, IVj, Va, Vb, and GTN was assayed employing partially purified enzyme freshly prepared from the 105,000 g supernatant fraction of rat aorta homogenates, using the radioimmunoassay method described by Bennett et al. (1992). Dose-response curves were obtained for GCase activation by nitrates IVa, IVb, UVd, IVe, IVf, IVg, IVj, and GTN in the presence and absence of cysteine and dithiothreitol (DTT; both 2 mM). In all cases, data were normalized to the maximal GTN response carried out in identical GCase preparations. Experimental incubations were performed at 37° C. for 10 min. The data for IVd is summarized in FIG. 1. The GCase assay data show that IVd activates GCase, with a submillimolar EC-50 (effective concentration for 50% of the subjects) in the absence of any added thiol, in contrast to GTN, which requires added cysteine. Compounds IVd also activates GCase in the presence of DTT, in contrast to GTN, which, enigmatically, does not. Relative to GTN itself, a wide range of potency was observed for these novel nitrate esters. No activation of GCase by glycerol mononitrates was observed in this assay at the concentrations of nitrate employed.

Activation of GCase, in vitro, by some of these organic nitrates is via release of NO, since in the presence of cysteine, substantial NO is released at rates which are measurable amperometrically, using the method described by Artz and Thatcher (1998). By comparison, nitroglycerin, which is currently understood by others skilled in the art to act only as an NO-donor therapeutic agent, does not release NO at a rate measurable amperometrically, in the absence nor the presence of cysteine. Relative rates for NO release, at 37° C., pH 7.4, in the presence of cysteine (2 mM) from nitrates Vj, Vu, Vi, Vh, Vg, Vf, and Ve, (1 mM) were 1.0, 1.0, 1.8, 0, 1.2, 0.5, 1.8, respectively. Thus modification of the structure of these organic nitrates can be used to control their NO-releasing ability and also to modulate GCase activity.

Figure 2:
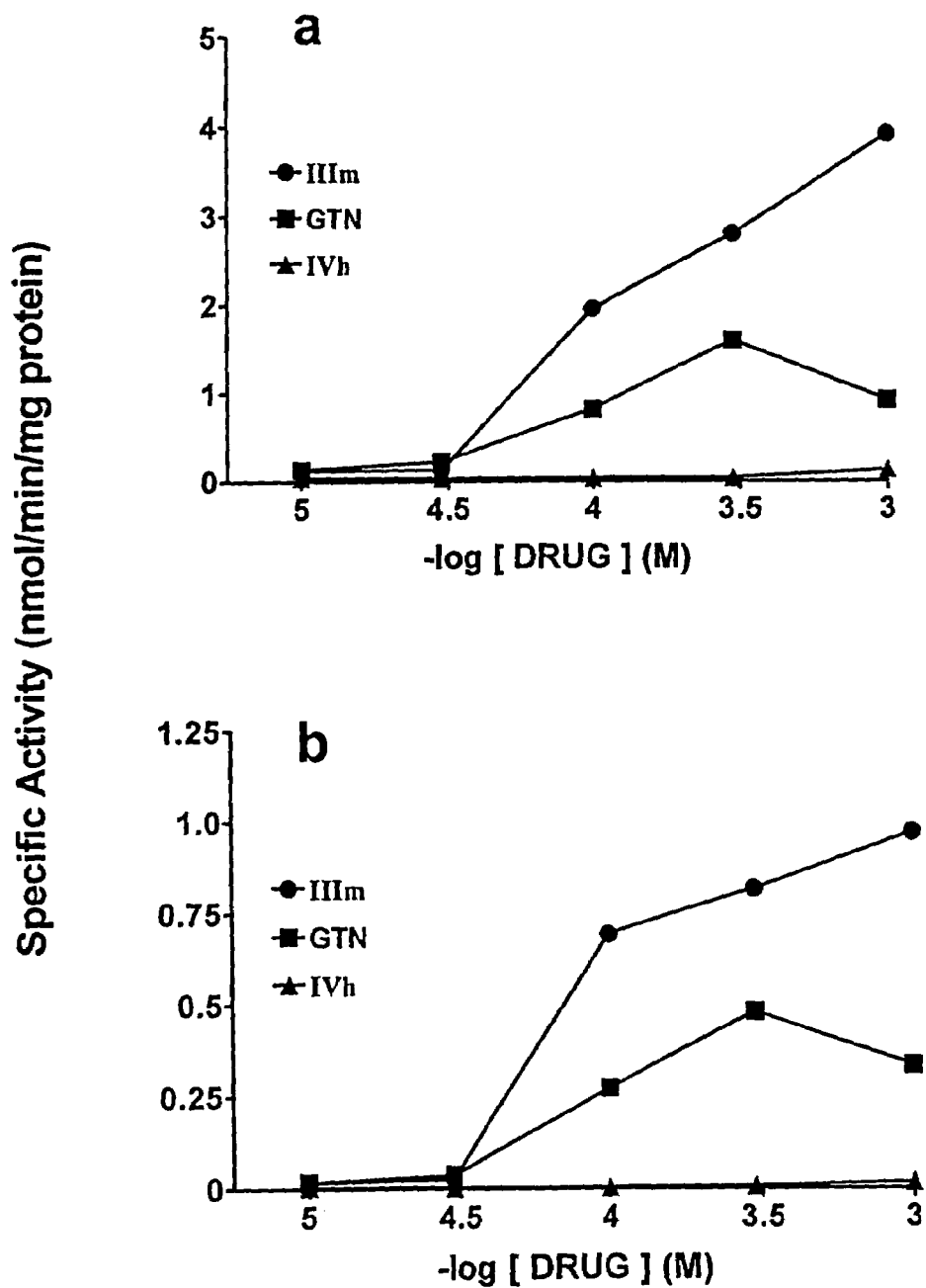
FIG. 2(a–b) is a graph showing the comparison of GTN (squares), IIIm (circles) and IVh (triangles) with added L-cysteine (1 mM) on soluble GCase activity in rat aorta homogenate (a), and rat hippocampus homogenate (b). Data points represent the mean of duplicate determinations carried out in identical GCase preparations.
Figure 3:
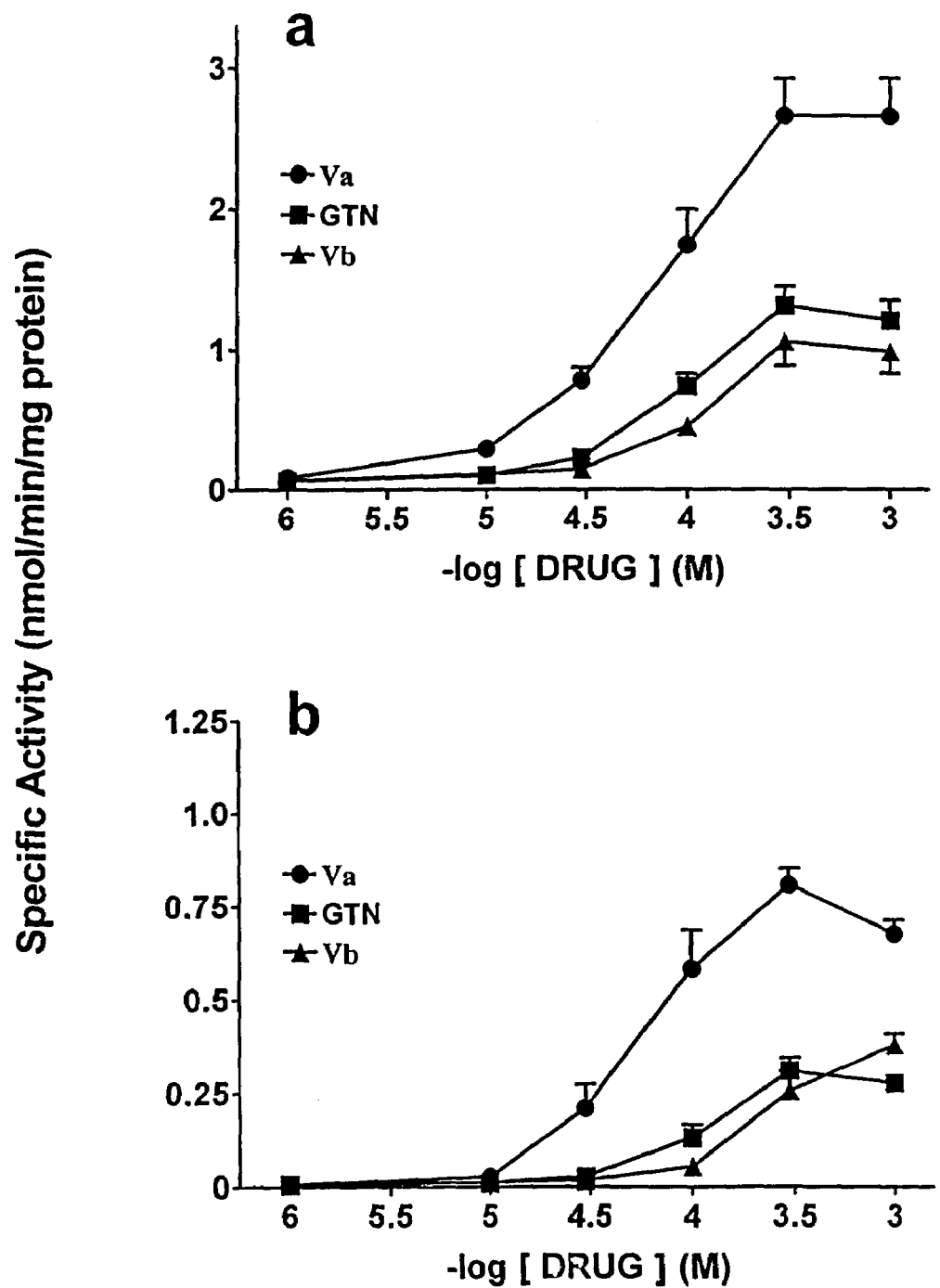
FIG. 3(a–b) is a graph showing the comparison of GTN (squares), Va (circles) and Vb (triangles) with added L-cysteine(1 mM) on soluble GCase activity in rat aorta homogenate homogenate (a), and rat hippocampus homogenate (b). Data points represent the mean±standard errors calculated separately for each point (n=8–11).

To test for potential differences in GCase activation by nitrates, the effects of IIIm, IVh, Va, Vb, and GTN were assayed in brain and vascular tissue. IVh had no effect on GCase activity in either rat aorta or rat hippocampus (FIG. 2). IIIm had greater efficacy to stimulate GCase activity compared to GTN in both rat aorta and rat hippocampus (FIG. 2). Vb was found to be equivalent to GTN in efficacy and potency for activation of GCase in both rat aorta and rat hippocampus (FIG. 3). Va was found to have greater efficacy, but equal potency, to GTN in rat aorta (FIG. 3a). In contrast, Va had greater efficacy and greater potency to stimulate GCase in rat hippocampus (FIG. 3b). These data illustrate that nitrates have differential effects on GCase activation that are dependent on both structure of the compound and the tissue assayed for GCase activity, supporting the notion that effects of nitrates elicited through GCase activation, such as analgesia and vasodilation, are separable and may be regulated in a tissue-specific and/or activity-specific manner, by appropriate choice of organic nitrate.

As further examples of the potential for modulating potency, efficacy and tissue selectivity for activation of GCase, by choice of an appropriate organic nitrate, nitrates Vaa and Vt were assayed in brain and vascular tissue. In the presence (+) and absence (−) of 1 mM cysteine, the potency (EC-50 values) and efficacy (maximal activation) were measured for activation of GCase from rat hippocampus (Table 2).

TABLE 2

|     | 1 mM cysteine | EC-50 (hipp.), M | EC-50 (aorta), M | maximal (hipp.), relative to GTN[a] | maximal (aorta), relative to GTN[a] |
|-----|---------------|------------------|------------------|-------------------------------------|-------------------------------------|
| Vaa | +             | $1.4 \times 10^{-4}$ | $1.8 \times 10^{-4}$ | 5.1 | 2.2 |
| Vaa | −             | $5.7 \times 10^{-5}$ | $1.8 \times 10^{-4}$ | 2.1 | 1.0 |

TABLE 2-continued

|    | 1 mM cysteine | EC-50 (hipp.), M | EC-50 (aorta), M | maximal (hipp.), relative to GTN[a] | maximal (aorta), relative to GTN[a] |
|----|---|---|---|---|---|
| Vt | + | 5.1 × 10⁻⁵ | 6.5 × 10⁻⁵ | 3.0 | 2.3 |
| Vt | − | 1.7 × 10⁻⁵ | 1.8 × 10⁻⁶ | 1.8 | 1.7 |

[a]Normalized to GTN + 1 mM cysteine maximal response.

Example 2

Characterization of Cyclic GMP Accumulation

Figure 4:
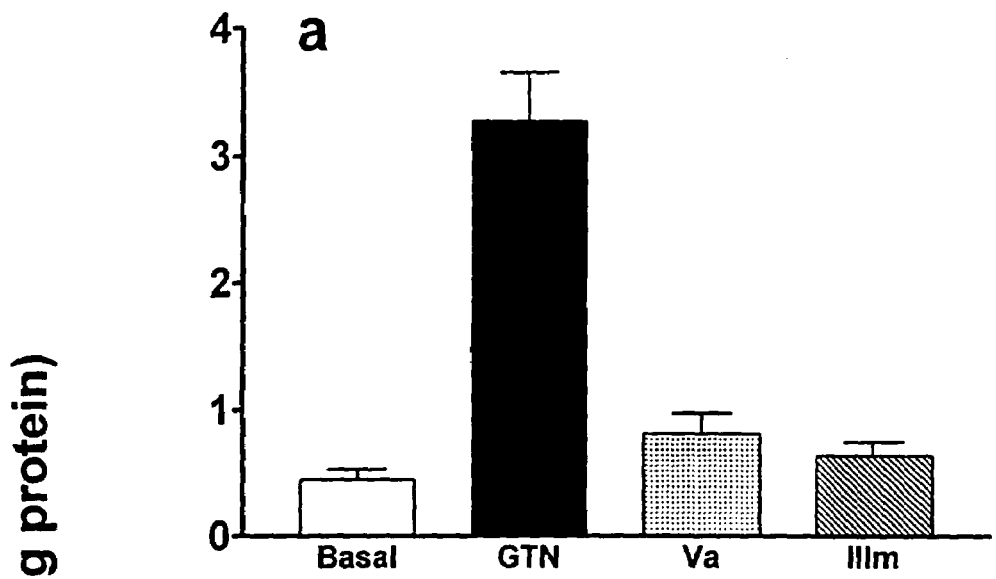
FIG. 4(a–b) is a graph showing the comparison of cyclic GMP accumulation in isolated rat aorta induced by diluent (basal, open bar), GTN (filled bar), Va (stippled bar), or IIIm (hatched bar). Segments of rat aorta were exposed to diluent, 1 µM drug (a), or 10 µM drug (b) for 1 min and cyclic GMP content determined by radioimmunoassay. Data are the mean±standard errors (a, n=8; b, n=5).
Figure 4:
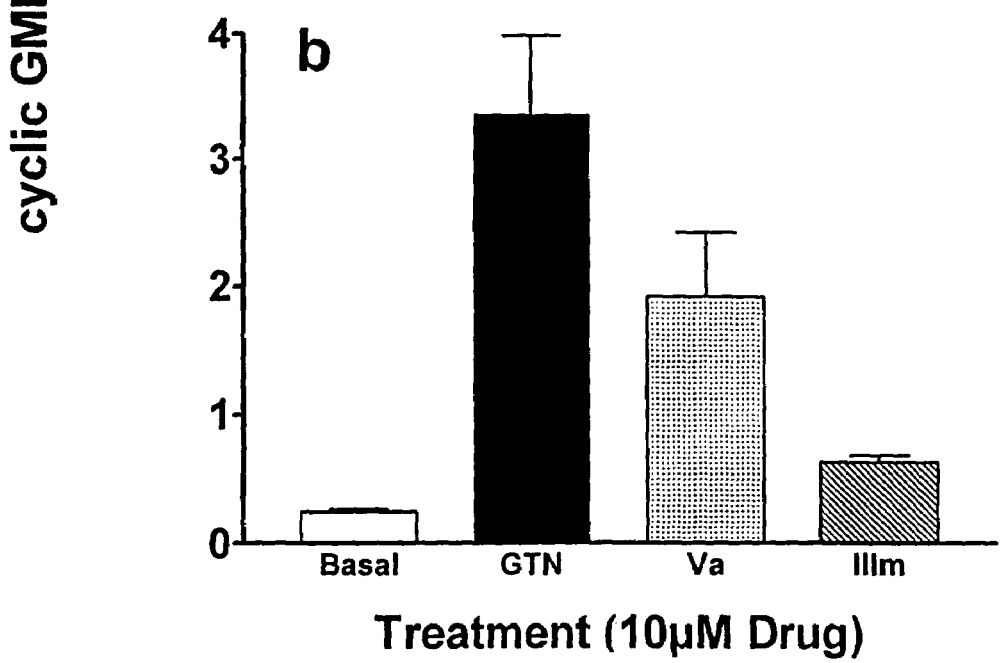
Figure 5:
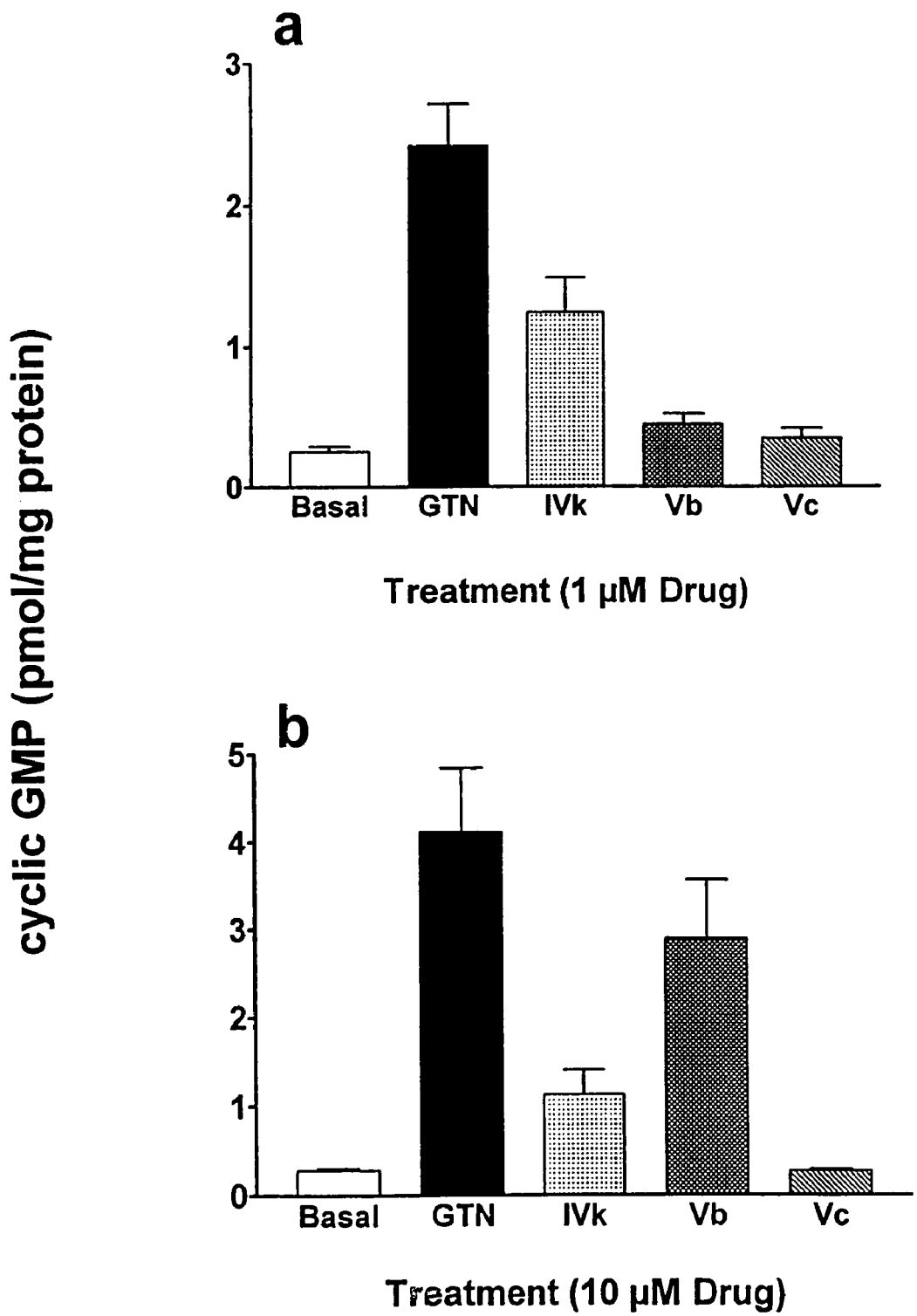
FIG. 5(a–b) is a graph showing the comparison of cyclic GMP accumulation in isolated rat aorta induced by diluent (basal, open bar), GTN (filled bar), IVk (stippled bar), Vb (cross-hatched bar), or Vc (hatched bar). Segments of rat aorta were exposed to diluent, 1 µM drug (a), or 10 µM drug (b) for 1 min and cyclic GMP content determined by radioimmunoassay. Data are the mean±standard errors (a, n=5; b, n=4).

In order to extend the GCase data further, the effects of nitrates Va, IIIm, Vb, Vc, and IVk on cyclic GMP accumulation in intact isolated rat aorta were examined (FIGS. 4, 5). Thoracic aortic strips were prepared from male Sprague-Dawley rats (Charles-River, Canada) as described in McGuire et al. (1994) and Stewart et al. (1989). Tissues were contracted submaximally with phenylephrine (0.1 μM) and exposed to various concentrations of drug for 1 min. Cyclic GMP accumulation was determined using the radioimmunoassay method described by Bennett et al. (1992). At concentrations of 1 μM and 10 μM, GTN and IVk significantly increased cGMP accumulation (FIG. 5). At a concentration of 1 μM, Va, IIIm, Vb, and Vc did not significantly increase cyclic GMP accumulation (FIGS. 4a, 5a). At a concentration of 10 μM, Va, Vb, and IVk significantly increased cyclic GMP accumulation whereas IIIm and Vc did not (FIGS. 4b, 5b).

Figure 6:
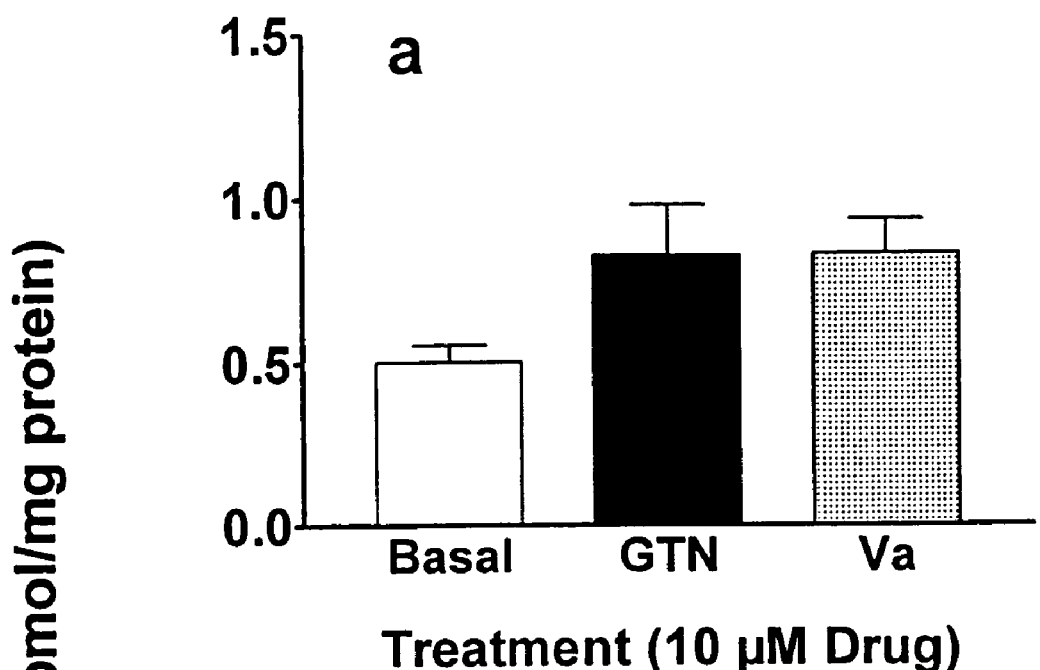
FIG. 6(a–b) is a graph showing cyclic GMP accumulation in rat hippocampal slices induced by diluent (basal, open bar), GTN (filled bar), and Va (stippled bar). Sections of rat hippocampus (400 μm) were prepared and exposed to diluent, 10 μM drug (a) or 100 μM drug (b) for 3 min and cyclic GMP content determined by radioimmunoassay. Data are the mean±standard errors (a, n=4; b, n=5).
Figure 6:
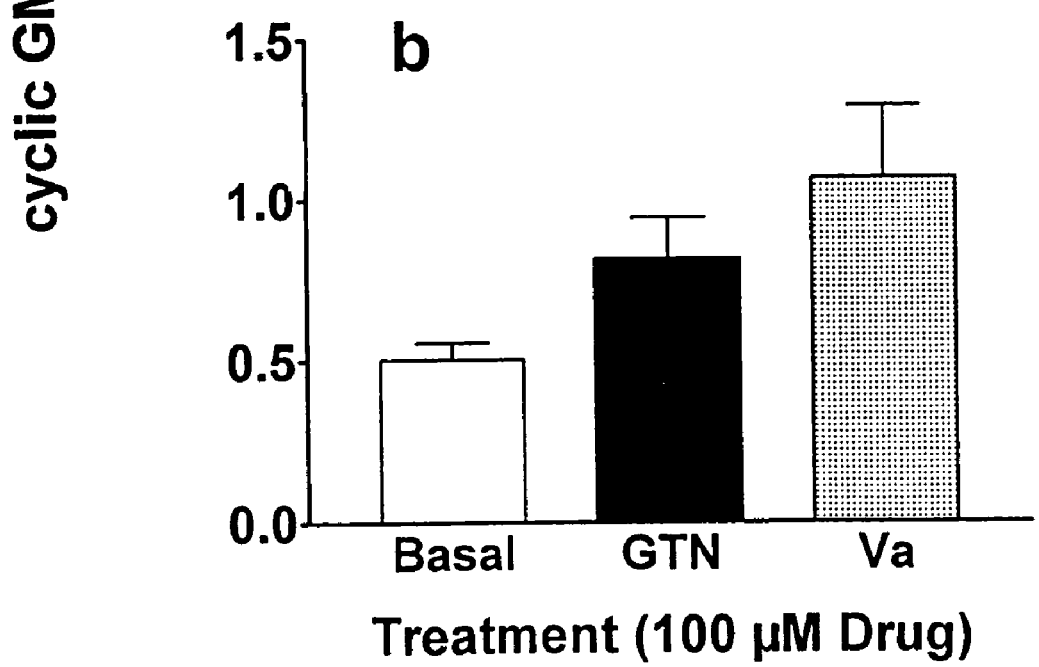

Sections of rat hippocampus (400 μm) were prepared and incubated in oxygenated Krebs solution at 37° C. After a 60-min equilibration period, the brain slices were stimulated with different concentrations of Va or GTN for 3-min. Cyclic GMP accumulation was determined as described above for aortic strips. FIG. 6 shows that Va causes a concentration-dependent increase in the tissue levels of cGMP in rat hippocampal brain slices in vitro, and that at high concentration (100 μM) Va is more effective than GTN in elevating cGMP levels in hippocampal brain slices in vitro. These data are in very good agreement with the differential effects of Va and GTN on hippocampal GCase activity shown in FIG. 3b.

Example 3

Characterization of Relaxation of Isolated Blood Vessels

Figure 7:
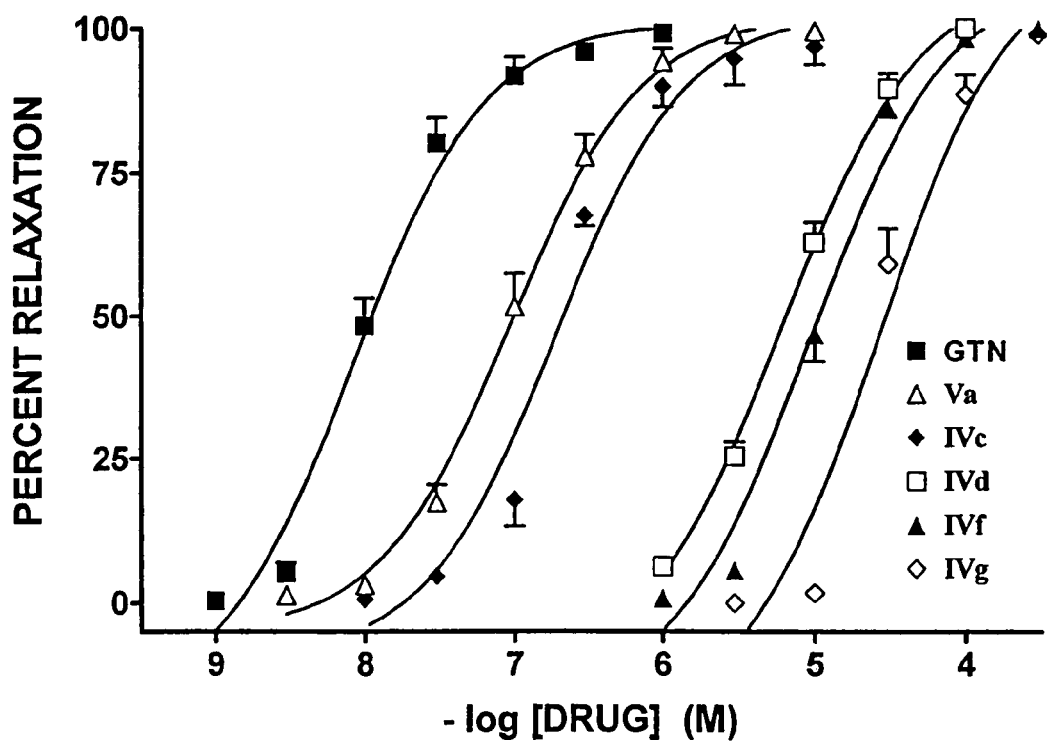
FIG. 7 is a graph showing the comparison of relaxation of isolated rat aorta induced by GTN (squares), Va (open triangles), compound IVc (diamonds), compound IVd (open squares), compound IVf (triangles), and compound IVg (open diamonds). Data points represent the mean±standard errors (n=5–8).
Figure 8:
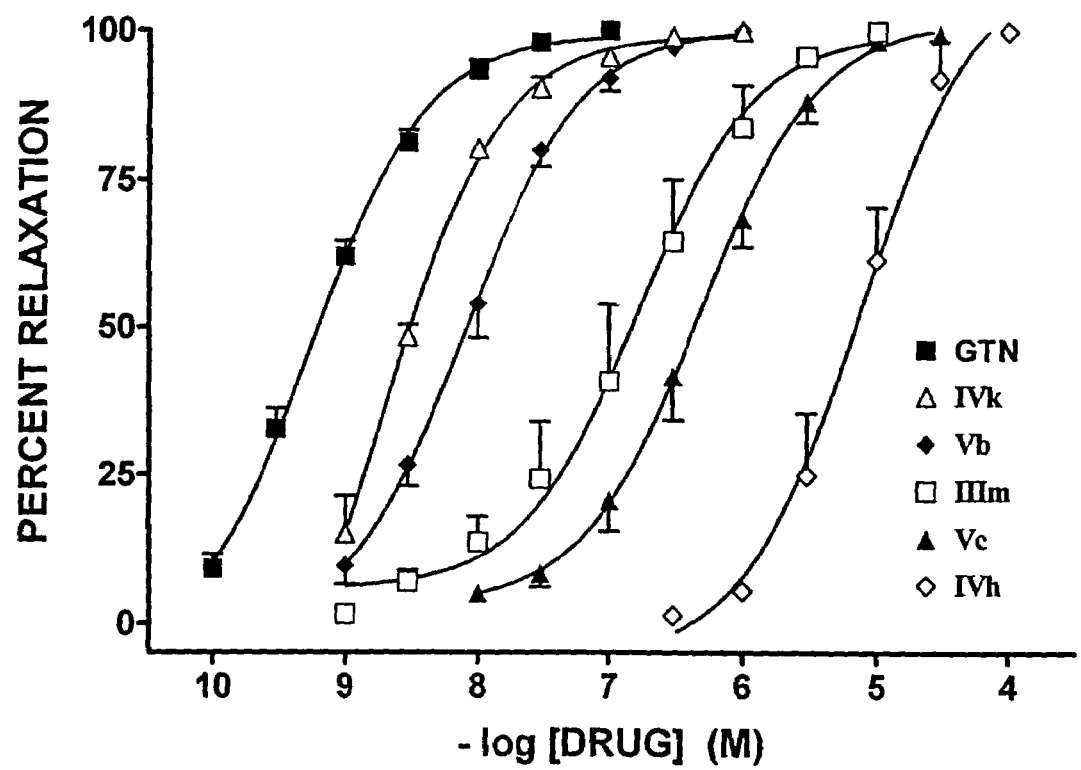
FIG. 8 is a graph showing the comparison of relaxation of isolated rat aorta induced by GTN (squares), IVk (open triangles), Vb (diamonds), IIIm (open squares), Vc (triangles), and IVh (open diamonds). Data points represent the mean±standard errors (n=3–8).
Figure 12:
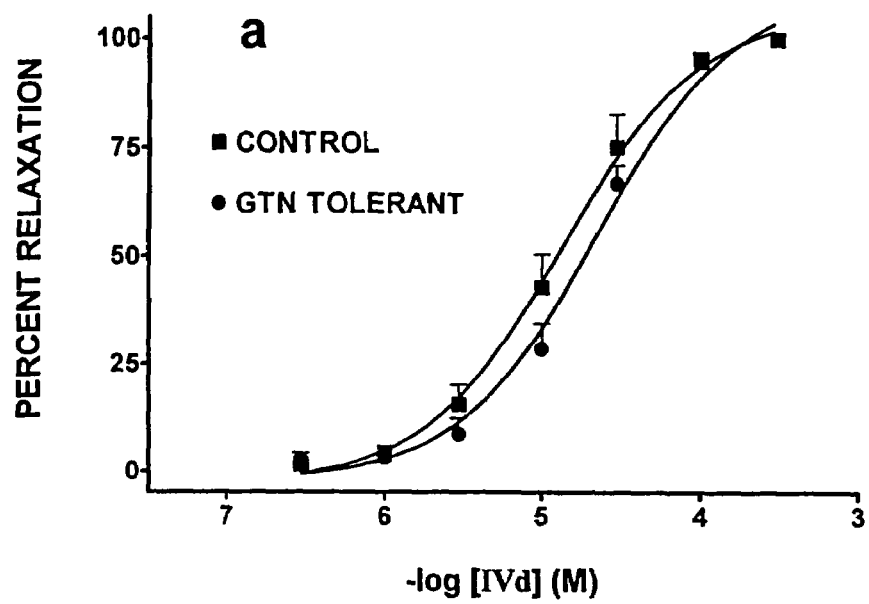
FIG. 12(a–b) is a graph showing the relaxation induced by compound IVd (a) and IVc (b) in untreated (squares) and GTN-tolerant (circles) isolated rat aorta. Aortae were made tolerant by treatment with 0.5 mM GTN for 30 min. Data points represent the mean±standard deviation (n=3–6).
Figure 12:
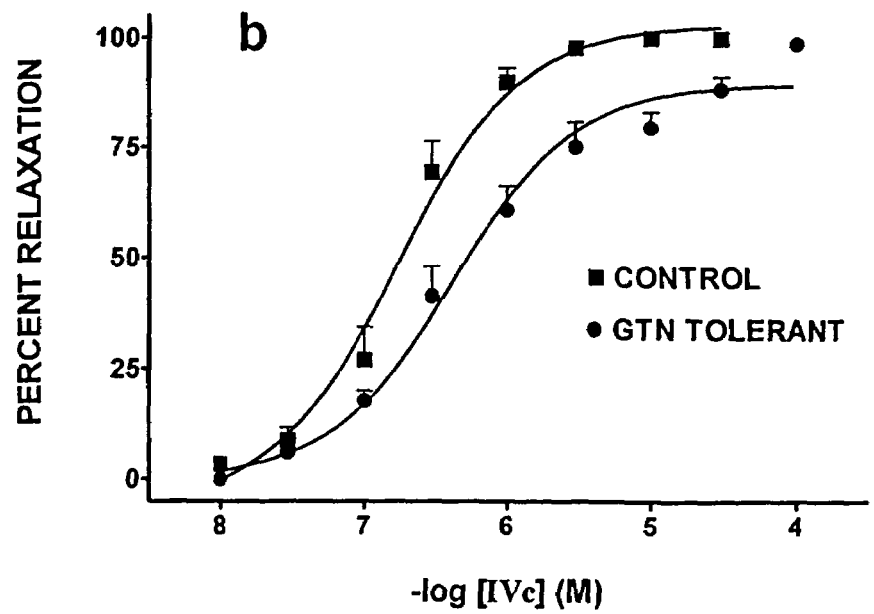

In order to extend the GCase data, the relaxing effects of nitrates IIIm, IVc, UVd, IVf, IVg, IVh, IVk, Va, Vb, and Vc on rat aortic tissue were examined. Thoracic aortic strips were prepared from male Sprague-Dawley rats (Charles-River, Canada) as described in McGuire et al. (1994) and Stewart et al. (1989). Tissues were contracted submaximally with phenylephrine (0.1 μM) and exposed to various concentrations of nitrovasodilator to obtain concentration-response curves. In this intact tissue assay, all of the nitrates were observed to cause relaxation of the tissue with a maximal relaxant response equal to that obtained with GTN. However, the compounds differed in potency, with EC-50 values of 7.87 nM, 94.3 nM, 6.59 μM, 25.2 μM, 11.0 μM, and 0.203 μM, for GTN and compounds Va, IVd, IVg, IVf, and IVc, respectively (FIGS. 7,8). In another series of experiments, the EC-50 values for relaxation were 0.61 nM, 3.19 nM, 8.40 nM, 0.153 μM, 0.437 μM and 6.89 μM for GTN, IVk, Vb, IIIm, Vc, and IVh, respectively (FIGS. 7,8). Compounds IVd and IVc were tested for their ability to cause vascular relaxation in tissues that had been made tolerant to the relaxant effect of GTN. GTN tolerance was induced by incubating tissues with high concentrations of GTN (0.5 mM GTN for 30 min). Under these conditions, the maximal relaxant effects of IVd (FIG. 12a) and IVc (FIG. 12b) were not significantly different to that of untreated tissue. The EC-50 for relaxation was increased approximately threefold, but the difference was not statistically significant.

Example 4

Characterization of Blood Pressure Changes in the Whole Animal

Figure 9:
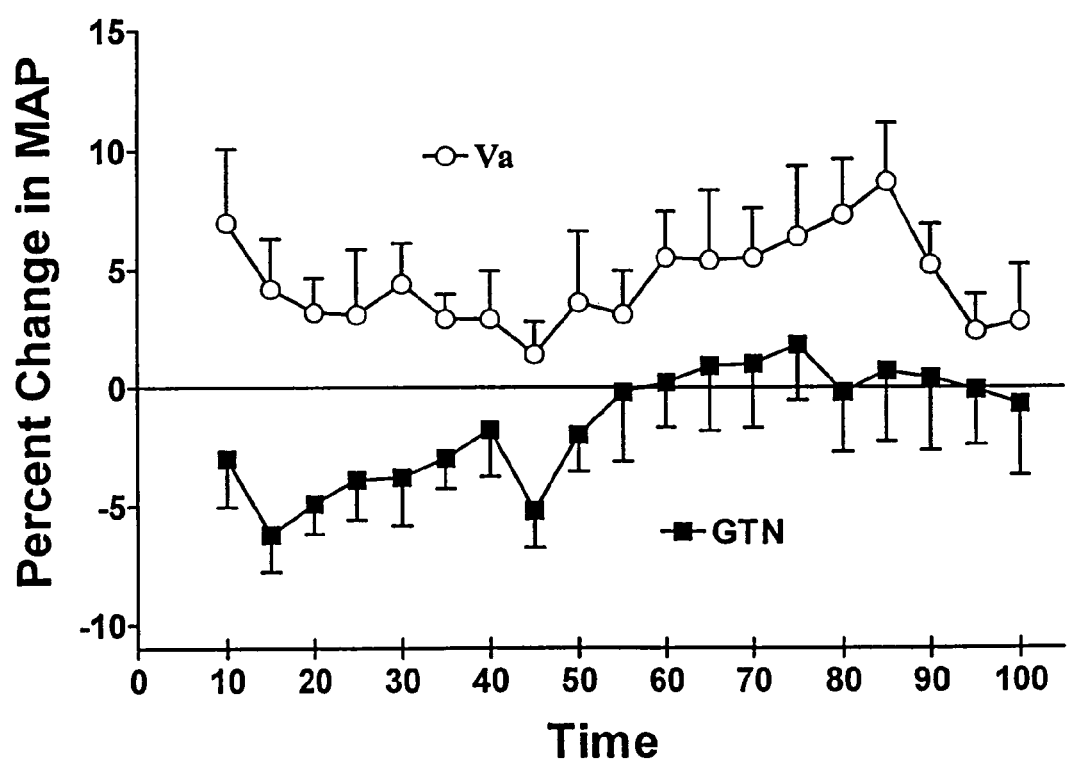
FIG. 9 is a graph showing the comparison of the percent change in mean arterial pressure (MAP) in conscious unrestrained rats after subcutaneous administration of 400 μmol/kg GTN (squares) or Va (open circles). Data points represent the mean±standard errors (n=6).
Figure 10:
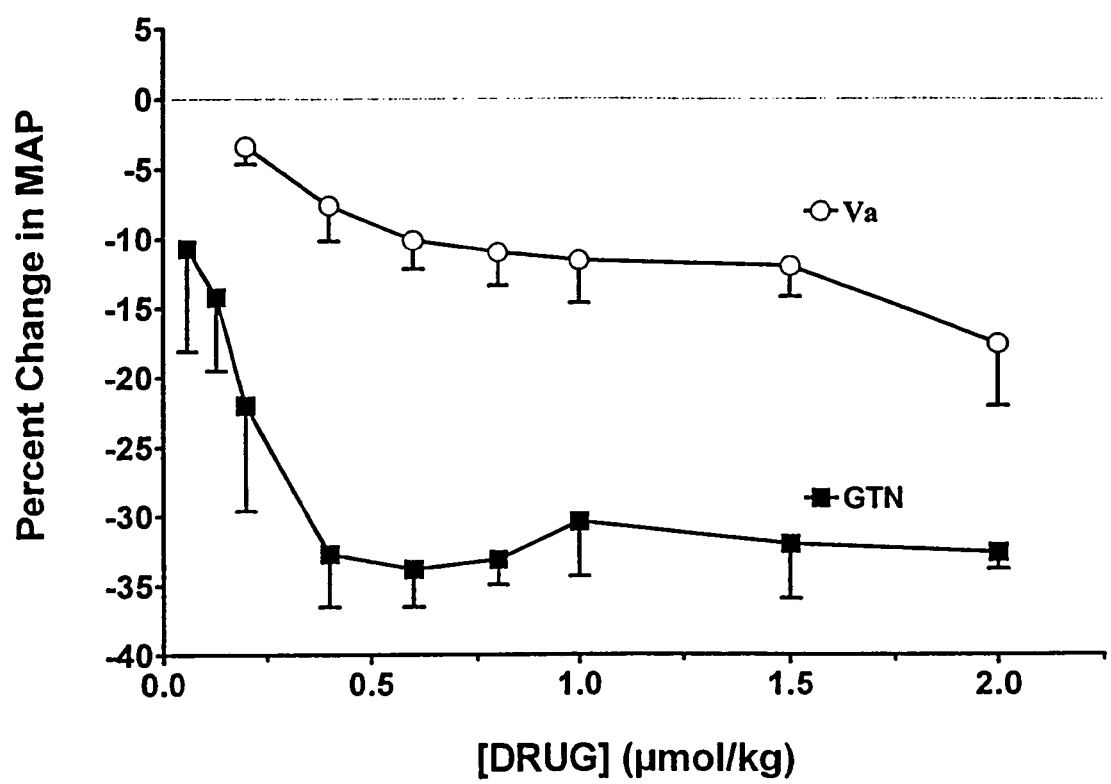
FIG. 10 is a graph showing the comparison of the percent change in mean arterial pressure in Inactin anaesthetized rats after intravenous bolus injection of GTN (squares) or Va (open circles). Data points represent the mean±standard errors (n=4).

To test for differential effects of nitrates on blood pressure responses, Va and GTN were injected into rats in which the abdominal aorta was cannulated for blood pressure recording. In the first experiment, Va and GTN were injected subcutaneously at a dose of 400 μmol/kg body weight into conscious, freely moving animals. GTN caused a small and transient decrease in blood pressure in these animals, whereas Va had no discernable effect on arterial blood pressure (FIG. 9). Va and GTN were subsequently tested in anesthetized rats in which the abdominal vena cava was also cannulated to allow for bolus intravenous injection of drugs. In this preparation, GTN caused a substantial and dose-dependent decrease in arterial blood pressure. In contrast, Va at equal doses had very modest effects on blood pressure at doses lower than 2 μmol/kg body weight (FIG. 10). These data are in very good agreement with the results obtained for these two agents using the isolated blood vessel preparation.

Figure 11:
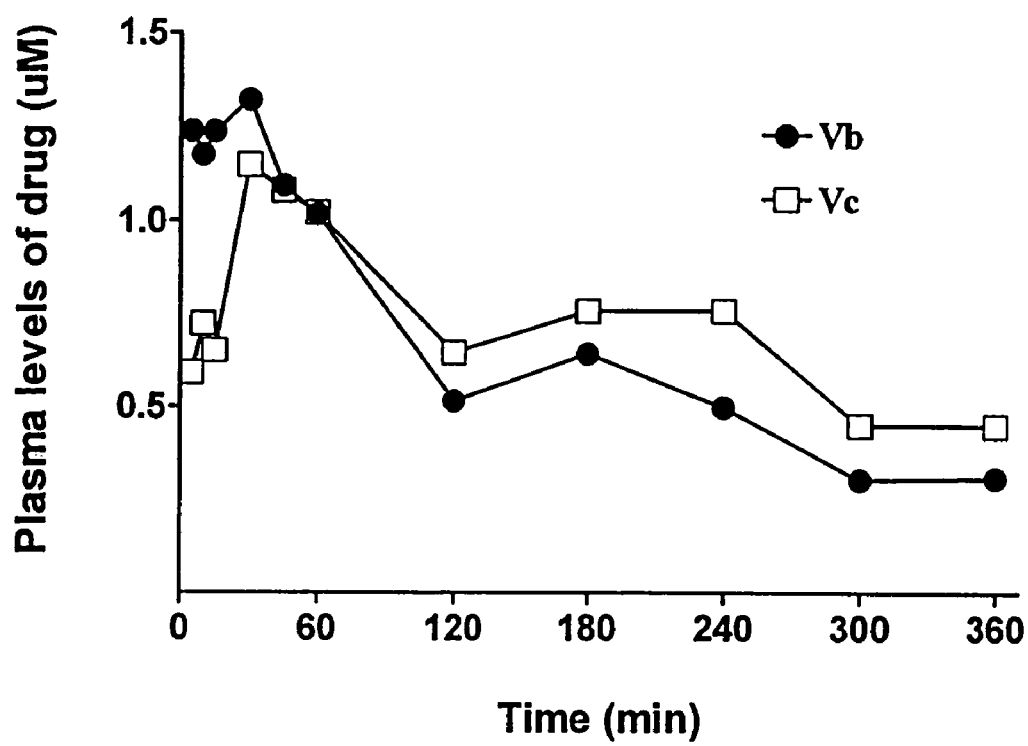
FIG. 11 is a graph showing the plasma levels (μM) of Vb (circles) and its mononitrate metabolite Vc (open squares) after subcutaneous administration of 200 μmol/kg Vb in conscious unrestrained rats. Data points represent the mean of two experiments.

The plasma levels of nitrates Vb and Vc (the denitrated metabolite of Vb) were measured to gain insight into the handling of these molecules in the body. Cannulas were placed in the abdominal aorta for blood sampling. After a two-day recovery period, a single subcutaneous dose of Vb (200 μmol/kg) was administered and blood samples collected over a period of six hours. Samples were centrifuged, the plasma collected, and the concentration of Vb and Vc determined by gas-liquid chromatography by the method of McDonald and Bennett (1990). The data obtained for Vb and Vc indicate that nitrates achieve maximal plasma levels within 30 minutes after subcutaneous injection, and therafter decline at a steady rate (FIG. 11). These data suggest that nitrates have excellent bioavailability after subcutaneous injection.

Example 5

Characterization of the Analgesic Effects of Novel Organic Nitrates in a Model of Acute Pain Injection of dilute acetic solutions into the peritoneum of a mouse induces writhing movements that can be quantified.

Figure 13:
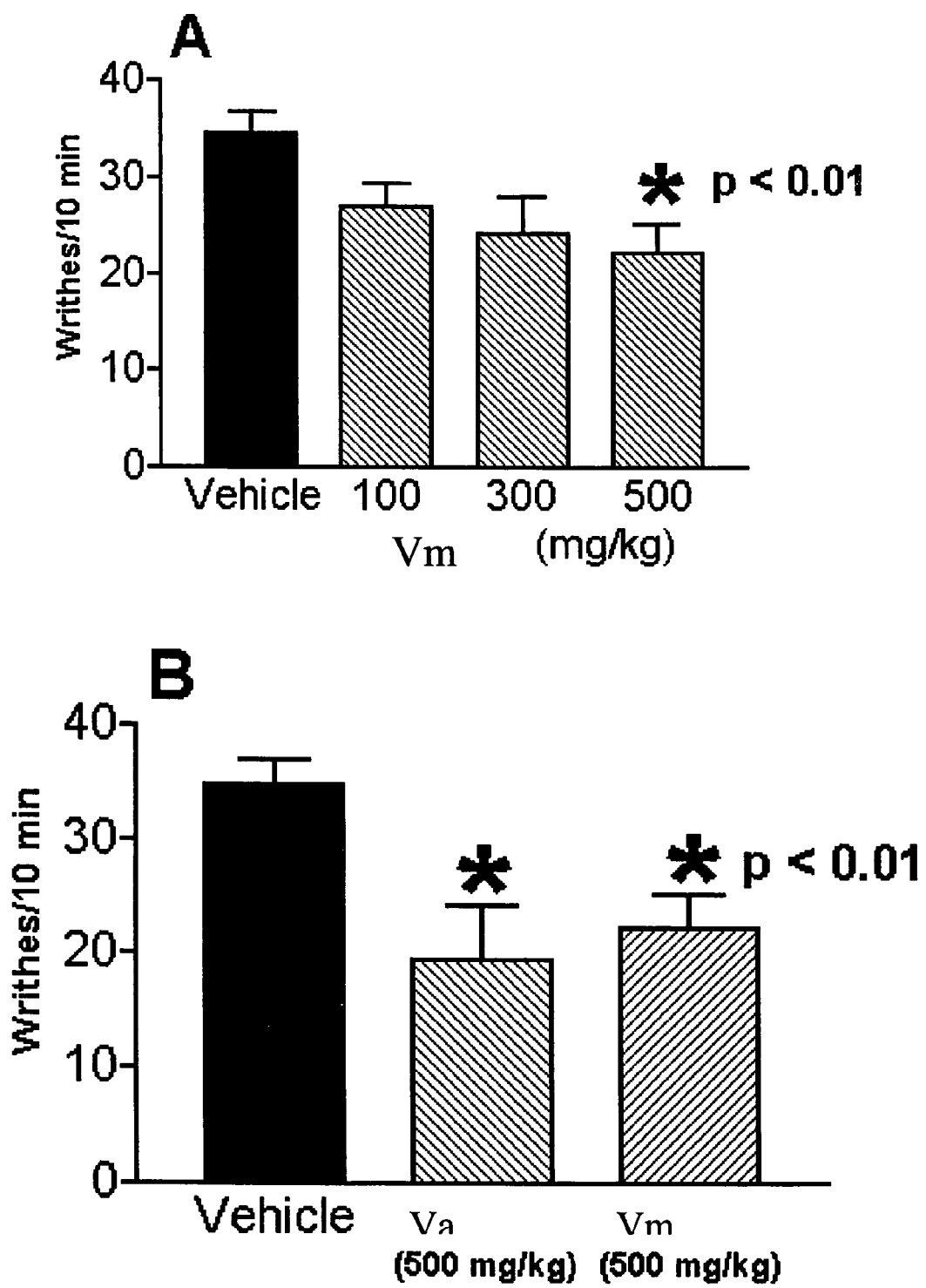
FIG. 13(A–B) is a graph showing the effect of Vm and Va in the mouse writhing test. GT Vm produced a dose-dependent analgesic effect (A). Va also produced analgesia in the mouse writhing test (B) Data are mean±standard errors (n=10–20).

We adopted the methodology described by Bak et al (1998) to test for analgesic effects of organic nitrates in this mouse model. Each mouse was given an intraperitoneal injection of 0.5 mL of a 0.6% solution of acetic acid in distilled water. After a 5 minute delay, the number of writhing movements was counted over a 10 minute period. To test the efficacy of novel organic nitrates in this model, drugs were administered at doses of 100–500 mg/kg (given by subcutaneous injection) 15 minutes before the intraperitoneal injection of acetic acid. In this model of acute pain, Vm induced a significant, dose-dependent analgesic effect, manifested as a decrease in the number of writhes per 10 minute period after intraperitoneal injection of dilute acetic acid (FIG. 13a). Va was also able to act as an analgesic (decreased writhing) in this experimental model when administered at a dose of 500 mg/kg subcutaneously (FIG. 13b).

Example 6

Figure 14:
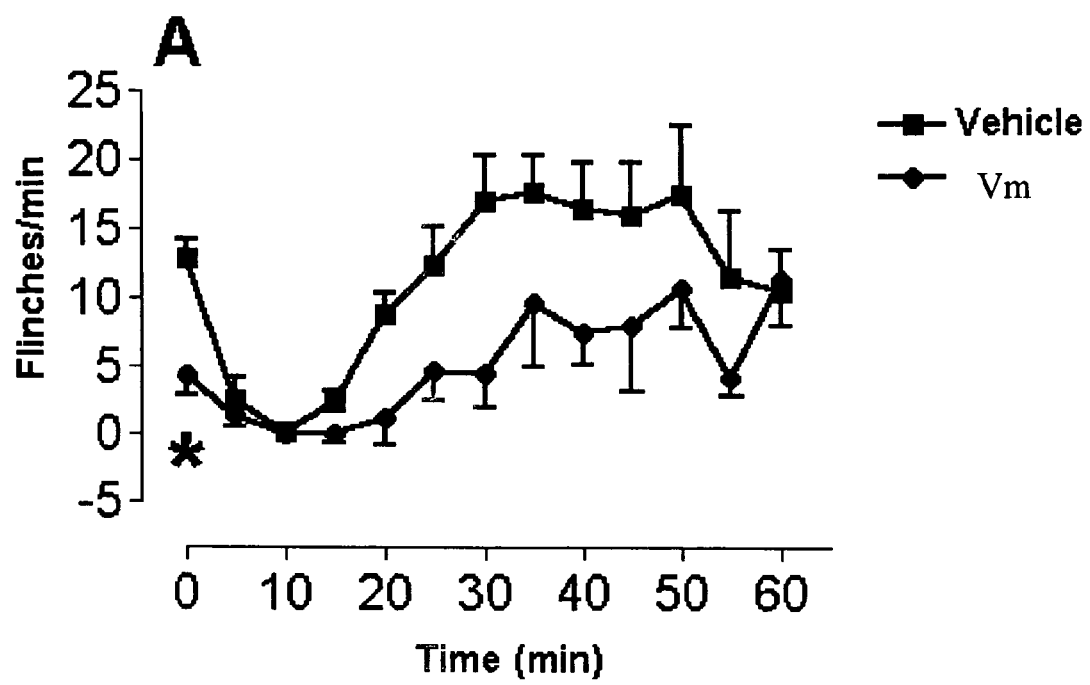
FIG. 14(A–B) is a graph showing the effect of Vm on paw flinches in rats after injection of formalin into the footpad. In comparison to vehicle-treated control animals, Vm decreased the initial pain response to formalin injection (at time=0, *, p<0.05), and the secondary hyperalgia that developed between 20 and 40 minutes after formalin injection (A). For each animal, a cumulative score (total number of flinches over 60 minutes) was calculated (B). Vm significantly decreased cumulative paw flinches for 60 minutes after formalin injection. Data are mean±standard errors (N=6–7).
Figure 14:
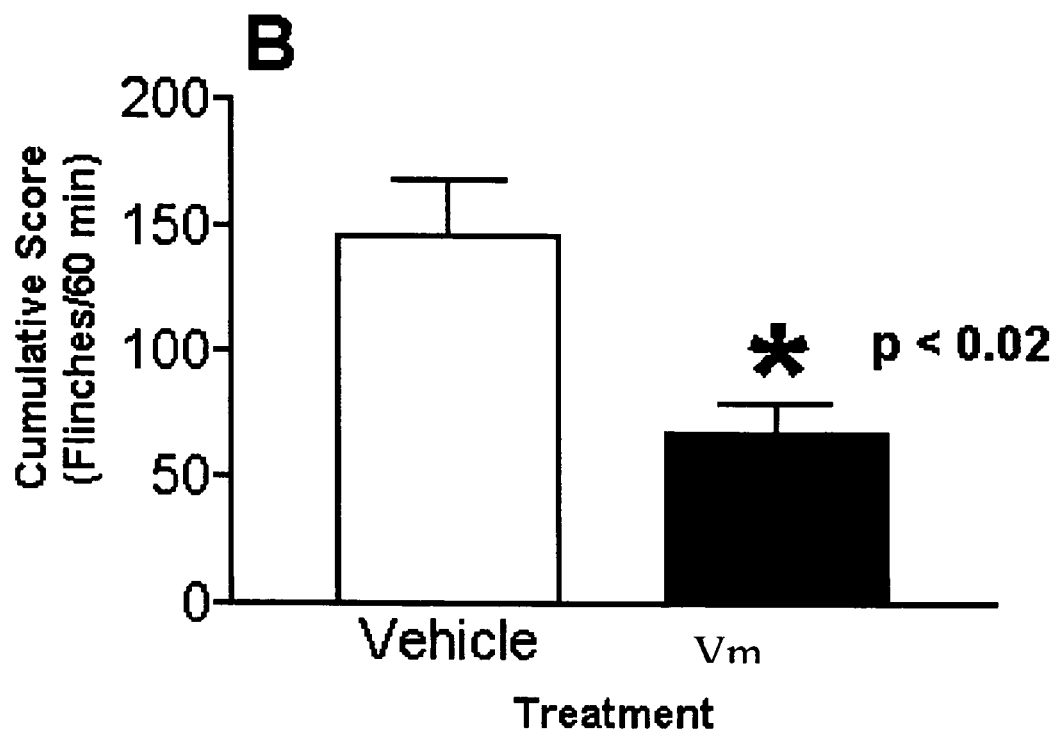

Characterization of the Analgesic Effects of Novel Organic Nitrates in a Model of Hyperalgesia/Allodynia Under light halothane anesthesia, male Sprague-Dawley rats were injected subcutaneously with 0.05 mL of 5% formalin into the dorsal surface of one hind paw as described in Malmberg and Yaksh (*Anesthesiology* (1993) 79, 270–281). The number of spontaneous paw flinches was determined in 1 minute blocks at 5 minute intervals for 60 minutes. Formalin injection in the paw produces two distinct phases of pain; an acute phase occurring within the first 5–10 minutes, and a delayed phase that develops between 15–30 minutes after formalin injection. The acute phase of the pain response to formalin is caused by activation of peripheral nociceptive sensory afferents (C-fibres) by the peripheral stimulus. The delayed pain response is considered to be a hyperalgesia/allodynia caused by a combination of sensitization of peripheral sensory afferents and sensitization of synaptic connections in the spinal cord. The formalin test in the rat is considered to be an appropriate model for tissue injury pain occurring in humans (Tjolsen et al., *Pain* (1992) 51, 5–17; Yaksh, TIPS (1999) 20, 329–337). In this experimental model of inflammatory tissue injury pain, Vm (500 mg/kg) significantly reduced both phases of the pain response to formalin injection (FIG. 14a,b).

Example 7

Synthesis of IIIe

To acetic anhydride (3 mL) was added gradually, with stirring, 70% nitric acid (0.26 mL), while keeping the temperature between 20–30° by external cooling. With continuous vigorous stirring the mixture was cooled to −30–35° and 2',3'-dideoxy-3-thiocytosine (0.25 g) was added. After 10 min at −35°, the reaction mixture was heated up to −20° and then stirred at −20–10° for 15 min and 10 min at 0°. The resulting reaction mixture was poured into ice-water, stirred for 1 h, then NaHCO$_3$ was added by portions until CO$_2$ evolution ceased. The water solution was extracted with 3×20 mL of ethyl acetate. Combined extracts were dried (MgSO$_4$) and concentrated. 0.38 g of slightly yellowish oil was obtained. The oil crystallized in a day and was recrystallized from CHCl$_3$. Yield 52%. Conversion to the nitrate was evidenced by the significant downfield shift of the C5' proton multiplet from δ 3.6 to 4.85 ppm.

Example 8

Synthesis of Nitrate IIIf 0.26 mL (4.15 mmol) conc. HNO$_3$ was added to 2 mL acetic anhydride such that the temperature did not exceed 25–30° C. The mixture was cooled at 0–5° C. and 0.3 g (1.88 mmol) of 5-(1,2-dihydroxyethyl)-4-methylthiazole was added in several portions, the temperature being kept below 5° C. The reaction mixture was stirred at 0–5° C. for 45 min and then 0.45 mL water was added. The mixture was stirred for 30 min and then rotavary evaporated. The residue was neutralized by adding 5 mL of saturated NaHCO$_3$ solution and the organic product was extracted with ethyl acetate. The organic layer was concentrated and the dinitrate IIIf was purified through column chromatography (silica gel/ethyl acetate eluant). A slightly yellow solid was obtained. Yield: 0.150 g (32%).

Example 9

Synthesis of Nitrate IIIi

Nitrate IIIi was obtained by two routes. Route I proceeded from the elimination reaction of IIIm in basic solution. Route II proceeded from nitration of trans-3-bromo-4-hydroxytetrahydrothiophene-1,1-dioxide, yielding nitrate IIIn, followed by reaction with a weak base, e.g., sodium thiocyanate in 2-butanone. Purification may be achieved with silica flash column chromatography using 1:1 hexane:ethyl acetate as eluant.

Example 10

Synthesis of Nitrate IIIj 1,4-Dibromo-2,3-butanediol may be nitrated: (a) using a nitration mixture prepared from HNO$_3$ and H$_2$SO$_4$ over 2 days; or (b) using acetyl nitrate reacting for 2 hours. Work-up requires quenching of the reaction mixture in ice-water for an hour, extraction, drying, and evaporation. Successful purification of the title compound by silica gel column chromatography is achieved on a 25 g scale using a mixture of 70% hexane and 30% CH$_2$Cl$_2$ as eluent Example 11

Synthesis of Nitrate Ve

4-Methylbenzenethiol was obtained by adaptation of literature procedures from p-toluidine (J.-P. Morizur, *Bull. Soc. Chim. Fr.* (1964) 1338–1342; Bourgeois, *Recl. Trav. Chim. Pays-Bas* (1899) 18, 445–450). p-Toluidine hydrochloride (14.2 g, 0.098 mole) was diazotised at 5° C. with concentrated hydrocloric acid (16.5 mL) and sodium nitrite (7.2 g, 0.104 mole) in water (12 mL). The solution of diazonium salt was added over 1.5 h to a solution of ethyl xanthate (24 g, 0.149 mole) in water (30 mL) at 45–50° C. The mixture was kept at this temperature, under stirring, for a further 1 h. The xanthate ester was separated as a maroon oil, washed with 50 mL 10% NaOH and with water to neutral pH and dried over MgSO$_4$ (20 g of crude product). The crude xanthate was dissolved in 60 mL absolute ethanol and to this solution 20 g KOH (pellets) were added in portions. The reaction mixture was refluxed under stirring and Ar for 8 h, then concentrated under vacuum. The concentrate was taken up in 50 mL H$_2$O and extracted with 3×100 mL diethyl ether.

The aqueous layer was acidified with a 6N $H_2SO_4$ solution and extracted with 3×100 mL $CH_2Cl_2$. The combined extracts were washed with water, dried over $MgSO_4$, evaporated and flash columned on silica gel, eluant hexanes:ethyl acetate=9:1, giving 10 g (81.56%) of 4-methylbenzenethiol. $^1$H-NMR(CDCl$_3$, 300 MHz):7.18–7.24 (m, arom 2H), 7.04–7.11 (d, arom 2H, J 7.93), 3.41 (s, 1H), 2.32 (s, 3H). $^{13}$C-NMR (75.48 MHz): 21.34, 128.95, 130.24, 130.29, 136.05.

The dinitrate IVd (9.67 mmoles) was dissolved in 10 mL distilled water and the solution kept under Ar for 30 minutes. To this solution, a solution of 0.8 g (6.46 mmoles) of 4-methylbenzenethiol and 7 mL 1M NaOH was added dropwise. The resulting emulsion was stirred for 15 min and then extracted with 3×20 mL $CH_2Cl_2$. The combined organic extracts were washed with $H_2O$, dried over $MgSO_4$ and concentrated under vacuum. The remaining oil was purified by flash column chromatography on silica gel, eluant hexanes:ethyl acetate=9:1, giving the product Ve (1.097 g, 52.22%). $^1$H-NMR(CDCl$_3$, 300 MHz):7.44–7.51 (m, arom 2H), 7.17–7.24 (d, arom 2H, J 7.91), 5.47–5.59 (m, 1H), 4.83–4.93 (dd, 1H, J 12.81, 2.78), 4.57–4.67 (dd, 1H, J 12.82, 5.71), 3.02–3.12 (dd, 1H, J 14.48, 6.01), 2.9–2.99 (dd, 1H, J 14.47, 7.72), 2.38 (s, 3H). $^{13}$C-NMR (75.48 MHz): 21.53, 36.78, 69.82, 77.68, 130.52, 130.62, 132.55, 139.23.

Example 12

Synthesis of Nitrate IIIm 3,4-Epoxytetrahydrothiophene-1,1-dioxide (250 mg,1.9 mmol) was refluxed for 24 h in 10 mL of water and 25 mg of toluenesulfonic acid. After the first 6 h, another 25 mg of the acid was added. The reaction was monitored by thin layer chromatography (TLC) (5% methanol in dichloromethane). Purification was by Si flash column chromatography using 5% methanol/$CH_2Cl_2$ as eluent to afford 200 mg of diol. The diol was nitrated in a cooled solution of conc. sulfuric acid (2 mol eq.), nitric acid (70%, 2 mol eq.) in an ice bath. The temperature was maintained as close to 0° C. as possible. The ice bath was removed and the mixture was allowed to stir for 1 hour (reaction was monitored by TLC, 100% $CH_2Cl_2$ eluent). The acid layer was removed and the organic layer washed with: (i) water; (ii) 10% sodium carbonate; (iii) 10% urea; (iv) water. Drying over sodium sulfate, filtration and concentration, yielded crude product which was purified by flash column chromatography, with dichloromethane as eluent. An alternative route involves direct nitration of 3,4-epoxytetrahydrothiophene-1,1-dioxide in a similar nitration mixture.

Example 13

Synthesis of Nitrate IVk 1.17 mL (18.2 mmol) concentrated $HNO_3$ was added, under stirring and cooling (0–5° C.), to 1 mL (18.2 mmol) concentrated $H_2SO_4$ and then 2 g (14 mmol) of 4-methyl-5-(2-hydroxyethyl)thiazole was added dropwise into the nitration mixture, the temperature being kept under 10° C. The mixture was stirred for 3 hours at room temperature, diluted with 10 mL of water and neutralized with solid $NaHCO_3$. The organic product was extracted with ethyl acetate and purified by column chromatography (silica gel/ethyl acetate eluent) to produce a colorless oily product. Yield: 1.18 g (45%).

Example 14

Synthesis of Nitrate IVi 0.03 g (0.035 mL) of allyl cyanide was added to a stirred suspension of 0.22 g (0.5 mmol) of Tl $(NO_3)_3 \cdot 3H_2O$ in 2 mL of pentane. After 20 min of vigorous stirring the pentane solution was decanted and evaporated to dryness. After evaporation the residual oil (0.44 g) was columned ($CH_2Cl_2$, Rf 0.64 ($CH_2Cl_2$). Clean oil immediately crystallized during attempt to dissolve it in CDCl$_3$. Yield 0.065 g (76%). The structure of IVn was confirmed by X-ray analysis. IR (film): 1297.03, 1678.91, 2258.91 (CN). Mass spec. m/z (CI$^+$, fragment, %): 191.9 (M+H, 2.44), 129.0 (16.41), 81.9 (100). Calculated for $C_4H_5N_3O_6$ 191.02.

Example 15

Synthesis of Nitrate IVm 0.9 g (0.75 mL, 4.92 mmol) of allyphenyl sulfone was added dropwise to a stirred suspension of 2.43 g (5.47 mmol) of Tl $(NO_3)_3 \cdot 3H_2O$ in 10 mL of pentane. The resulting mixture was stirred overnight. The pentane solution was decanted. 2×10 mL of methanol were added to the reaction mixture, stirred for 10 minutes and extracts were added to the pentane solution. The combined extracts evaporated to dryness and purified by silica flash column chromatography using $CH_2Cl_2$ as eluant Yield 0.08 g (15%). IR (KBr): 1152.39, 1290.91, 1273.12, 1353.83, 1646.08. Mass spec. m/z (CI$^+$, fragment, %): 307.0 (M+1, 66.5), 244.0 (100%). Calculated for $C_9H_{10}N_2O_8S$ 306.02.

Example 16

Synthesis of Nitrate Va 2.2 g (7.3 mmol) of nitrate IVd was dissolved in 5 g of cold $H_2O_2$ (30%, 0° C.) and then 1 g of 10% $H_2SO_4$ was added. The mixture was stirred at 0–5° C. until a white oil separated (ca. 30–60 min). The aqueous layer was discarded and the oil was dissolved in dichloromethane, washed successively with water, then $NaHCO_3$ solution and finally water. The organic solution was dried over $MgSO_4$. Removal of the solvent produced 1.3 g of the crude product which was purified by column chromatography (Silicagel, $CH_2Cl_2$/hexanes: 70/30). Yield: 0.650 g (45%).

Example 17

Synthesis of Nitrate Vc 3 g (8.88 mmol) of 1,4-dibromo-2,3-dinitrobutanediol and 2.81 g (18 mmol) of $Na_2S_2O_3 \cdot 5H_2O$ were dissolved in the mixture of 100 mL of methanol and 45 mL of $H_2O$. The resulting solution was heated during 4 days at 40–45°. After this time the reaction mixture was partially evaporated to reduce the volume of solvents. The resulting mixture was extracted 4×50 mL of ethyl ether. The extracts were combined, washed ($H_2O$), dried ($MgSO_4$) and evaporated to minimum. Column chromatography afforded the title compound in 10% yield, seperated from Vb the major product.

Example 18

Synthesis of Nitrate Vy

The title compound was synthesised by the reaction of IVd with 4-methyl-5-thiazole ethanthiol, in a similar procedure to that used in Example 11. The crude product was purified by column chromatography (Silicagel, ethyl acetate eluant) to give product (50 mg, 27.32%). $^1$H-NMR(CDCl$_3$, 300 MHz): 8.22 (s, 1H), 5.49–5.6 (m, 1H), 4.9–5.00 (dd, 1H), 4.64–4.78 (dd, 1H), 3.14–3.22 (t, 2H), 2.89–3.07 (m, 4H), 2.45 (s, 3H). Mass spec., m/z (EI$^+$, fragment, %): 355.0 Calculated for C$_9$H$_{13}$N$_3$O$_6$S$_3$: 355.0. The 4-Methyl-5-thiazole precursor was obtained from 4-methyl-5-thiazole ethanol, thiourea and hydrobromic acid by adaptation of literature procedures (R. L. Frank, P. V. Smith, *J. Am. Chem. Soc.* (1946) 68, 2103–2104). A mixture of 2 g 4-methyl-5-thiazole ethanol (13.965 mmoles), 1.063 g(13.965 mmoles) thiourea and 9.45 g (56 mmoles) hydrogen bromide as 48% hydrobromic acid was refluxed for 7 h with stirring, under Ar. A solution of 2.24 g (56 mmoles) of NaOH in 20 mL of water was then added and the mixture was refluxed without stirring for 2 h. The layers were separated, and the acidified aqueous layer was extracted with three 30 mL portions of CH$_2$Cl$_2$. The extracts and original organic layer were combined, dried over MgSO$_4$ and concentrated under vacuum to afford 1.9 g crude product which was purified by column chromatography using ethyl acetate as eluent (Yield 1.6 g, 75%). $^1$H-NMR(CDCl$_3$, 300 MHz): 8.5 (s, 1H), 2.94–3.02 (t, 2H), 2.62–2.72 (q, 2H), 2.33 (s, 3H), 1.38–1.45 (t, 1H). $^{13}$C-NMR (75.48 MHz): 15.41, 26.41, 31.51, 39.72, 129.36, 149.90

Example 19

Synthesis of Nitrate IIIk and IIIl

Synthesis from dinitrate IIIj proceeded by refluxing with sodium ot potassium thiocyanate (2 eq.) in 2-butanone for 8 h. After cooling, a precipitate was removed by filtration and the filtrate was concentrated. Nitrates IIIk and IIIl were separated by silica flash column chromatography with hexane/dichloromethane as eluent.

Example 20

Synthesis of Nitrate Vk

IVd (0.43 g, 1.37 mmol) was dissolved in 10 mL of distilled water and the emulsion of 0.23 g (1.28 mmol) of the ethyl ester of thiosalycilic acid in 1.3 mL of 1 M NaOH was added. The resulting solution immediately became turbid and was stirred for 3 min, then extracted with ethyl acetate (4×15 mL). The resulting extracts were washed with H$_2$O, dried (MgSO$_4$), and concentrated by evaporation. The residue was flash columned on silica gel, eluant hexane:ethyl acetate=9:1 (R$_f$ 0.23), giving 0.27 g (55%) of Vk. $^1$H-NMR (CDCl$_3$, 300 MHz): 8.06–8.12 (1H, dd, J 8.12, 0.36), 7.99–8.04 (1H, dd, J 7.8, 1.15), 7.51–7.59 (1H, m, J 7.24, 1.44), 7.21–7.29 (1H, m, J 7.35, 0.54), 5.40–5.49 (1H, m), 4.70–4.78 (1H, dd, J 13.04, 2.95), 4.33–4.45 (3H, m, superposition of dd a 13.08, 6.01) of 1H from CH$_2$—ONO$_2$ and quart, from O—CH$_2$—CH$_3$), 2.66–2.87 (2H, m), 2.06–2.15 (2H, quart., J 6.92), 1.35–1.43 (3H, t, J 7.14). $^{13}$C-NMR: (CDCl$_3$, 75.48 MHz): 166.21, 140.41, 132.78, 131.46, 127.63, 125.48, 77.25, 71.03, 61.42, 32.51, 28.29, 14.17. Mass spec. m/z (EI$^+$, fragment, %): 392.3 (M+, 3.69), 153 (100). Calculated for C$_{13}$H$_{16}$N$_2$O$_8$S$_2$ 392.03.

Example 21

Chiral Synthesis of Nitrate IVd

A 50 mL round-bottom flask, equipped with a magnetic stirrer, was charged with 10 mL of tert-butyl alcohol, 10 mL of water, and 2.8 g of a catalyst (AD-mix-β, Aldrich: K. B. Sharpless, W. Amberg, Y. L. Bennani, G. A. Crispino, J. Hartung, K.-S. Jeong, H.-L. Kwong, K. Morikawa, Z.-M. Wang, D. Xu, X.-L. Zhang, *J. Org. Chem.* (1992) 57, 2768–2771). Stirring at room temperature produced two clear phases; the lower aqueous phase appears bright yellow. The mixture was cooled to 4° and 0.2 mL (2 mmol) of allylbromide was added at once, and the heterogeneous slurry was stirred vigorously at 4–5° for 2.5 h (monitoring by TLC hexane:methanol=1:9). While the mixture was stirred at 0° C., solid sodium sulfite (3 g) was added and the mixture was allowed to warm to room temperature and stirred for 1 h. Then 20 mL of ethyl acetate was added to the reaction mixture, and after separation of the layers, the aqueous phase was further extracted with ethyl acetate. The combined organic extracts were dried (MgSO$_4$), concentrated in vacuo and purified by flash chromatography on silica (hexane:methanol=1:9, R$_f$ 0.5), to yield chiral 1-bromo-2,3-propanediol. Yield 0.2 g (55.5%). Optical rotation: minus. Nitration to 1-bromo-2,3-dinitroxypropane was achieved using reaction in HNO$_3$/H$_2$SO$_4$ (K. Yang, J. D. Artz, J. Lock, C. Sanchez, B. M. Bennett, A. B. Fraser, G. R. J. Thatcher, *J. Chem.Soc., Perkin Trans.* (1996) 1, 1073–1075) and the product was purified by flash chromatography on silica gel (hexane:CH$_2$Cl$_2$=2:3, R$_f$ 0.5). Yield 55.5%. Optical rotation: minus. The dinitrate IVd was synthesised from chiral 1-bromo-2,3-propanediol by our usual procedure (K. Yang, J. D. Artz, J. Lock, C. Sanchez, B. M. Bennett, A. B. Fraser, G. R. J. Thatcher, *J. Chem. Soc., Perkin Trans.* (1996) 1, 1073–1075), and purified by flash chromatography on silica (ethyl acetate:methanol=9:1). Yield 2.27%. Optical rotation: plus.

Example 22

Chiral Synthesis of Nitrate Vk

The same procedure as described above for racemic Vk was utilized for the stereospecific synthesis of Vk from the sterechemically resolved, chiral dinitrate IVd.

Example 23

Synthesis of Tetranitrate Vx

The title compound was synthesised by the reaction of IVd (0.345 g, 1.15 mmoles) with captopril methyl ester (0.2 g, 0.865 mmoles) in the presence of 1 mL of 1M NaOH. The crude product was purified by column chromatography (Silicagel, ethyl acetate) to afford 0.1 g (18.03%) of unsymmetrical disulphide. $^1$H-NMR(CDCl$_3$, 300 MHz): 5.49–5.61 (m, 1H), 4.88–4.90 (m, 1H), 4.62–4.74 (m, 1H), 4.40–4.55 (m, 1H), 3.59–3.78 (m, superpos. 5H), 2.69–3.21 (m, superpos. 5H), 2.14–2.29 (m, 1H), 1.90–2.12 (m, 3H), 1.22–1.28 (d, 3H). $^{13}$C-NMR (75.48 MHz): a mixture of enantiomers can be seen: 17.39, 25.20, 29.40, 36.41, 36.51, 38.55, 41.94, 42.19, 47.32, 52.56, 59.12, 69.90, 70.29, 77.89, 78.00, 173.01, 173.48.

Example 24

Synthesis of Nitrate Vq

The title compound was synthesised by the reaction of Bunte salt (2.4 g, 8 mmoles) with 4,4'-thiobisbenzenethiol (0.5 g, 2 mmoles) in the presence of 4.4 mL of 1M NaOH. The crude product was purified by column chromatography (silica gel, hexanes/$CH_2Cl_2$: 3/7) to afford 0.28 g (21.82%) disulphide. $^1$H-NMR($CDCl_3$, 300 MHz): 7.2–7.6 (m, arom 8H), 5.42–5.56 (m, 2H), 4.82–4.95 (dd, 2H), 4.55–4.67 (dd, 2H), 2.93–3.15 (m, 4H).

Example 25

Synthesis of Nitrate Vr

The title compound was synthesised by the reaction of IVd (0.5 g, 1.58 mmoles) with ethyl 2-mercapto-3-(3',4'-methylenedioxy-phenyl) propenoate (0.2 g, 0.8 mmoles). The crude product was purified by column chromatography (Silicagel, hexanes/$CH_2Cl_2$: 3/7) to give Vr (0.1 g, 28.09%). $^1$H-NMR($CDCl_3$, 300 MHz):7.97 (s, 1H), 7.48–7.51 (d, 1H), 7.17–7.22 (m, 1H), 6.84–6.89 (d, 1H), 6.05 (s, 2H), 5.48–5.58 (m, 1H), 4.81–4.89 (dd, 1H), 4.53–4.61 (dd, 1H), 4.25–4.4 (m, 2H), 3.05–3.10 (m, 2H), 1.35–1.45 (t, 3H). $^{13}$C-NMR (75.48 MHz): 14.17, 36.27, 62.15, 69.71, 76.57, 101.77, 108.27, 110.31, 125.20, 127.55, 127.87, 146.87, 147.811, 149.76, 165.89.

Ethyl 2-mercapto-3-(3',4'-methylenedioxy-phenyl)propenoate was obtained by the following route:

(1) Ethylisothiocyanate (10 g, 0.115 moles), 7.9 g(0.086 moles) mercaptoacetic acid and 5 mL pyridine in $C_6H_6$ was refluxed, cooled and filtered yielding 3-ethylrhodanine, which was used in the next step without any further purification. Reaction of 3-ethylrodanine with piperonal in the presence of sodium acetate was performed in $CH_3OH$ under refluxing for 1 h. The yellow precipitate obtained after cooling and filtration, was washed several times with $CH_3OH$ on the filter and crystallizated from $CH_3OH$ to give 3-ethyl-5-piperilidenerodanine. $^1$H-NMR(DMSO-$d_6$, 300 MHz):7.72 (s, 1H), 7.1–7.3 (m, 3H), 6.14 (s, 2H), 3.95–4.15 (q, 2H), 1.15–1.20 (t, 3H). $^{13}$C-NMR (75.48 MHz): 12.76, 40.28, 103.07, 110.21, 110.47, 120.68, 127.89, 128.07, 134.01, 149.23, 150.74, 167.57, 193.68.

(2) 3-Ethyl-5-piperilidene-rodanine (1 g, 3.4 mmoles) was added to a stirred solution of 0.16 g (6.8 mmoles) in 8 mL abs. ethanol and the mixture was refluxed for 30 min. To the solution cooled to room temperature 5 mL $H_2O$ were added and the mixture was hydrolized with 10% HCl and extracted with ether. The ether phase was separated, dried ($MgSO_4$) and evaporated to an oil. Since the investigation by TLC of the crude reaction mixture indicated the presence of piperonal, the reaction mixture was dissolved in $CH_2Cl_2$ and the obtained solution was washed with 1M NaOH. The aqueous phase was extracted twice with $CH_2Cl_2$ and then neutralized with dilute HCl. Free thiol was extracted with ethyl ether. After concentration, the product was purified by column cromatography eluating with hexane/ethyl ether:8/2. Yield 0.4 g (62.4%). $^1$H-NMR($CDCl_3$, 300 MHz):7.69 (s, 1H), 7.7.25–7.29 (d, 1H, J 1.46), 7.1–7.18 (m, 1H), 6.85–6.9 (d, 1H, J 8.13), 6.01 (s, 2H), 4.75 (s, 1H), 4.28–4.38 (q, 2H, J 7.12), 1.35–1.42 (t, 3H, J 7.13). $^{13}$C-NMR (75.48 MHz): 14.20, 62.5, 101.41, 108.37, 109.43, 121.06, 125.45, 129.20, 134.68, 147.80, 148.05, 165.43.

Example 26

Synthesis of Nitrate IVs

The title compound was synthesised by the reaction of IVb with dithiothreitol in $CH_3OH$ and was isolated as an oil in 15–20% yield (CAUTION: stench). $^1$H-NMR($CDCl_3$, 300 MHz): 5.23–5.32 (1H, m), 4.87 (1H, dd, J 12.82, 3.22), 4.68 (1H, dd, J 12.83, 6.09), 2.77–2.94 (2H, m), 1.66 (1H, t, J 9.07). $^{13}$C-NMR: ($CDCl_3$, 75.48 MHz): 79.39, 69.30, 23.68.

Example 27

Synthesis of Nitrate IVt

The title compound was synthesised by the reaction of nitrate IVs with acetyl chloride in $CHCl_3$. Isolated yield 50%. $^1$H-NMR($CDCl_3$, 300 MHz): 5.29–5.38 (1H, m), 4.76 (1H, dd, J 12.94, 3.11), 4.55 (1H, dd, J 12.94, 6.37), 3.30 (1H, dd, J 14.06, 5.98), 3.13 (1H, dd, J 14.61, 6.35). $^{13}$C-NMR: ($CDCl_3$, 75.48 MHz): 194.10, 77.00, 69.79, 30.42, 27.78. Mass spec. m/z (EI$^+$, fragment, %): 240.0 (M$^+$, 1.17), 193.9 (M—$NO_2$, 10.86), 148.8 (100). Calculated for $C_5H_8N_2O_7S$ 240.01.

Example 28

Synthesis of Nitrate IIIw

Diethyl 1-chloro-2-trimethylsiloxypropylphosphonate was obtained by adaptation of literature methods (T.Azuhata, Y.Okamoto, *Synthesis* (1983) 916–917). This phosphonate was quantitatively converted to diethyl 1-chloro-2-hydroxypropylphosphonate using $CH_3OH$. After stirring for 15 min the resulting reaction mixture was evaporated to a minimum and subjected to nitration with a mixture of $HNO_3$ and $H_2SO_4$ Work-up and flash column chromatography on silica (ethyl acetate eluant) yielded pure product in 25% yield. $^{31}$P ($CDCl_3$ 162 MHz): 24.60. $^1$H ($CDCl_3$, 300 MHz): 5.31–5.45 (m, 1H, 3.92–4.08 (m, 4H), 3.63–3.81 (m, 2H), 2.03–2.30 (m, 2H), 1.16–1.24 (superposition of 2 t, 6H, J 7). $^{13}$C ($CDCl_3$, 75 MHz): 76.83, 62.15 (d, J 6.37), 43.77 (d, J 8.95), 27.08 (d, J 142.00), 15.99 (d, J 5.88).

Example 29

Synthesis of Nitrate IIIx

Treatment of IIIw with 1 mole of $Me_3SiBr$ for 1 h with subsequent addition of $CH_3OH$ provided the monodealkylated phosphonic acid in high purity. Transformation of the free acid to its sodium salt IIIx was achieved using the cation-exchange resin Amberlite IR-122—Na$^+$ form. $^{31}$P ($CD_3OD$, 122 MHz): 17.62. $^1$H ($CD_3OD$, 300 MHz): 5.38–5.63 (m, 1H), 3.75–4.25 (superposition of 2 m, 4H), 1.88–2.20 (m, 2H), 1.12–1.28 (t, 3H). $^{13}$C ($CD_3OD$, 75 MHz): 81.14, 61.17 (d,J 5.41), 45.56 (d,J 5.94), 29.35 (d,J 131.74), 17.00 (d,J 6.75)

Example 30

Figure 15:
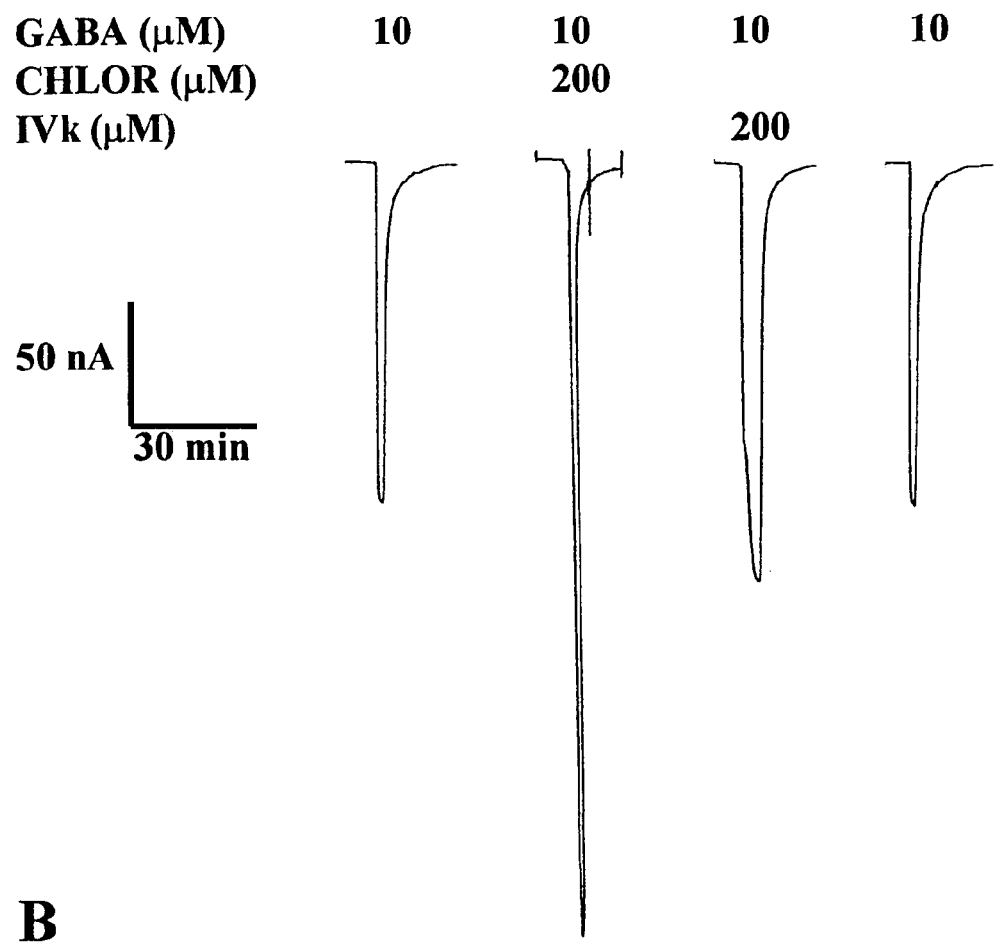
FIG. 15(A–B) is a graph showing (A) the effects of chlormethiazole (CHLOR) and IVk (200 μM of each) on the membrane current induced by 10 μM GABA in a Xenopus oocyte expressing the α1β1γ2L isoform of human recombinant $GABA_A$ receptors, and (B) the effect of IVk on loss of the righting reflex in mice after intraperitoneal injection of 100 mg/kg and 200 mg/kg. Data in part B are mean±standard error for three animals at each dose.
Figure 15:
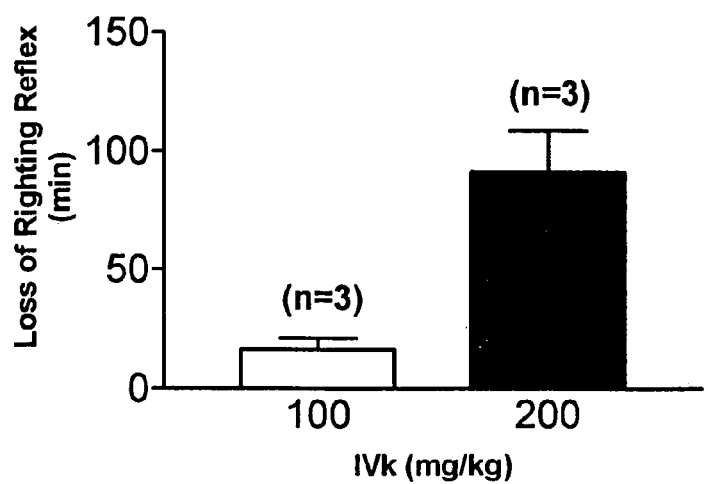

The effect of IVk was tested in *Xenopus* oocytes expressing human recombinant GABA$_A$ receptors by the two-electrode voltage clamp technique as described in Reynolds and Maitra (*European Journal of Pharmacology* (1996) 314, 151–156.). The control GABA response was substantially potentiated by the positive control drug, chlormethiazole, at a concentration of 200 µM (FIG. 15a). In contrast, a concentration of 200 µM of IVk produced a smaller, but still significant, potentiation of the control GABA response in the same oocyte (FIG. 15a). A decreased efficacy with IVk suggests the possibility that it is a partial allosteric modulator of $GABA_A$ receptor function, and may therefore have more selective behavioural effects than more efficacious compounds.

The effect of a drug that induces brief periods of sedation/hypnosis in animals is characterized by loss of the righting reflex (loss of the ability of the animal to right its posture when placed on its back). The "loss of the righting reflex" response is a commonly used test for sedative-hypnotic agents. IVk produced a dose-dependent and reversible loss of the righting reflex in mice when given by intraperitoneal injection at doses of 100 and 200 mg/kg (FIG. 15b). Thus, the organic nitrate IVk exhibits the activity of a sedative/hypnotic, and represents a novel class of compounds that may have utility as new anti-anxiety, sedative and/or hypnotic agents.

REFERENCES

Aley et al., *J. Neurosci.* (1998) 18, 7008.
T. Azuhata, Y. Okamoto, *Synthesis* (1983) 916–917.
Artz J. D., Thatcher, G. R. J., *Chem. Res. Toxicol.* (1998) 11, 1393.
Bak et al., *Life Sciences* (1998) 62, 367–373.
Barger, S W, RR Fiscus, P Ruth, F Hofmann, MP Mattson, "Role of cyclic GMP in the regulation of neuronal calcium and survival by secreted forms of β-amyloid precursor protein", *J. Neurochem.* (1995) 64, 2087–2096.
Bennett et al., *Can. J. Physiol. Pharmacol.* (1992) 70, 1297.
Berge et al., "Pharmaceutical Salts", *J. Pharm. Sci.* (1977) 66, 1–19.
Bloeman, P. G. et al., *FEBS Lett.* (1995) 357, 140.
Bourgeois, *Recl. Trav. Chim. Pays-Bas* (1899) 18, 445–450.
Briscoe et al., *Am. J Physiol.* (1995) 1233, 134.
Cunha, F. Q. et al., *Br. J Pharmacol.* (1999) 127, 671.
del Soldato, P. et al, *Trends Pharmacol. Sci.* (1999) 20, 319.
Ferreira et al., *Agents Actions Suppl.* (1991) 32, 101.
Ferreira, S. H., *Drugs* (1993) 46, 1.
Ferreira, S. H., *Ann. 1st Super Sanita* (1993) 29, 367.
Fidecka, S. et al., *Pol. J. Pharmacol.* (1997) 49, 395.
R. L. Frank, P. V. Smith, *J. Am. Chem. Soc.* (1946) 68, 2103–2104.
Granados-Soto et al., *Eur. J. Pharmacol.* (1997) 340, 177.
Inoue, T. et al., *J. Neurol. Sci.* (1997) 153, 1.
Lauretti, G. R. et al., *Anesthesiology* (1999) 90, 1528.
Louw, R., H. P. W. Vermeeren, J. J. A. Van Asten, W. J. Ultee, *J. Chem. Soc., Chem. Comm.* (1976) 496–497.
McDonald and Bennett, *Can. J. Physiol. Pharmacol* (1990) 68, 1552.
McGuire et al., *J. Pharmacol. Exp. Ther.* (1994) 271, 708.
Malmberg and Yaksh, *Anesthesiology* (1993) 79, 270–281.
Morgan et al., "Approaches to the discovery of non-peptide ligands for peptide receptors and peptidases", In *Ann. Rep. Med. Chem.* (Virick F. J., et al.) pp. 243–253, Academic Press, San Diego, Calif. (1989).
J.-P. Morizur, *Bull. Soc. Chim. Fr.* (1964) 1338–1342.
Ouellette, R. J., R. J. Bertsch, *J. Org. Chem.* (1976) 41, 2782–2783.
Owais, M. et al., *Antimicrob. Agents Chemother.* (1995) 39, 180.
Ranade, V. V., *J. Clin. Pharmacol.* (1989) 29, 685.
Reynolds and Maitra, *European Journal of Pharmacology* (1996) 314, 151–156.
Salter, M. et al., *Neuroscience* (1996) 73, 649.
K. B. Sharpless, W. Amberg, Y. L. Bennani, G. A. Crispino, J. Hartung, K.-S. Jeong, H.-L. K wong, K. Morikawa, Z.-M. Wang, D.Xu, X.-L. Zhang, *J. Org. Chem.* (1992) 57, 2768–2771.
Shibuta, S., *J. Neurol. Sci.* (1996) 141, 1.
Strejan et al., *J Neuroimmunol.* (1984) 7, 27.
Stewart et al., *Can. J. Physiol Pharmacol.* (1989) 67, 403.
J. R. Stone and M. A. Marletta, *Biochemistry* (1996) 35, 1093.
Sydserff et al., *Br. J. Pharmacol.* (1995) 114, 1631–1635.
Tjolsen et al., *Pain* (1992) 51, 5–17.
Umezawa et al., *Biochem. Biophys. Res. Commun.* (1988) 153, 1038.
Wu, J, Y Wang, M J Rowan, R Anwyl, "Evidence for involvement of the cGMP-protein kinase G signaling system in the induction of long-term depression, but not long-term potentiation, in the dentate gyrus in vitro", *J. Neurosci.* (1998) 18, 3589–3596.
Xu J. Y. et al., *Pain* (1995) 63, 377.
Yaksh, *TIPS* (1999) 20, 329–337.
Yang, K., J. D. Artz, J. Lock, C. Sanchez, B. M. Bennett, A. B. Fraser, G. R. Thatcher, *J. Chem. Soc., Perkin Trans.* (1996) 1, 1073–1075.

What is claimed is:

1. A method for reducing anxiety, aiding sleep, or inducing sleep in a subject in need thereof, comprising administering to the subject an effective amount of a therapeutic compound, wherein said therapeutic compound is of the formula (Ia):

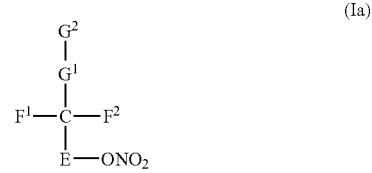

, in which $F^2$ is a nitrate group or an organic radical which may be joined in a cyclic ring system with $G^2$, and which may contain inorganic counterions;

E is a methylene group;

$G^1$ is a methylene group or does not exist;

$F^1$ is H; and $G^2$ is joined with $F^2$ to form a cyclic system or is $R^N$—$Z^N$; wherein $R^N$ is an organic radical possessing a heteroaryl group containing a P or S atom, where said P or S is positioned β, γ, or δ to a nitrate group; and $Z^N$ is $W^N_{mm}$—$X^N_{nn}$—$Y^N_{oo}$; wherein mm, nn, oo are 0 or 1 and $W^N$, $X^N$, $Y^N$ are NH, $NR^{NN}$, CO, O, or $CH_2$; wherein $R^{NN}$ is a $C_1$–$C_{12}$ alkyl group.

2. A method for reducing anxiety, aiding sleep, or inducing sleep in a subject in need thereof, comprising administering to said subject an effective amount of a therapeutic compound, wherein said therapeutic compound is of the formula (Ic):

47

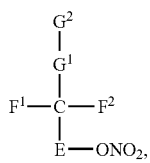

(Ic)

in which

E is $(R^1R^2C)_m$ and $G^2-G^1-CF^1F^2-$ is $R^{19}-(R^3R^4C)_p-(R^{17}R^{18}C)_n-$; wherein each of m, n, and p is an integer from 0 to 10;

$R^3$ and $R^{17}$ are each independently hydrogen, a nitrate group, or A; and $R^1$ and $R^4$ are each independently hydrogen, or A;

where A is selected from a substituted or unsubstituted aliphatic group comprising a branched or straight-chain aliphatic moiety having from 1 to 24 carbon atoms in the chain, which optionally may contain O, S, $NR^6$, or an unsaturation in the chain, optionally bearing from 1 to 4 hydroxy, nitrate, amino, aryl, or heterocyclic groups; an unsubstituted or substituted cyclic aliphatic moiety having from 3 to 7 carbon atoms in the aliphatic ring, which optionally may contain O, S, $NR^6$, or an unsaturation in the ring, optionally bearing from 1 to 4 hydroxy, nitrate, amino, aryl, or heterocyclic groups; an unsubstituted or substituted aliphatic moiety constituting a linkage of from 0 to 5 carbons, between $R^1$ and $R^3$ and/or between $R^{17}$ and $R^4$, which optionally may contain O, S, $NR^6$, or an unsaturation in the linkage, and optionally bearing from 1 to 4 hydroxy, nitrate, amino, aryl, or heterocyclic groups; a substituted or unsubstituted aliphatic group comprising a branched, cyclic or straight-chain aliphatic moiety having from 1 to 24 carbon atoms in the chain, containing linkages selected from the group consisting of C=O, C=S, and C=NOH, which optionally may contain O, S, $NR^6$, or an unsaturation in the chain, optionally bearing from 1 to 4 hydroxy, nitrate, amino, aryl, or heterocyclic groups; a substituted or unsubstituted aryl group; a substituted or unsubstituted heterocyclic group; an amino group selected from alkylamino, dialkylamino, cyclic amino, diamino, triamino, arylamino, diarylamino, and alkylarylamino moieties; hydroxy; alkoxy; and a substituted or unsubstituted aryloxy; wherein X is F, Br, Cl, $NO_2$, $CH_2$, $CF_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2H$, $PO_2M$, $P(O)(OR^{14})$, $P(O)(R^{13})$, SO, $SO_2$, $C(O)(SR^{13})$, $SR^5$, $SSR^7$ or $SSR^5$;

Y is F, Br, Cl, $CH_3$, $CF_2H$, $CF_3$, OH, $NH_2$, $NHR^6$, $NR^6R^7$, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(OR^{13})$, $C(O)(SR^{13})$, $SR^5$, $SSR^7$ or $SSR^5$, or does not exist;

each of $R^2$, $R^5$, $R^{18}$, and $R^{19}$ is, independently, hydrogen, A, or X—Y;

48 each of $R^6$, $R^7$, $R^8$, $R^9$, $R^{11}$, $R^{12}$, $R^{13}$, $R^{14}$, $R^{15}$, $R^{16}$ is, independently, an alkyl or acyl group containing 1–24 carbon atoms, which may contain 1–4 $ONO_2$ substituents; a $C_1$–$C_6$ connection to $R^1$–$R^4$ in a cyclic derivative, which may contain 1–4 $ONO_2$ substituents; a hydrogen, a nitrate group, or A;

M is H, $Na^+$, $K^+$, $NH_4^+$, or $N^+H_kR^{11}_{(4-k)}$, where k is 0–3; or other pharmaceutically acceptable counterion;

and with the proviso that when m=n=p=1 and $R^{19}$, $R^2$, $R^{18}$, $R^1$=H and $R^{17}$, $R^3$ are nitrate groups, $R^4$ is not H.

3. The method of claim 1, wherein $F^2$ is a nitrate group; with the proviso that when E and $G^1$ are methylene groups and $F^1$ is H, $G^2$ is not $R^N-Z^N$; wherein $R^N$ is any aryl or heteroaryl group and $Z^N$ is $(CO)_{mm}-X^N_{nn}-Y^N_{oo}$; wherein mm, nn, oo are 0 or 1 and $X^N$, $Y^N$ are NH, $NR^{NN}$, O or $CH_2$; wherein $R^{NN}$ is a $C_1$–$C_{12}$ alkyl group.

4. The method of claim 1, wherein $F^2$ is a nitrate group; E and $G^1$ are methylene groups; $F^1$ is H; and $G^2$ is $R^N-Z^N$; wherein $R^N$ is an organic radical possessing an heteroaryl group containing P or S atoms where said P or S are positioned β, γ, or δ to a nitrate group as identified in formula Ia; and $Z^N$ is $W^N_{mm}-X^N_{nn}-Y^N_{oo}$; wherein mm, nn, oo are 0 or 1 and $W^N$, $X^N$, $Y^N$ are NH, $NR^{NN}$, CO, O or $CH_2$; wherein $R^{NN}$ is a $C_1$–$C_{12}$ alkyl group.

5. The method of claim 2, wherein $R^{19}$ is X—Y.

6. The method of claim 5, wherein:

$R^1$ and $R^3$ are the same or different and selected from H and $C_1$–$C_4$, alkyl chains, which chains may include one O linking $R^1$ and $R^3$ to form pentosyl, hexosyl, cyclopentyl, or cyclohexyl rings, which rings may optionally bear hydroxyl substituents;

$R^2$ and $R^4$ are the same or different and selected from H, a nitrate group, a $C_1$–$C_4$ alkyl chain, optionally bearing 1–3 nitrate groups, and an acyl group ($-C(O)R^5$);

$R^7$ and $R^{11}$ are the same or different $C_1$–$C_8$ alkyl or $C_1$–$C_8$ acyl;

each of $R^5$, $R^6$, $R^8$, $R^9$, $R^{12}$, $R^{13}$, $R^{14}$, $R^{15}$, $R^{16}$ is, independently, an alkyl group containing 1–12 carbon atoms, which may contain 1–4 $ONO_2$ substituents; or a $C_1$ or $C_2$ connection to $R^1$–$R^3$ in a cyclic derivative; and M is H, $Na^+$, $K^+$, $NH_4^+$ or $N^+H_kR^{11}_{(4-k)}$, where k is 0–3.

7. The method of claim 6, wherein m=1, n=0, p=1.

8. The method of claim 7, wherein:

X is $CH_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2M$, $P(O)(OR^{14})$, $P(O)(R^{13})$, SO, $SO_2$, $C(O)(SR^{13})$, or $SSR^5$; and Y is CN, $N_2H_2R^{13}$, $N_2HR^{13}R^{14}$, $N_3$, SCN, $SCN_2H_2(R^{15})_2$, $SC(O)N(R^{15})_2$, $SC(O)NHR^{15}$, $SO_3M$, $SR^4$, $SO_2M$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(SR^{13})$, $SR^5$, or $SSR^5$, or does not exist.

9. The method of claim 7, wherein:

each of $R^5$, $R^6$, $R^8$, $R^9$, $R^{12}$, $R^{13}$, $R^{14}$, $R^{15}$, $R^{16}$ is, independently, an alkyl group containing 1–12 carbon atoms, which may contain 1–4 $ONO_2$ substituents; or a $C_1$ or $C_2$ connection to $R^1$–$R^3$ in a cyclic derivative X is $CH_2$, O, NH, NMe, S, $SO_3M$, SH, $SR^7$, $SO_2M$, $S(O)R^8$, $S(O)_2R^9$, $S(O)OR^8$, $S(O)_2OR^9$, $PO_3M_2$, $P(O)(OR^{15})(OR^{16})$, $P(O)(OR^{16})(OM)$, $P(O)(R^{15})(OR^8)$, $PO_3HM$ or $P(O)(OM)R^{15}$; and Y is $SO_2M$, $SO_3M$, $PO_3HM$, $PO_3M_2$, $P(O)(OR^{15})(OR^{16})$, $P(O)(OR^{16})(OM)$, $SR^5$, $SSR^7$ or $SSR^5$, or does not exist.

10. The method of claim 2, with the proviso that when m=n=p=1 and $R^{19}$, $R^2$, $R^{18}$, $R^1$=H and $R^{17}$, $R^3$ are nitrate groups, $R^4$ is not $C_1$–$C_3$ alkyl.

11. The method of any one of claims 1, 2, 3 or 4, further comprising administering said therapeutic compound with a pharmaceutically acceptable vehicle.

12. The method of any one of claims 1, 2, 3, or 4, wherein said therapeutic compound modulates levels of the cyclic nucleotides cGMP and/or cAMP in said subject.

13. The method of any one of claims 1, 2, 3, or 4, wherein said therapeutic compound modulates guanylyl cyclase activity in said subject.

14. A method of reducing anxiety, aiding sleep, or inducing sleep in a subject in need thereof, comprising administering to the subject an effective amount of a therapeutic compound selected from the group consisting of:

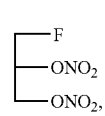
IIIa

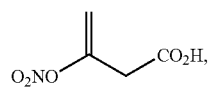
IIIb

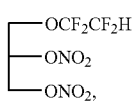
IIIc

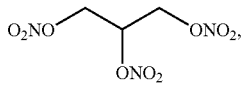
IIId

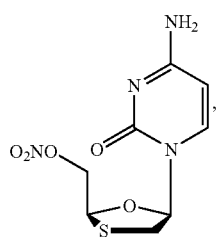
IIIe

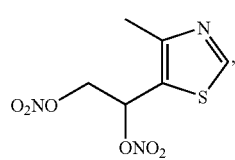
IIIf

-continued

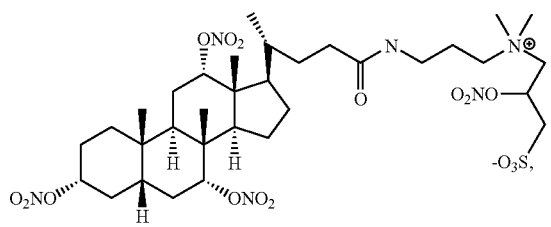
IIIg

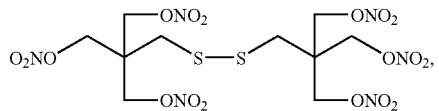
IIIh

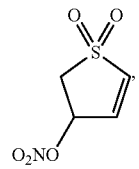
IIIi

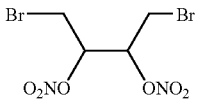
IIIj

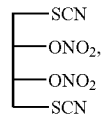
IIIk

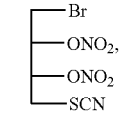
IIIl

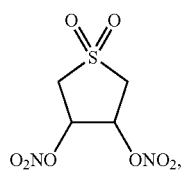
IIIm

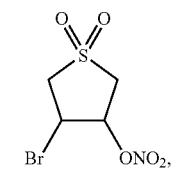
IIIn

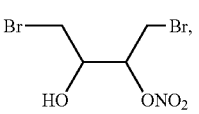
IIIo

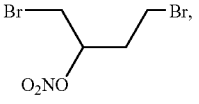
IIIp

-continued
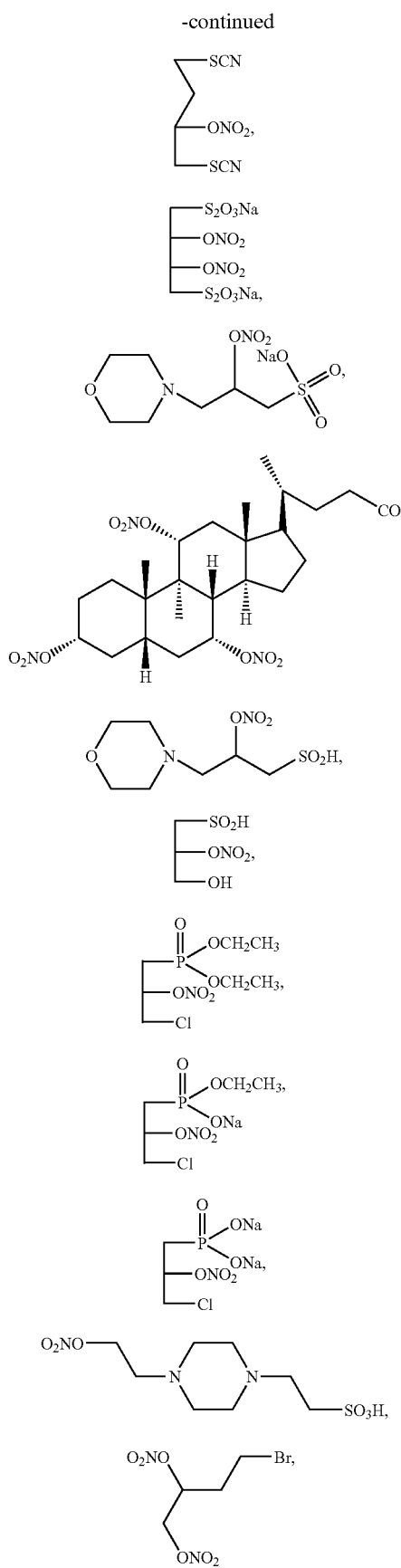
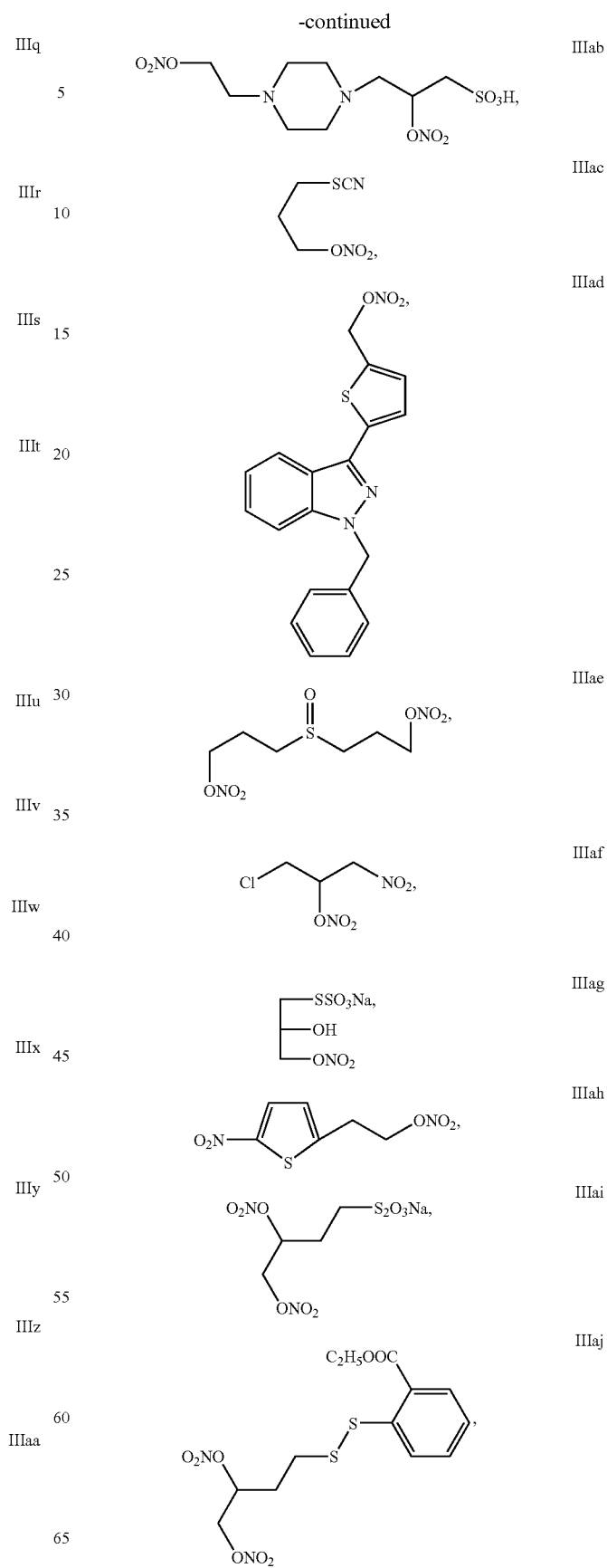

-continued

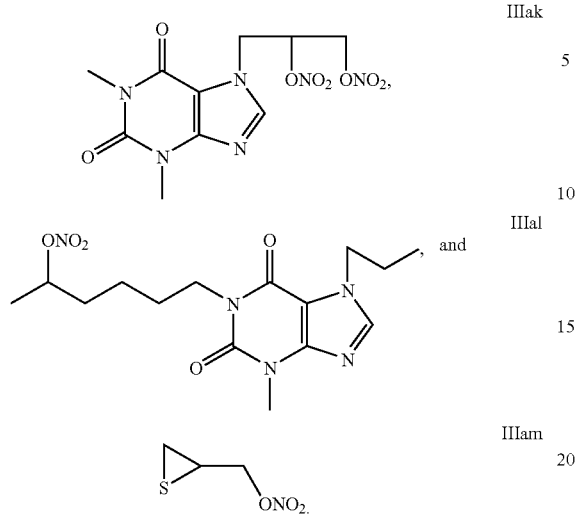

IIIak

IIIal, and

IIIam

15. The method of claim 14, wherein said compound has the formula IIIt:

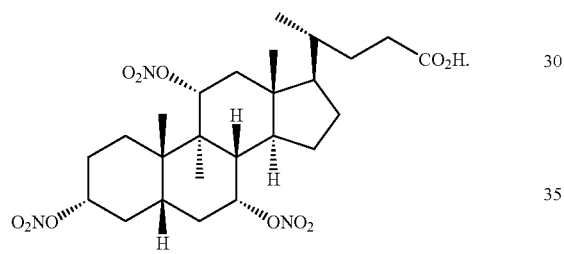

16. The method of claim 14, wherein said compound has the formula IIIf:

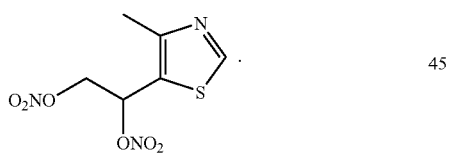

17. A method of reducing anxiety, aiding sleep, or inducing sleep in a subject in need thereof, comprising administering to said subject an effective amount of a therapeutic compound selected from the group consisting of:

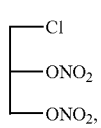

IVa

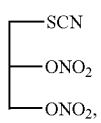

IVb

-continued

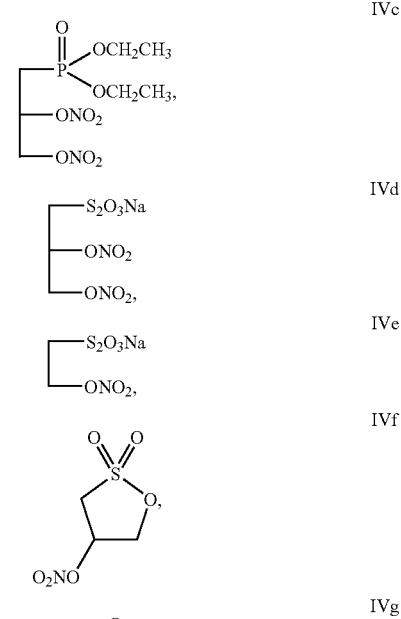

IVc

IVd

IVe

IVf

IVg

IVh

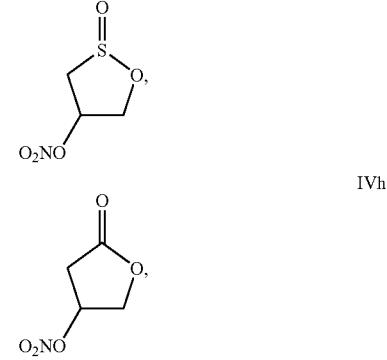

IVi

IVj

IVk

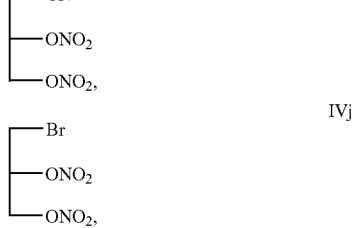

IVl

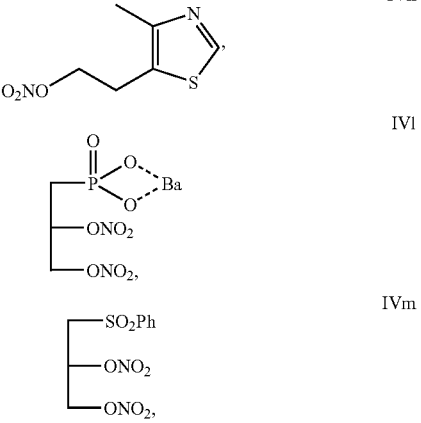

IVm

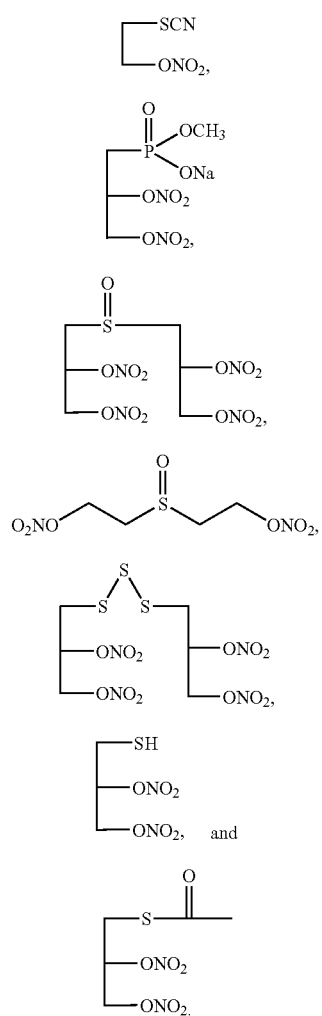

18. A method of reducing anxiety, aiding sleep, or inducing sleep in a subject in need thereof, comprising administering to said subject an effective amount of a therapeutic compound having the formula IVk:

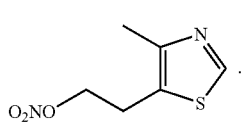

19. A method of reducing anxiety, aiding sleep, or inducing sleep in a subject in need thereof, comprising administering to the subject an effective amount of a therapeutic compound selected from the group consisting of:

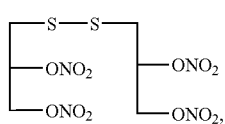

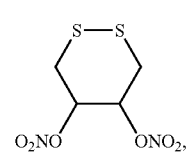

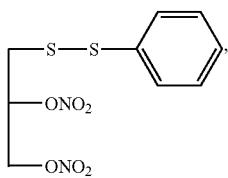 Vj
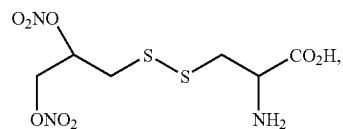 Vk
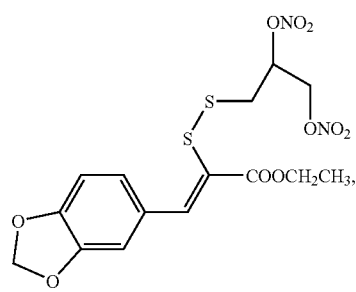 Vl
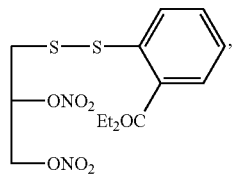 Vm
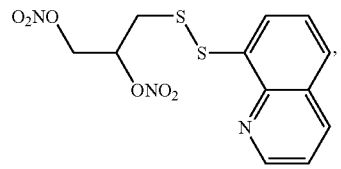 Vn
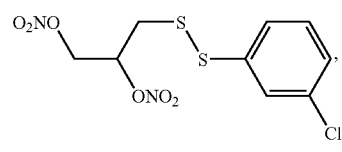 Vo
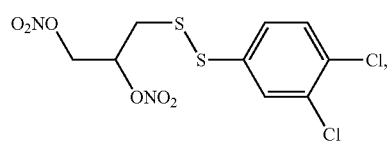 Vp
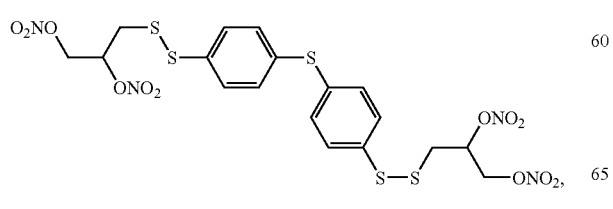 Vq
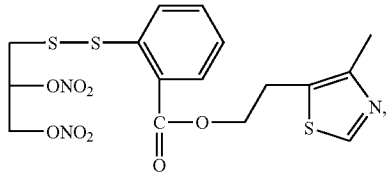 Vr
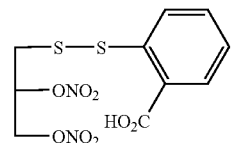 Vs
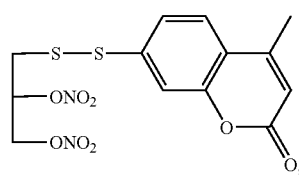 Vt
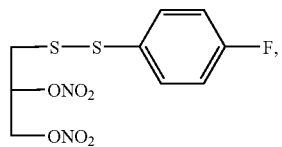 Vu
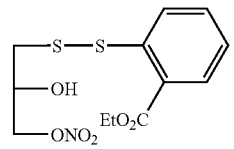 Vv
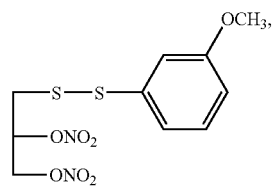 Vw
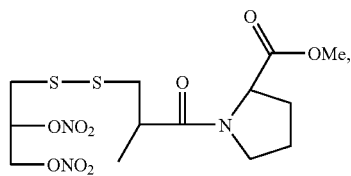 Vx
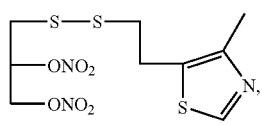 Vy
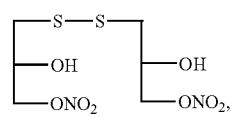 Vz
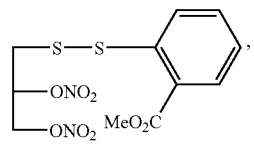 Vaa -continued

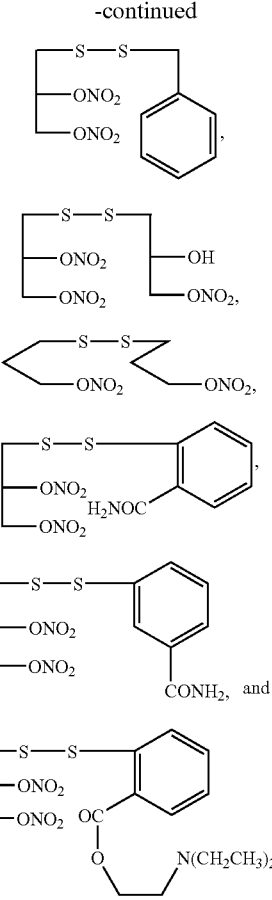

Vab

Vac

Vad

Vae

Vaf

Vag

20. The method of claim 19, wherein said compound has the formula Va:

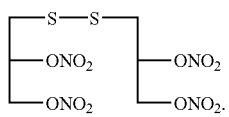

21. A method of reducing anxiety, aiding sleep, or inducing sleep in a subject in need thereof, comprising administering to said subject an effective amount of a therapeutic compound having the formula IVr:

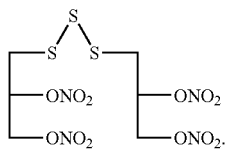

22. The method of claim 1, wherein
$G^2$ is not $R^N$—$Z^N$; wherein
$R^N$ is any aryl or heteroaryl group and $Z^N$ is $(CO)_{mm}$—$X^N_{nn}$—$Y^N_{oo}$; wherein mm, nn, oo are 0 or 1 and $X^N$, $Y^N$ are NH, $NR^{NN}$, O or $CH_2$; wherein
$R^{NN}$ is a $C_1$–$C_{12}$ alkyl group.

23. The method of claim 5, wherein

X is $CH_2$, $CF_2$, O, NH, NMe, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $C(O)$, SO, $SO_2$, $C(O)(SR^{13})$, $SR^5$, $SSR^7$ or $SSR^5$; and Y is SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $C(O)(SR^{13})$, $SR^5$, $SSR^7$ or $SSR^5$, or does not exist.

24. A method of providing sedation or anesthesia in a subject in need thereof, comprising administering to the subject an effective amount of a therapeutic compound selected from the group consisting of:

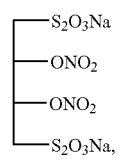

IIIr

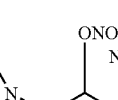

IIIs

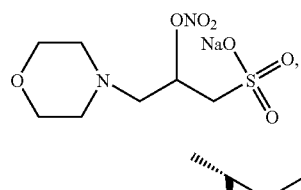

IIIt

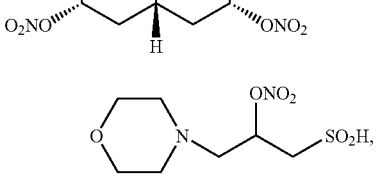

IIIu

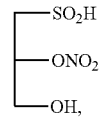

IIIv

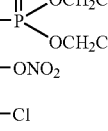

IIIw

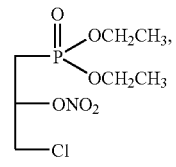

IIIx

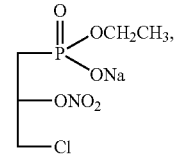

-continued

25. A method of providing sedation or anesthesia in a subject in need thereof, comprising administering to said subject an effective amount of a therapeutic compound selected from the group consisting of:

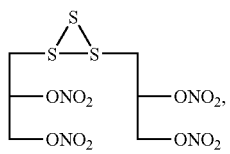
IVr
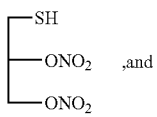
IVs
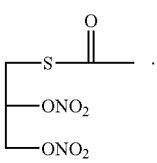
IVt
26. A method of providing sedation or anesthesia in a subject in need thereof, comprising administering to said subject an effective amount of a therapeutic compound selected from the group consisting of:
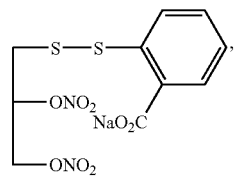
Vd
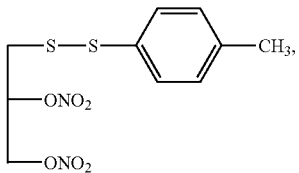
Ve
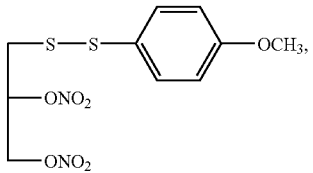
Vf
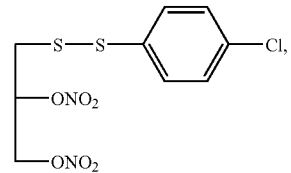
Vg
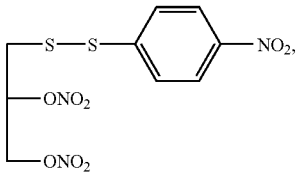
Vh
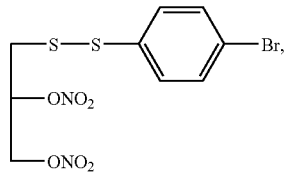
Vi
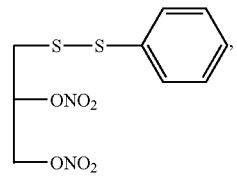
Vj
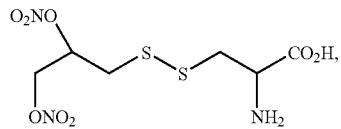
Vk
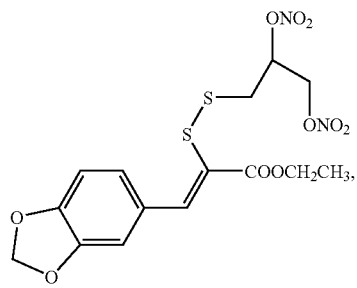
Vl
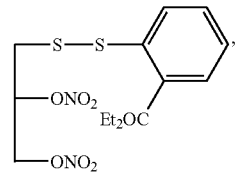
Vm
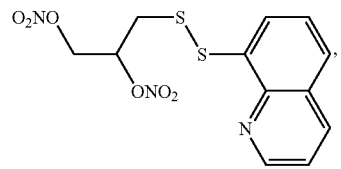
Vn
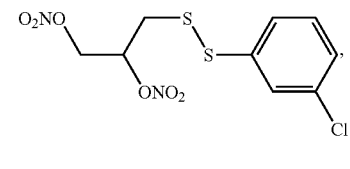
Vo
Vp -continued

[Structures Vq, Vr, Vs, Vt, Vu, Vv, Vw, Vx, Vy, Vz, Vaa, Vab, Vac, Vad, Vae, Vaf, and Vag]

* * * * *

UNITED STATES PATENT AND TRADEMARK OFFICE
CERTIFICATE OF CORRECTION

PATENT NO.         : 7,115,661 B2
APPLICATION NO. : 09/473713
DATED                 : October 3, 2006
INVENTOR(S)       : Thatcher et al.

It is certified that error appears in the above-identified patent and that said Letters Patent is hereby corrected as shown below:

On the Cover Sheet, in References Cited, in OTHER PUBLICATIONS, in Lin et al., replace "Lin, Q.,et al.," with --Lin, Q., et al.,--.

Column 5, Line 29, replace "Formula II):" with --(Formula II):--.

Column 8,
  Line 5, replace "IVn-Ivt" with --IVn-IVt--;
  Line 53, replace "homogenate homogenate" with --homogenate--.

Column 13,
  Line 45, replace "inlude" with --include--;
  Line 47, replace "cycohexyl" with --cyclohexyl--.

Column 14, Line 31, replace "Formulae" with --Formula--.

Column 18, Line 54, replace "(Formulae IVa-IVt):" with --(Formula IVa-IVt):--.

Column 20, Line 53, replace "(Formulae" with --(Formula--.

Column 33, Line 52, replace "Ivf" with --IVf--.

Column 36, Line 56, replace "therafter" with --thereafter--.

Column 37, Line 1, replace "Bak et al" with --Bak et al.--.

Column 38,
  Line 12, replace "rotavary" with --rotary--;
  Line 44, replace "eluent" with --eluant--;
  Line 55, replace "hydrocloric" with --hydrochloric--.

Column 40,
  Line 24, replace "allyphenyl" with --allyl phenyl--;
  Line 67, replace "seperated" with --separated--.

Column 41, Line 39, replace "ot" with --to--.

Column 42, Line 49, replace "sterechemically" with --stereochemically--.

UNITED STATES PATENT AND TRADEMARK OFFICE
CERTIFICATE OF CORRECTION

PATENT NO. : 7,115,661 B2
APPLICATION NO. : 09/473713
DATED : October 3, 2006
INVENTOR(S) : Thatcher et al.

It is certified that error appears in the above-identified patent and that said Letters Patent is hereby corrected as shown below:

Column 43,
    Line 34, replace "Ethylisothiocyanate" with --Ethyl isothiocynate--;
    Line 52, replace "hydrolized" with --hydrolyzed--;
    Line 61, replace "cromatography eluating" with --chromatography eluting--.

Signed and Sealed this

Thirteenth Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 7,115,661 B1
APPLICATION NO. : 09/473713
DATED : October 3, 2006
INVENTOR(S) : Thatcher et al.

Page 1 of 1

It is certified that error appears in the above-identified patent and that said Letters Patent is hereby corrected as shown below:

Column 43, line 34, replace "Ethyl isothiocynate" with --Ethyl isothiocyanate--.

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,115,661 B1 | Page 1 of 1 |
| APPLICATION NO. | : 09/473713 | |
| DATED | : October 3, 2006 | |
| INVENTOR(S) | : Thatcher et al. | |

It is certified that error appears in the above-identified patent and that said Letters Patent is hereby corrected as shown below:

Column 9, Line 45, delete "GT".

Column 35, Line 52, replace "UVd" with --IVd--.

Column 41, Line 39, replace "to" with --or--.

Signed and Sealed this

Twentieth Day of November, 2007

JON W. DUDAS
*Director of the United States Patent and Trademark Office*